(12) United States Patent
Lu et al.

(10) Patent No.: US 9,896,483 B2
(45) Date of Patent: Feb. 20, 2018

(54) STABILIZED HEPATITIS B CORE POLYPEPTIDES

(71) Applicant: The Board of Trustees of the Leland Stanford Junior University, Stanford, CA (US)

(72) Inventors: Yuan Lu, Palo Alto, CA (US); James Robert Swartz, Menlo Park, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 21 days.

(21) Appl. No.: 14/807,787

(22) Filed: Jul. 23, 2015

(65) Prior Publication Data

US 2015/0329598 A1    Nov. 19, 2015

Related U.S. Application Data

(63) Continuation of application No. PCT/US2014/012586, filed on Jan. 22, 2014.

(60) Provisional application No. 61/755,850, filed on Jan. 23, 2013, provisional application No. 61/901,243, filed on Nov. 7, 2013.

(51) Int. Cl.
| | |
|---|---|
| *C07K 14/005* | (2006.01) |
| *C12P 21/02* | (2006.01) |
| *C07K 14/02* | (2006.01) |
| *A61K 39/29* | (2006.01) |

(52) U.S. Cl.
CPC .......... *C07K 14/005* (2013.01); *C07K 14/02* (2013.01); *C12P 21/02* (2013.01); *A61K 39/29* (2013.01); *C12N 2730/10122* (2013.01); *C12N 2730/10123* (2013.01); *C12N 2770/32423* (2013.01); *C12N 2770/32434* (2013.01)

(58) Field of Classification Search
None
See application file for complete search history.

(56) References Cited

U.S. PATENT DOCUMENTS

| | | | |
|---|---|---|---|
| 5,968,767 | A | 10/1999 | Sheikh et al. |
| 6,099,846 | A | 8/2000 | Levy et al. |
| 6,168,931 | B1 | 1/2001 | Swartz et al. |
| 6,194,388 | B1 | 2/2001 | Krieg et al. |
| 6,207,646 | B1 | 3/2001 | Krieg et al. |
| 6,225,292 | B1 | 5/2001 | Raz et al. |
| 6,239,116 | B1 | 5/2001 | Krieg et al. |
| 6,337,191 | B1 | 1/2002 | Swartz et al. |
| 6,406,705 | B1 | 6/2002 | Davis et al. |
| 6,429,199 | B1 | 8/2002 | Krieg et al. |
| 6,548,276 | B2 | 4/2003 | Swartz et al. |
| 6,586,207 | B2 | 7/2003 | Tirrell et al. |
| 6,593,103 | B1 | 7/2003 | Lingappa et al. |
| 6,653,292 | B1 | 11/2003 | Krieg et al. |
| 6,719,978 | B2 | 4/2004 | Schiller et al. |
| 6,994,986 | B2 | 2/2006 | Swartz et al. |
| 7,041,479 | B2 | 5/2006 | Swartz et al. |
| 7,045,337 | B2 | 5/2006 | Schultz et al. |
| 7,083,970 | B2 | 8/2006 | Schultz et al. |
| 7,198,915 | B2 | 4/2007 | Tirrell et al. |
| 7,371,572 | B2 | 5/2008 | Schiller et al. |
| 7,375,234 | B2 | 5/2008 | Sharpless et al. |
| 7,402,572 | B2 | 7/2008 | Krieg et al. |
| 7,479,280 | B2 | 1/2009 | Schiller et al. |
| 7,517,520 | B2 | 4/2009 | Bachmann et al. |
| 7,615,227 | B2 | 11/2009 | Klinman et al. |
| 7,713,532 | B2 | 5/2010 | Maki et al. |
| 7,713,721 | B2 | 5/2010 | Schultz et al. |
| 7,718,410 | B2 | 5/2010 | Deiters et al. |
| 7,723,070 | B2 | 5/2010 | Tirrell et al. |
| 7,763,736 | B2 | 7/2010 | Sharpless et al. |
| 7,824,893 | B2 | 11/2010 | Deiters et al. |
| 7,871,794 | B2 | 1/2011 | Knapp et al. |
| 7,875,450 | B2 | 1/2011 | Schiller et al. |
| 7,888,063 | B2 | 2/2011 | Deiters et al. |
| 7,935,351 | B2 | 5/2011 | Klinman et al. |
| 7,964,196 | B2 | 6/2011 | De Los Rios et al. |
| 7,993,872 | B2 | 8/2011 | Deiters et al. |
| 8,008,266 | B2 | 8/2011 | Krieg et al. |
| 8,067,011 | B2 | 11/2011 | Davis et al. |
| 8,119,340 | B2 | 2/2012 | Messmer et al. |
| 8,129,542 | B2 | 3/2012 | Sharpless et al. |
| 8,420,792 | B2 | 4/2013 | Tian et al. |
| 8,445,446 | B2 | 5/2013 | Deiters et al. |
| 8,445,706 | B2 | 5/2013 | Shen |
| 8,466,116 | B2 | 6/2013 | Klinman et al. |
| 8,481,045 | B2 | 7/2013 | Swartz et al. |
| 8,568,706 | B2 | 10/2013 | Grabstein et al. |
| 8,580,970 | B2 | 11/2013 | Sharpless et al. |
| 8,691,209 | B2 | 4/2014 | Bachmann et al. |

(Continued)

FOREIGN PATENT DOCUMENTS

| | | | |
|---|---|---|---|
| EP | 1054689 | A1 | 11/2000 |
| EP | 1507769 | B1 | 5/2010 |

(Continued)

OTHER PUBLICATIONS

US 6,008,200, 12/1999, Krieg et al. (withdrawn)
Strable et al., "Unnatural amino acid incorporation into virus-like particles", Bioconjugate Chemistry, Apr. 16, 2008, pp. 866-675, vol. 19, No. 4, ACS, Washington, DC.
Pumpens et al., "Hepatitis B core particles as a universal display model: a structure-function basis for development", Febs Letters, Jan. 8, 1999, pp. 1-6, vol. 442, No. 1, Wiley, Hoboken, NJ.
Lu et al., "Assessing sequence plasticity of a virus-like nanoparticle by evolution toward a versatile scaffold for vaccines and drug delivery", Proceedings of the National Academy of Sciences, Oct. 6, 2015, pp. 12360-12365, vol. 112, No. 40, PNAS, Washington, DC.

(Continued)

*Primary Examiner* — Nicole Kinsey White
(74) *Attorney, Agent, or Firm* — Pamela J. Sherwood; Bozicevic, Field & Francis LLP

(57) ABSTRACT

Genetically modified HBc polypeptides are provided.

10 Claims, 21 Drawing Sheets
(18 of 21 Drawing Sheet(s) Filed in Color)

(56) References Cited

U.S. PATENT DOCUMENTS

| | | |
|---|---|---|
| 2004/0209321 A1 | 10/2004 | Swartz et al. |
| 2004/0234554 A1 | 11/2004 | Murray et al. |
| 2005/0054032 A1 | 3/2005 | Voloshin et al. |
| 2005/0054044 A1 | 3/2005 | Swartz et al. |
| 2006/0240024 A1 | 10/2006 | Pardoll et al. |
| 2006/0292174 A1 | 12/2006 | De Los Rios |
| 2008/0096819 A1 | 4/2008 | Grabstein et al. |
| 2009/0263405 A1 | 10/2009 | Verthelyi et al. |
| 2009/0317861 A1 | 12/2009 | Bundy et al. |
| 2010/0093024 A1 | 4/2010 | Goerke et al. |
| 2010/0167981 A1 | 7/2010 | Bundy et al. |
| 2010/0168402 A1 | 7/2010 | Bundy et al. |
| 2013/0156818 A1* | 6/2013 | de los Rios .......... A61K 9/5184 424/400 |
| 2013/0295131 A1 | 11/2013 | Padgett |

FOREIGN PATENT DOCUMENTS

| | | |
|---|---|---|
| WO | WO 2000/023955 | 4/2000 |
| WO | 2005/005614 A2 | 1/2005 |
| WO | WO 2005/003294 | 1/2005 |
| WO | WO 2005/052117 | 6/2005 |
| WO | WO 2005/078817 | 8/2005 |
| WO | WO 2004/016778 | 2/2006 |
| WO | PCT/US2007/015270 | 8/2007 |
| WO | WO 2008/002673 | 1/2008 |
| WO | WO 2008/066583 | 6/2008 |
| WO | 2010/042755 A2 | 4/2010 |
| WO | WO 2011/109422 | 9/2011 |
| WO | WO 2013/116656 | 8/2013 |
| WO | WO 2014/116730 | 7/2014 |
| WO | WO 2014/145932 | 9/2014 |
| WO | PCT/US2014/030788 | 11/2014 |
| WO | PCT/US2014/069406 | 4/2015 |
| WO | WO 2015/089114 | 6/2015 |

OTHER PUBLICATIONS

Database UniProt [Online], "RecName: Full=External core antigen {ECO: 0000256 RuleBase:RU361253};", Mar. 1, 2003.
Database EMBL [Online], "Hepatitis B virus DNA, complete genome, isolate:HBV-PH20", retrieved from EBI accession No. EMBL: AB116092, Database accession No. AB116092, Jan. 31, 2004, pp. 1-3.
Database EMBL [Online], "Hepatitis B virus isolate EIH21AChinese, complete genome", retrieved from EBI accession No. EMBL:EF473974, Database accession No. EF473974, May 20, 2008, pp. 1-4.
Database EMBL [Online], "Hepatitis B virus strain 28020 core protein gene, complete cds", retrieved from EBI accession No. EMBL:EU414050, Database accession No. EU414050, May 25, 2008, pp. 1-2.
Database EMBL [Online], "Hepatitis B virus isolate BA191 X protein, precorejcore protein and core protein genes partial cds", retrieved from EBI accession No. EMBL:HM214753, Database accession No. HM214753, Aug. 27, 2010, pp. 1-2.
Lu et al., "Assessing sequence plasticity of a virus-like nanoparticle by evolution toward a versatile scaffold for vaccines and drug delivery", PNAS, Oct. 6, 2015, pp. 12360-12365, vol. 112, No. 40, PNAS, Washington, DC.
Pumpens et al., "HBV Core Particles as a Carrier for B Cell/T Cell Epitopes", Intervirology, Jan. 1, 2001 pp. 98-114, vol. 44, No. 2-3, S. Karger AG, Basel, CH.
Brown et al., "RNA Bacteriophage capsid-mediated drug delivery and Epitope Presentation," Introvirology, 2002. 45:371-380.
Calhoun, et al., "Energizing cell-free protein synthesis with glucose metabolism," Biotechnology and Bioengineering, 2005. 90(5):606-613.
Carrico, et al., "Oxidative coupling of peptides to a virus capsid containing unnatural amino acids," Chem. Commun, 2008. 10:1205-1207.
Dooher, "Cell-free systems for capsid assembly of primate lentiviruses from three different lineages," J. Med. Primatol., 2004. 33:272-280.
Forconi et al., "Insight into the potential for DNA idiotypic fusion vaccines designed for patients by analyzing xenogeneic anti-idiotypic antibody responses," Immunology, 2002. 107(1):39-45; Abstract, p. 40-41, Table 1 and its legend; p. 44, col. 1-2.
Glover, "Efficient translation of the coat protein cistron of tobacco mosaic virus in a cell-free system from *Escherichia coli*," Eur. J. Biochem., 1982. 122:485-492.
Grgacic, et al., "Virus-like particles: passport to immune recognition," Methods, 2006. 40:60-65.
Jegerlehner, et al., "A molecular assembly system that renders antigens of choice highly repetitive for induction of protective B cell responses," Vaccine, 2002. 20:3104-3112.
Jewett, et al., "Prokaryotic systems for in vitro expression," Gene Cloning and Expression Technologies, 2002, p. 391-411.
Jewett, et al., "Mimicking the *Escherichia coli* cytoplasmic environment activates long-lived and efficient cell-fee protein synthesis," Biotechnology and Bioengineering, 2004. 86(1):19-26.
Kang et al., "Enhancement of mucosal immunization with virus-like particles of simian immunodeficiency virus," Journal of Virology, 2003. 77(6):3615-23; Abstract, p. 3616, col. 1.
Katanaev, et al., "Formation of bacteriophage MS2 infectious units in a cell-free translation system," FEBS Letters, 1996. 397:143-148.
Kazaks, et al., "Mosaic hepatitis B virus core particles presenting the complete preS sequence of the viral envelope on their surface," Journal of General Virology, 2004. 85:2665-2670.
Kratz, et al., "Native display of complete foreign protein domains on the surface of hepatitis B virus capsids," PNAS, 1999. 96:1915-1920.
Lin et al., "Genetic reconstruction of the aerobic central metabolism in *Escherichia coli* for the absolute aerobic production of succinate," Biotechnology and Bioengineering, 2004. 89(2):148-156.
Lingappa, et al., Comparing capsid assembly of primate lentiviruses and hepatitis B virus using cell-free systems, Virology, 2005. 333:114-123.
Mastico, et al., "Multiple presentation of foreign peptides on the surface of an RNA-free spherical bacteriophage capsid," J. Gen. Virology, 1993. 74:541-548.
Meldal, "Polymer "Clicking" by CuAAC Reactions," Macromol. Rapid Commun., 2008. 29:1016-1051.
Meldal et al., "Cu-Catalyzed Azide-Alkyne Cycloaddition," Chem. Rev., 2008. 108:2952-3015.
Noad et al., Virus-like particles as immunogens, TRENDS in Microbiology, 2003. 11(9):438-444.
Palucha, et al., "Virus-like particles: Models for assembly studies and foreign epitope carriers," Progress in Nucleic Acid Research and Molecular Biology, 2005. 80:135-168.
Pattenden, "Towards the preparative and large-scale precision manufacture of virus-like particles," TRENDS in Biotechnology, Oct. 2005. vol. 23, No. 10.
Patel, K. G. and J. R. Swartz, "Surface functionalization of virus-like particles by direct conjugation using azide-alkyne click chemistry." Bioconjug Chem, 2011. 22(3): 376-387.
Reddy et al., "Molecular rescue of tumor-specific T cell receptor idiotype from T cell lymphomas," British Journal of Haematology, 2004, 124(5):626-628; Abstract, p. 626, col. 1.
Rohrman, "The self-assembly of RNA free protein subunits from bacteriophage MS-2," Biochemical and Biophysical Research Communications, 1970. 38(3):406-413.
Sakalain, et al., "Synthesis and assembly of retrovirus Gag precursors into immature capsids in vitro," J. Virology, 1996. 70(6):3706-3715.
Spirin, et al., "A continuous cell-free translation system capable of producing polypeptides in high yield," Science, 1988. 242:1162-1164.
Stoll et al., "Immunization with peptides derived from the idiotypic region of lupus-associated autoantibodies delays the development of lupus nephritis in the (SWR x NZB)F1 murine model." Journal of Autoimmunology, 2007. 29(1):30-7; Abstract, p. 31.
Strable, et al., "Unnatural amino acid incorporation into virus-like particles." Bioconjug. Chem, 2008. 19(4):866-875.

(56) References Cited

OTHER PUBLICATIONS

Swartz, "Total synthesis and assembly of a virus-like particle," WTEC North American Baseline Workshop on R&D in Vaccine Manufacturing, Jan. 23, 2007.

Villinger, et al., "IL-15 is superior to IL-2 in the generation of long-lived antigen specific memory CD4 and CD8 T cells in rhesus macaques," Vaccine, 2004. 22:3510-3521.

Voloshin, A. M. and J. R. Swartz, "Efficient and scalable method for scaling up cell free protein synthesis in batch mode." Biotechnology and Bioengineering, 2005. 91(4): 516-521.

Wu, et al., "Cell-specific delivery of bacteriophage-encapsidated ricin a chain," Bioconjugate Chem., 1995. 6:587-595.

Arnold, Philipp, 3D-Electron Microscopy of Protein Complexes of Different Size and Symmetry, Dissertation Johannes Gutenberg-Universitat Mainz, Oct. 2012, 135 pages.

* cited by examiner

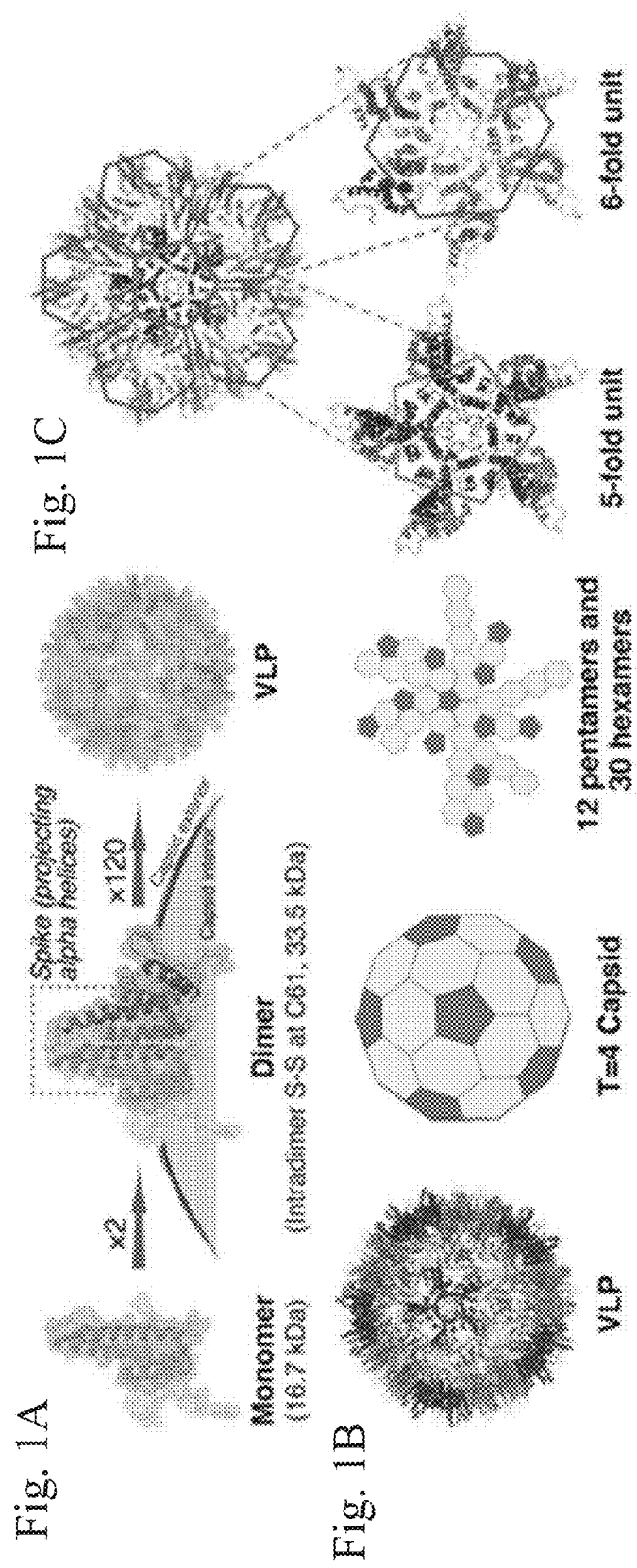

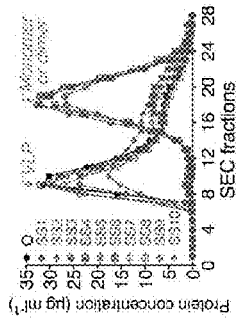
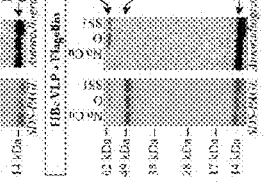
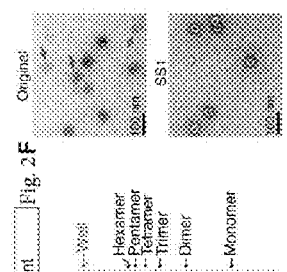
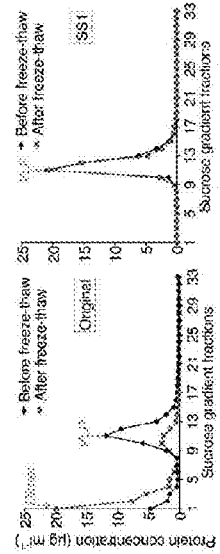
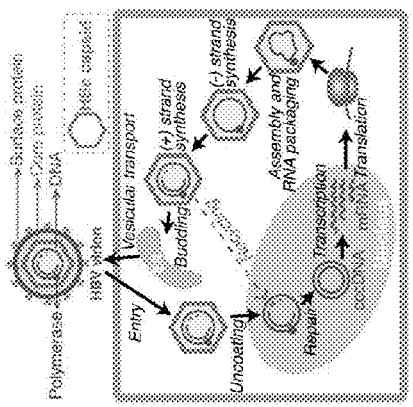
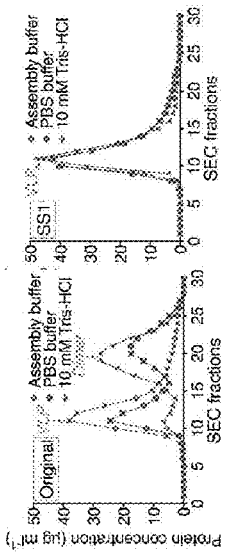

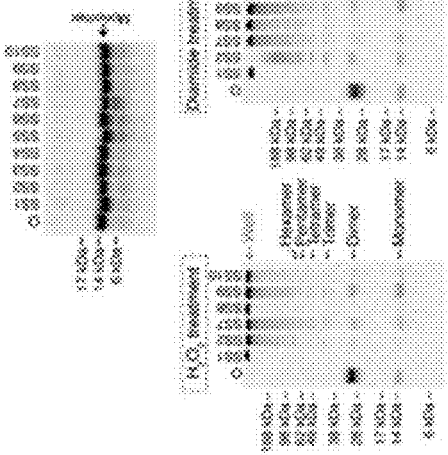
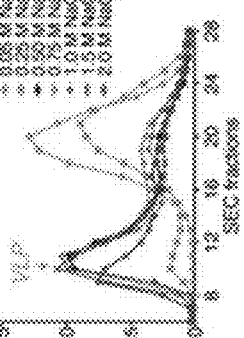
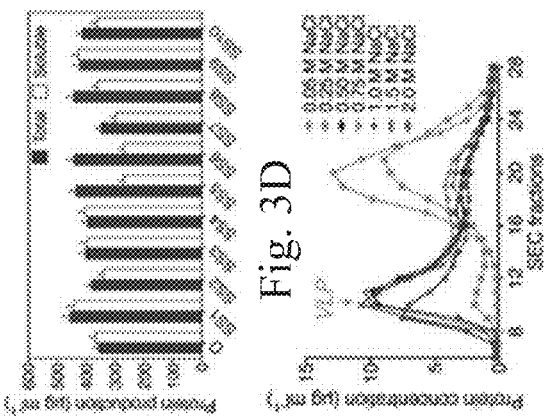
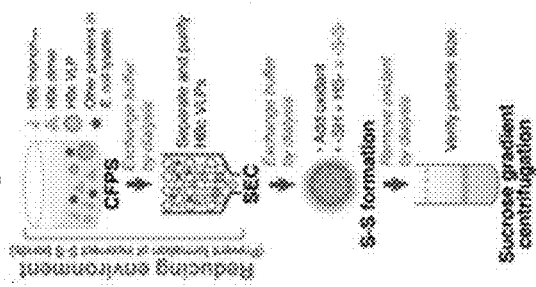
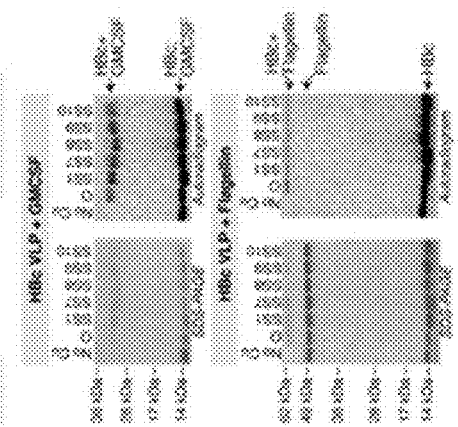
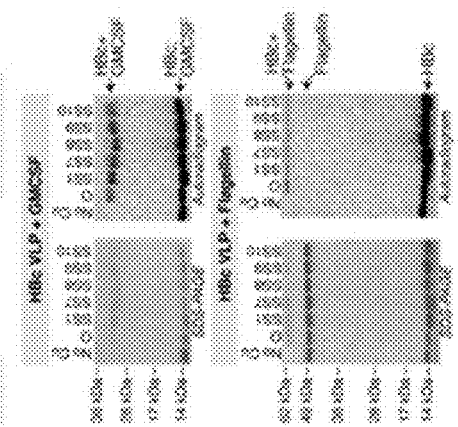
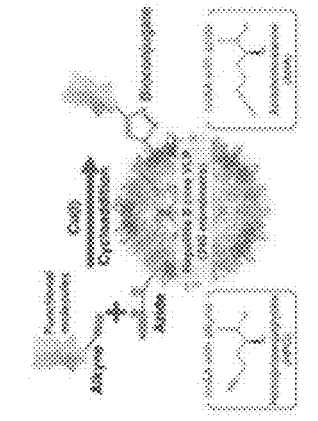
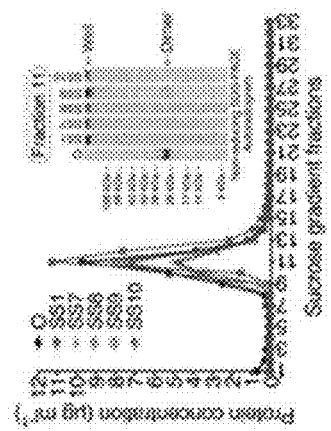

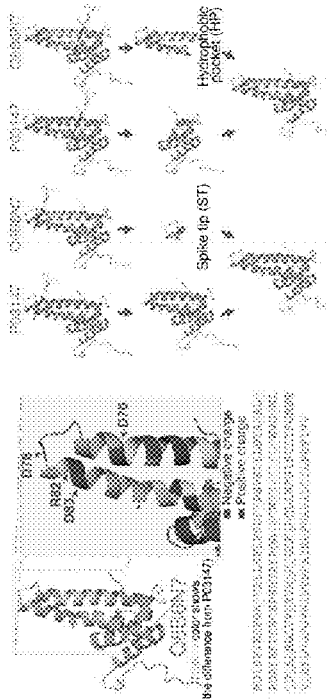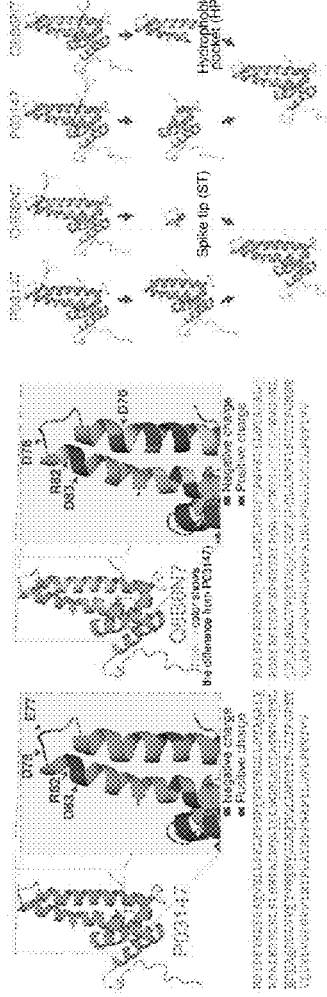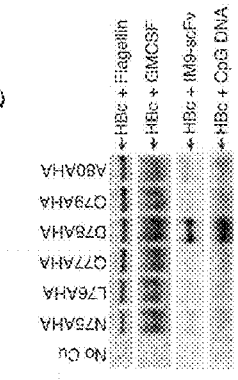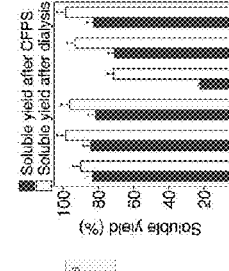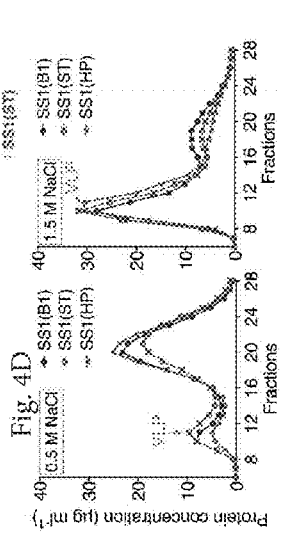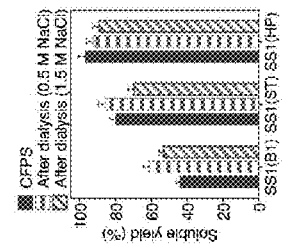

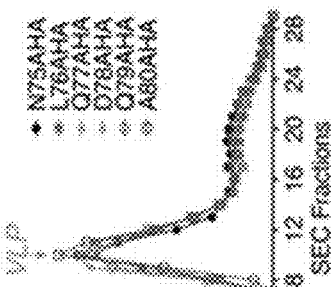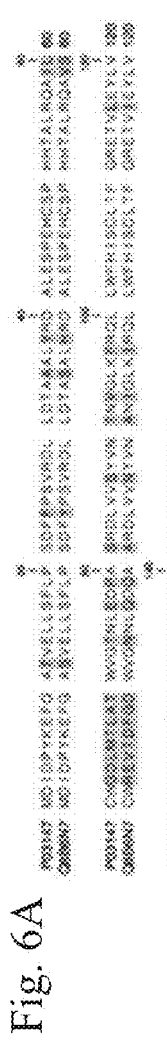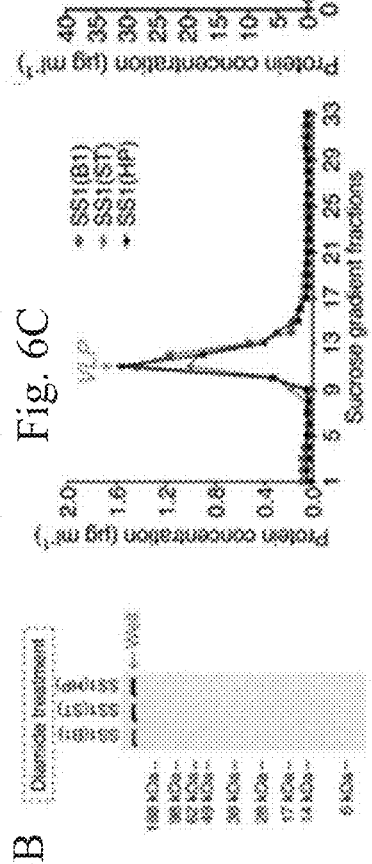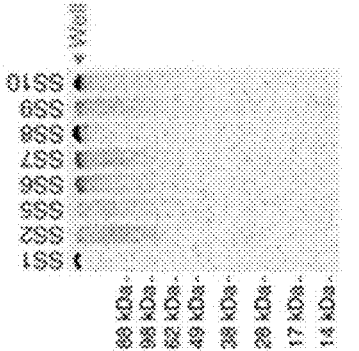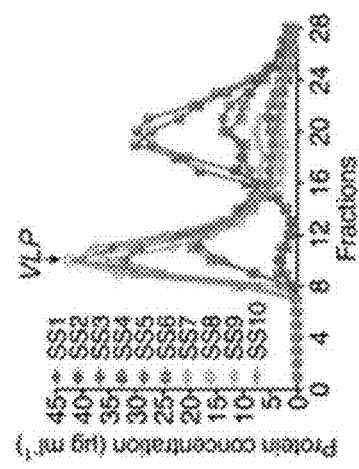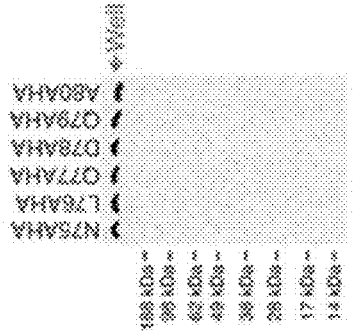
Fig. 6A Fig. 6B Fig. 6C Fig. 6D Fig. 6E Fig. 6F Fig. 6G

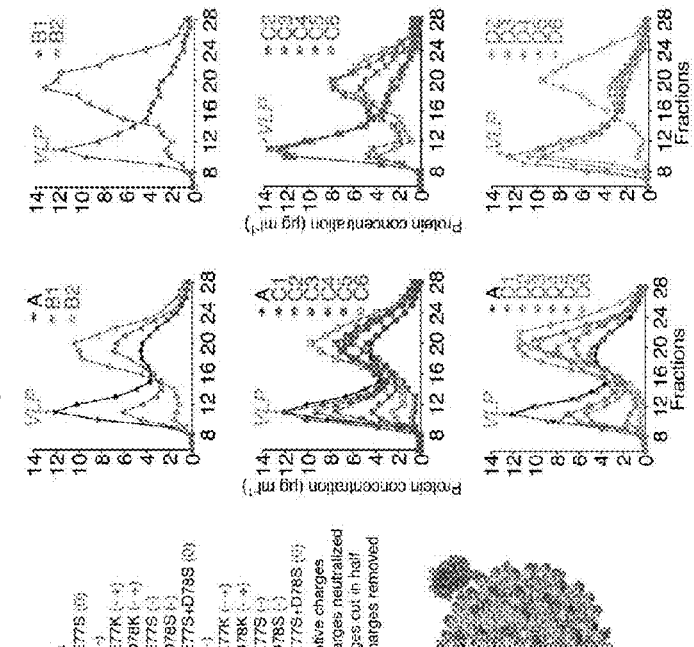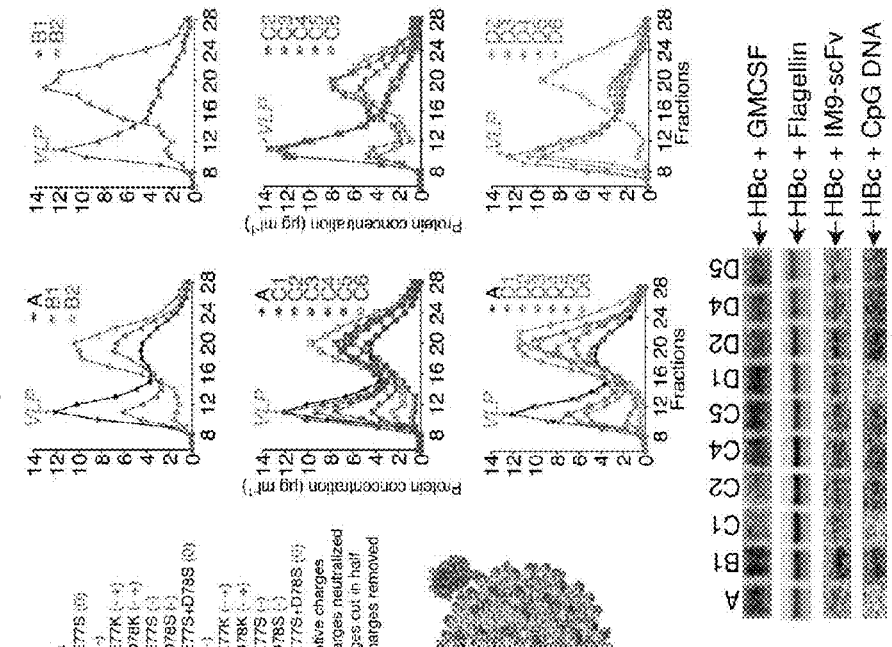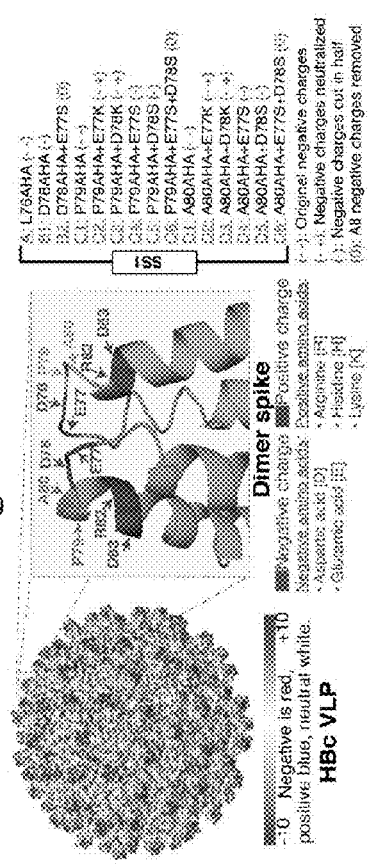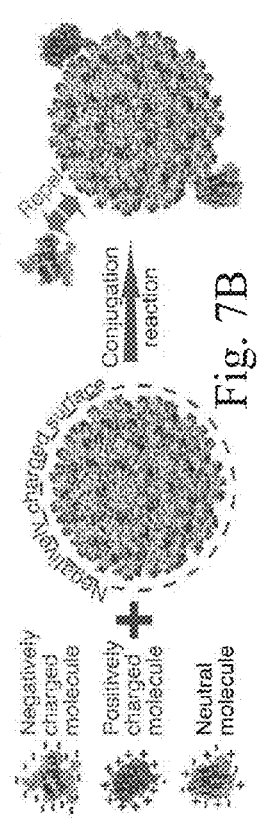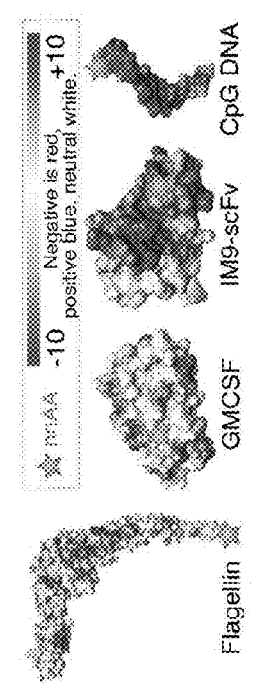
Fig. 7A  Fig. 7B  Fig. 7C  Fig. 7D  Fig. 7E  Fig. 7F

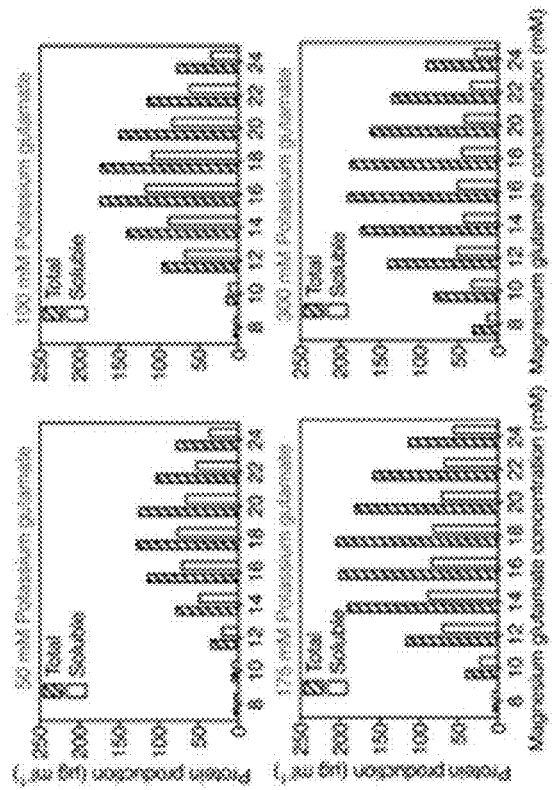
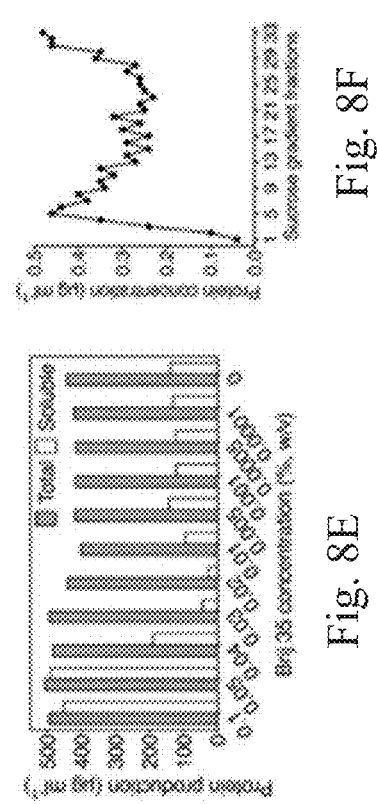
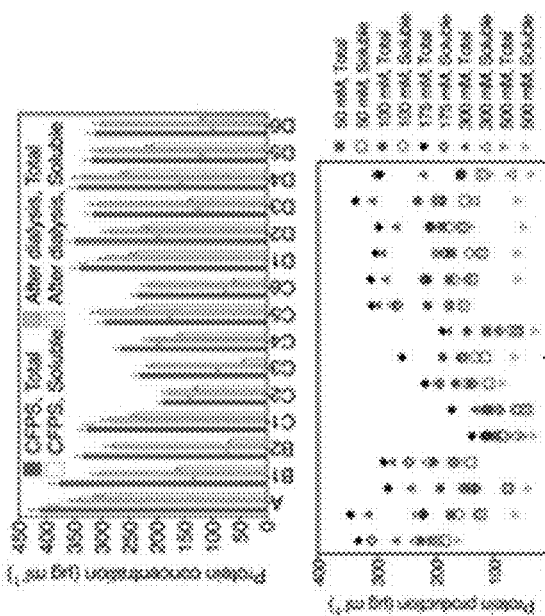
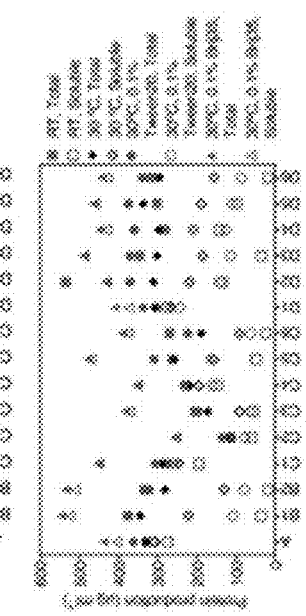
Fig. 8A  Fig. 8B  Fig. 8C  Fig. 8D  Fig. 8E  Fig. 8F

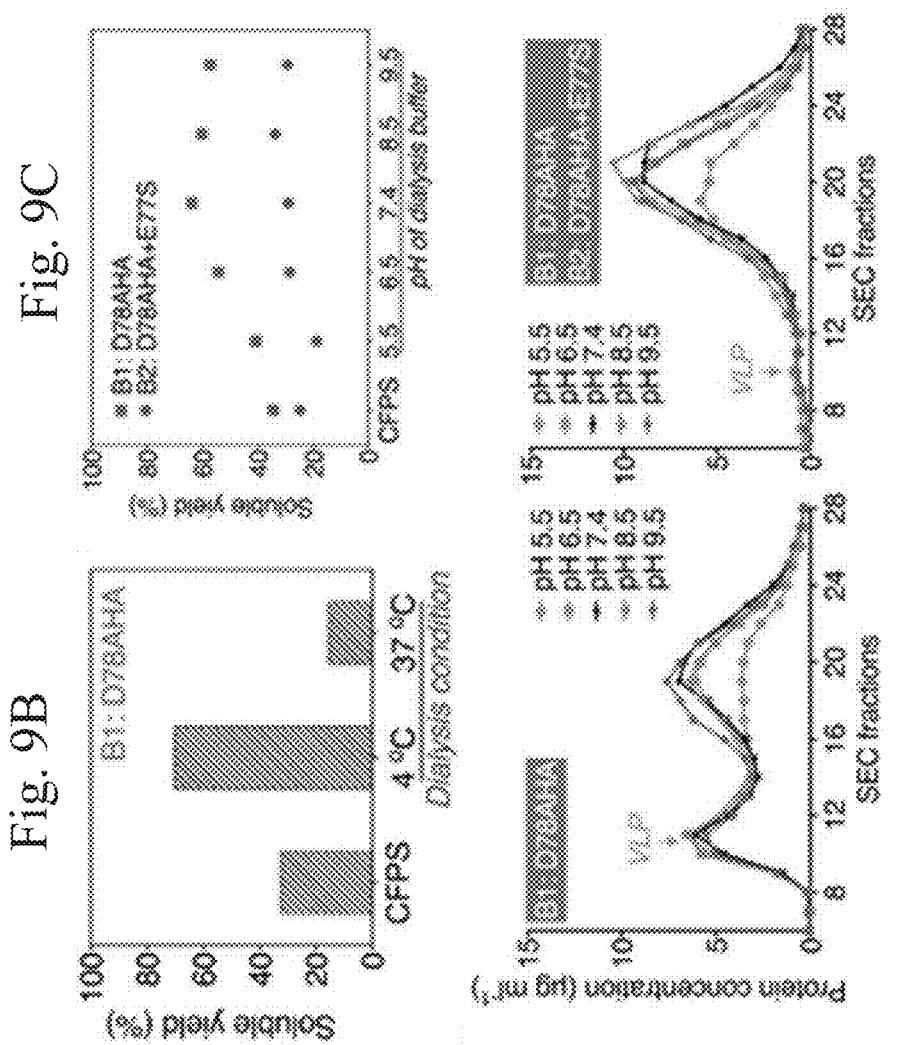
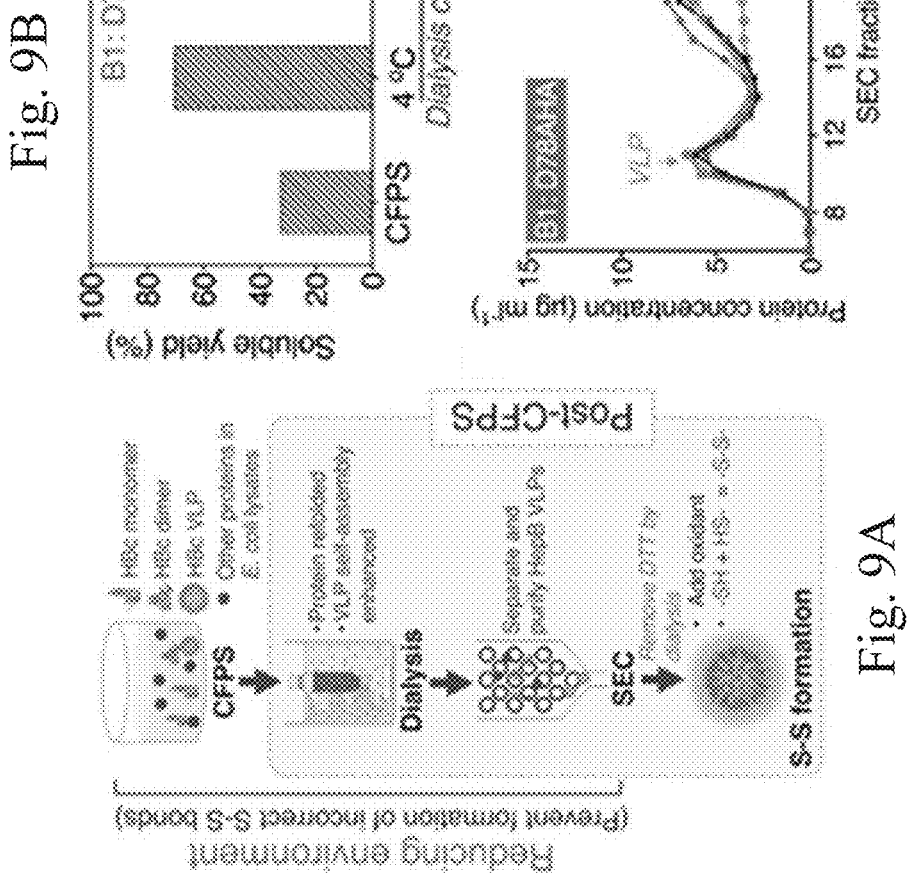
Fig. 9A Fig. 9B Fig. 9C Fig. 9D

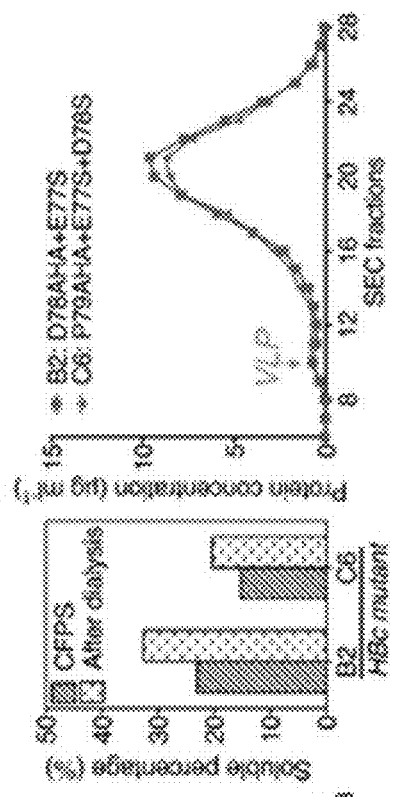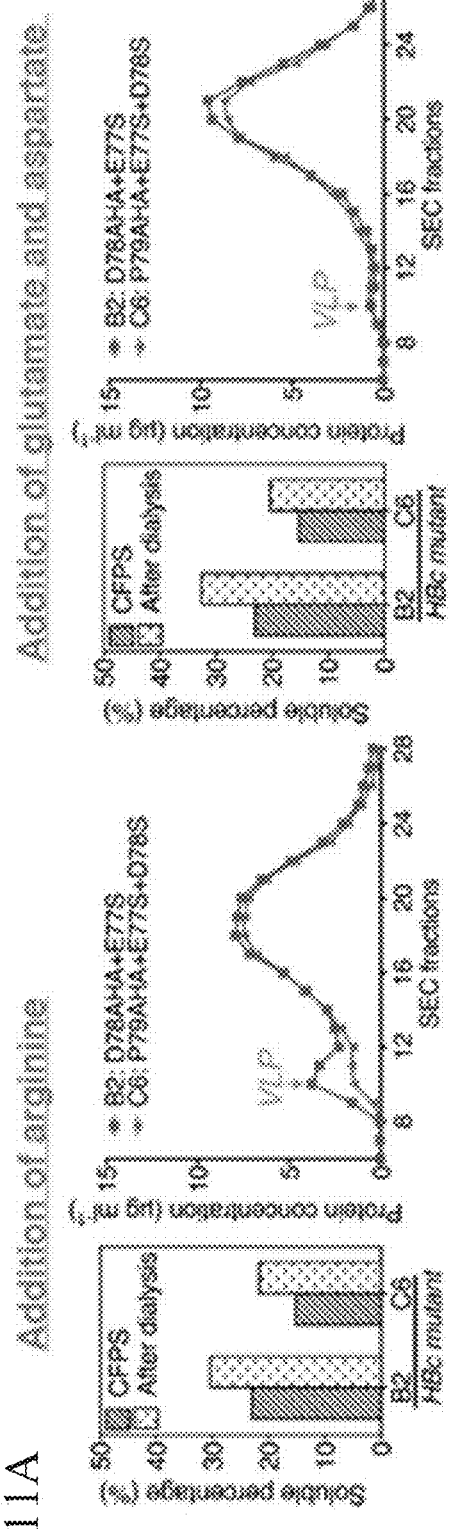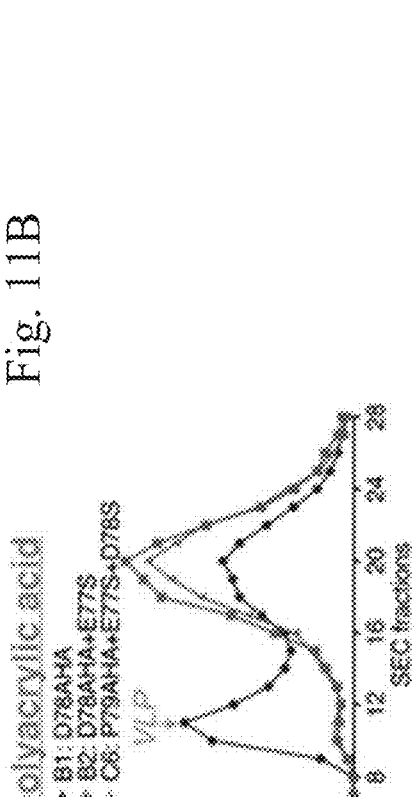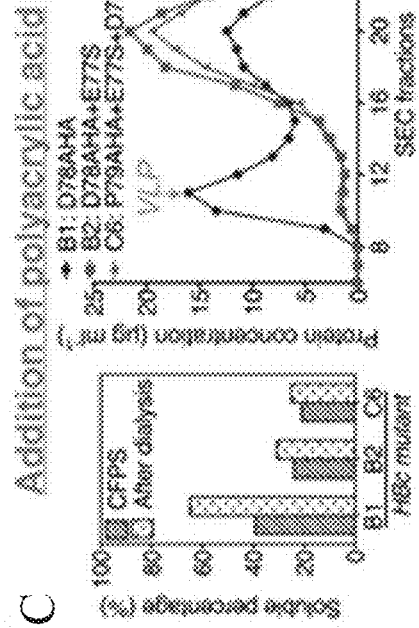
Fig. 11A Addition of arginine
Fig. 11B Addition of glutamate and aspartate
Fig. 11C Addition of polyacrylic acid

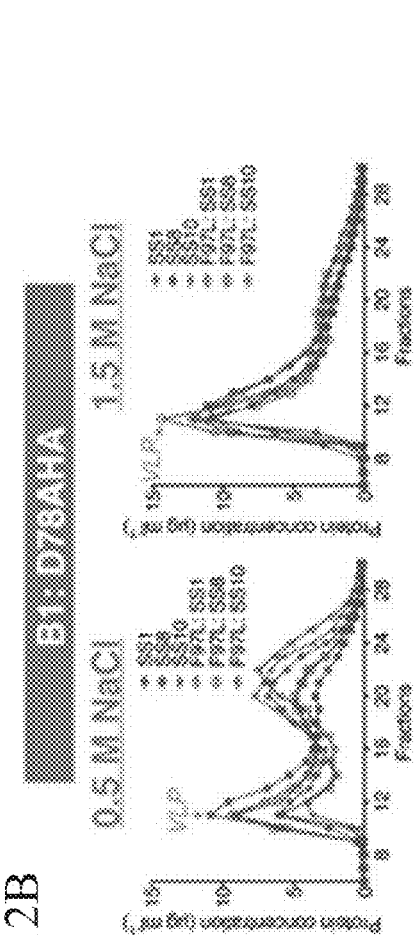
Fig. 12A
Fig. 12B
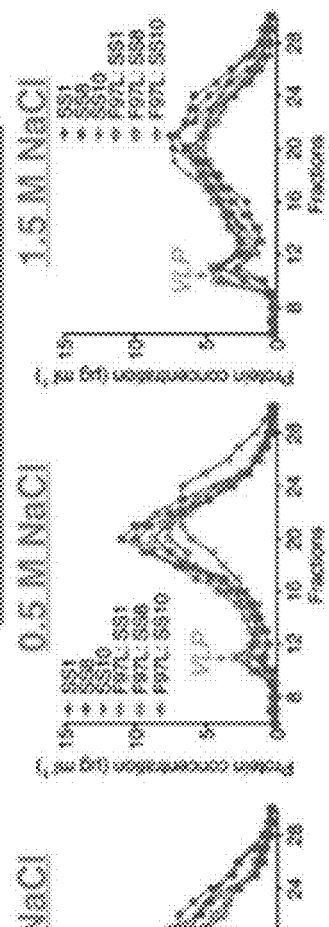
Fig. 12C
Fig. 12D

Fig. 14B

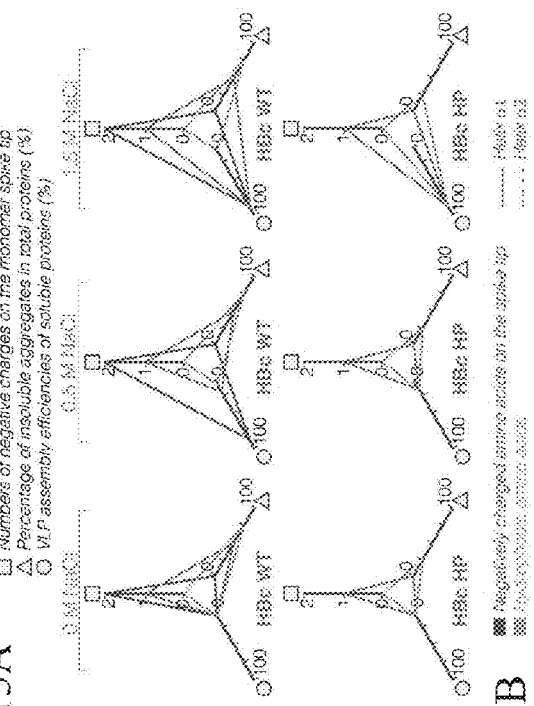
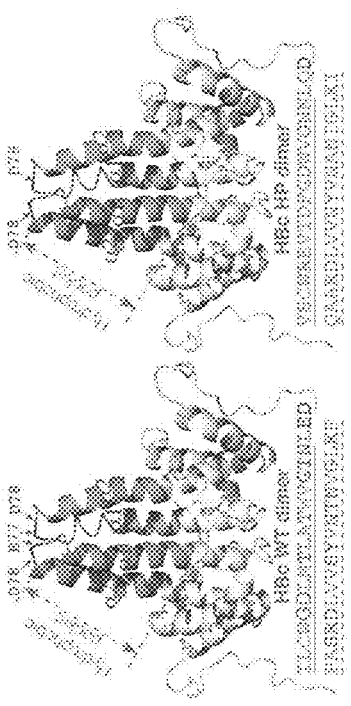
Fig. 15A
Fig. 15B

Figure 17. (A) A representative Ni-NTA column purification profile from one of the triplicate runs. (B) Reduced SDS Page gel - Comparing SEC purified assembled VLP and purified monomers.

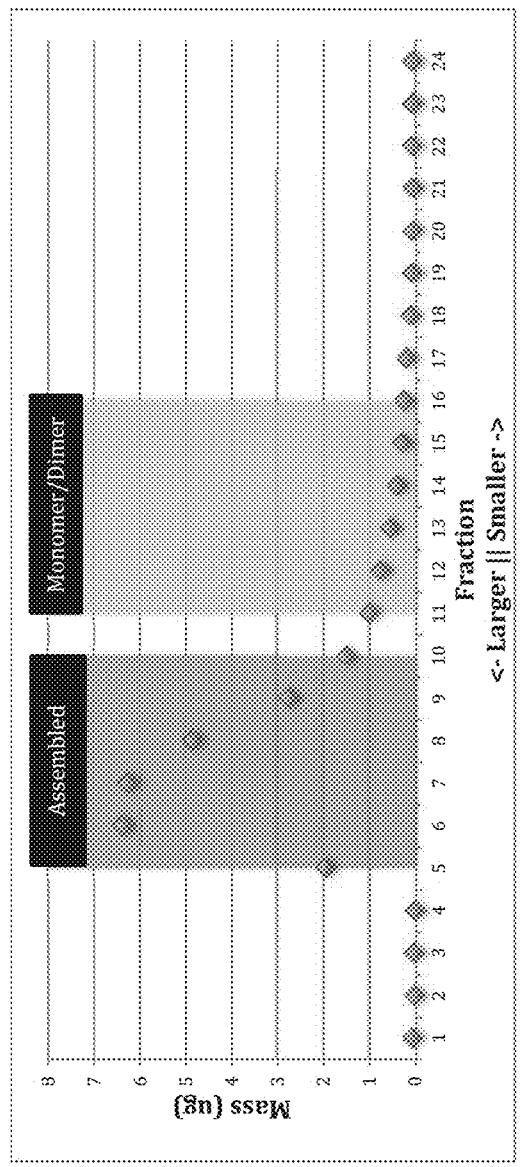

Figure 19. Representative Sucrose Gradient Sedimentation fractions from one of the triplicate runs.

SEQUENCE LISTING

<160> NUMBER OF SEQ ID NOS: 118

<210> SEQ ID NO 1
<211> LENGTH: 149
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 2
<211> LENGTH: 149
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
    130                 135                 140

Glu Thr Thr Val Val
145

```
<210> SEQ ID NO 3
<211> LENGTH: 149
<212> TYPE: PRT
<213> ORGANISM: Hepatitis B virus

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 4
<211> LENGTH: 149
<212> TYPE: PRT
<213> ORGANISM: Hepatitis B virus

<400> SEQUENCE: 4

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Cys Phe Gly Arg
            100                 105                 110

Glu Thr Val Leu Glu Tyr Leu Cys Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 5
<211> LENGTH: 149
<212> TYPE: PRT
```

<213> ORGANISM: Hepatitis B virus

<400> SEQUENCE: 5

Met Asp Ile Asp Pro Tyr Lys Glu Phe Gly Ala Thr Val Glu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Cys Arg Pro Cys Ala Pro Ile Leu Ser Thr Leu Pro
    130                 135                 140

Glu Thr Thr Val Val
145

<210> SEQ ID NO 6
<211> LENGTH: 149
<212> TYPE: PRT
<213> ORGANISM: Hepatitis B virus

<400> SEQUENCE: 6

Met Asp Ile Asp Pro Tyr Lys Glu Phe Gly Ala Thr Val Glu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Cys Arg Pro Asn Cys Pro Ile Leu Ser Thr Leu Pro
    130                 135                 140

Glu Thr Thr Val Val
145

<210> SEQ ID NO 7
<211> LENGTH: 149
<212> TYPE: PRT
<213> ORGANISM: Hepatitis B virus

<400> SEQUENCE: 7

```
Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
                20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Cys Pro Pro Cys Ala Pro Ile Leu Ser Thr Leu Pro
    130                 135                 140

Glu Thr Thr Val Val
145

<210> SEQ ID NO 8
<211> LENGTH: 149
<212> TYPE: PRT
<213> ORGANISM: Hepatitis B virus

<400> SEQUENCE: 8

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Asp Leu Leu Asp
                20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Cys Pro Pro Asn Cys Pro Ile Leu Ser Thr Leu Pro
    130                 135                 140

Glu Thr Thr Val Val
145

<210> SEQ ID NO 9
<211> LENGTH: 149
<212> TYPE: PRT
<213> ORGANISM: Hepatitis B virus

<400> SEQUENCE: 9

Met Asp Ile Asp Pro Tyr Lys Glu Phe Gly Ala Thr Val Glu Leu Leu
1               5                   10                  15
```

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Cys Cys Asn Ala Pro Ile Leu Ser Thr Leu Pro
    130                 135                 140

Glu Thr Thr Val Val
145

<210> SEQ ID NO 10
<211> LENGTH: 149
<212> TYPE: PRT
<213> ORGANISM: Hepatitis B virus

<400> SEQUENCE: 10

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Cys Pro Cys Ala Pro Ile Leu Ser Thr Leu Pro
    130                 135                 140

Glu Thr Thr Val Val
145

<210> SEQ ID NO 11
<211> LENGTH: 149
<212> TYPE: PRT
<213> ORGANISM: Hepatitis B virus

<400> SEQUENCE: 11

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

```
Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Cys Pro Asn Cys Pro Ile Leu Ser Thr Leu Pro
        130                 135                 140

Glu Thr Thr Val Val
145

<210> SEQ ID NO 12
<211> LENGTH: 149
<212> TYPE: PRT
<213> ORGANISM: Hepatitis B virus

<400> SEQUENCE: 12

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Ser Thr Leu Ala Thr Trp Val Gly Thr Asn Met Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
            115                 120                 125

Pro Pro Ala Tyr Arg Pro Cys Cys Ala Pro Ile Leu Ser Thr Leu Pro
        130                 135                 140

Glu Thr Thr Val Val
145

<210> SEQ ID NO 13
<211> LENGTH: 149
<212> TYPE: PRT
<213> ORGANISM: Hepatitis B virus
<220> FEATURE:
<221> NAME/KEY: VARIANT
<222> LOCATION: (76)..(76)
<223> OTHER INFORMATION: Xaa = Azidohomoalanine

<400> SEQUENCE: 13

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
```

```
            20                  25                  30
Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Xaa Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 14
<211> LENGTH: 149
<212> TYPE: PRT
<213> ORGANISM: Hepatitis B virus
<220> FEATURE:
<221> NAME/KEY: VARIANT
<222> LOCATION: (76)..(76)
<223> OTHER INFORMATION: Xaa = Azidohomoalanine

<400> SEQUENCE: 14

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Xaa Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 15
<211> LENGTH: 149
<212> TYPE: PRT
<213> ORGANISM: Hepatitis B virus
<220> FEATURE:
<221> NAME/KEY: VARIANT
<222> LOCATION: (74)..(74)
<223> OTHER INFORMATION: Xaa = Azidohomoalanine

<400> SEQUENCE: 15
```

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Xaa Asn Leu Glu Asp Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 16
<211> LENGTH: 149
<212> TYPE: PRT
<213> ORGANISM: Hepatitis B virus
<220> FEATURE:
<221> NAME/KEY: VARIANT
<222> LOCATION: (78)..(78)
<223> OTHER INFORMATION: Xaa = Azidohomoalanine

<400> SEQUENCE: 16

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Glu Xaa Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 17
<211> LENGTH: 149
<212> TYPE: PRT
<213> ORGANISM: Hepatitis B virus
<220> FEATURE:
```

<221> NAME/KEY: VARIANT
<222> LOCATION: (78)..(78)
<223> OTHER INFORMATION: Xaa = Azidohomoalanine

<400> SEQUENCE: 17

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Ser Xaa Pro Ala
65                  70                  75                  80

Ser Arg Asp Leu Val Val Ser Tyr Val Asn Thr Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
                115                 120                 125

Pro Pro Ala Tyr Arg Pro Pro Asn Ala Pro Ile Leu Ser Thr Leu Pro
            130                 135                 140

Glu Thr Thr Val Val
145
```

<210> SEQ ID NO 18
<211> LENGTH: 149
<212> TYPE: PRT
<213> ORGANISM: Hepatitis B virus
<220> FEATURE:
<221> NAME/KEY: VARIANT
<222> LOCATION: (78)..(78)
<223> OTHER INFORMATION: Xaa = Azidohomoalanine

<400> SEQUENCE: 18

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Ser Glu Xaa Pro Ala
65                  70                  75                  80

Ser Arg Asp Leu Val Val Ser Tyr Val Asn Thr Val Gly Leu Lys
                85                  90                  95

Phe Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
                115                 120                 125

Pro Pro Ala Tyr Arg Pro Pro Asn Ala Pro Ile Leu Ser Thr Leu Pro
            130                 135                 140

Glu Thr Thr Val Val
145
```

<210> SEQ ID NO 19
<211> LENGTH: 149
<212> TYPE: PRT
<213> ORGANISM: Hepatitis B virus
<220> FEATURE:
<221> NAME/KEY: VARIANT
<222> LOCATION: (78)..(78)
<223> OTHER INFORMATION: Xaa = Azidohomoalanine

<400> SEQUENCE: 19

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Ser Ala Xaa Pro Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 20
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 20

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Glu Asp Xaa Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

```
Glu Thr Thr Val Val
145

<210> SEQ ID NO 21
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 21

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Lys Asp Xaa Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 22
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 22

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Glu Lys Xaa Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110
```

```
Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 23
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 23

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Ser Asp Xaa Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 24
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 24

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Glu Ser Xaa Ala
65                  70                  75                  80

Ser Arg Asp Leu Val Val Ser Tyr Val Asn Thr Asn Val Gly Leu Lys
```

```
                    85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125

Pro Pro Ala Tyr Arg Pro Asn Ala Pro Ile Leu Ser Thr Leu Pro
        130                 135                 140

Glu Thr Thr Val Val
145

<210> SEQ ID NO 25
<211> LENGTH: 149
<212> TYPE: PRT
<213> ORGANISM: Hepatitis B virus
<220> FEATURE:
<221> NAME/KEY: VARIANT
<222> LOCATION: (79)..(79)
<223> OTHER INFORMATION: Xaa = Azidohomoalanine

<400> SEQUENCE: 25

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Ser Ser Xaa Ala
65                  70                  75                  80

Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125

Pro Pro Ala Tyr Arg Pro Asn Ala Pro Ile Leu Ser Thr Leu Pro
        130                 135                 140

Glu Thr Thr Val Val
145

<210> SEQ ID NO 26
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 26

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60
```

```
Leu Ser Thr Leu Ala Thr Trp Val Gly Thr Asn Leu Glu Asp Pro Xaa
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 27
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 27

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Lys Asp Pro Xaa
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 28
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 28

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30
```

```
Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
 50                  55                  60

Leu Ser Thr Leu Ala Thr Trp Val Gly Thr Asn Leu Glu Lys Pro Xaa
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
             100                 105                 110

Glu Thr Val Leu Glu Tyr Leu Val Ser Phe Gly Val Trp Ile Cys Thr
         115                 120                 125

Pro Pro Ala Tyr Arg Pro Pro Asn Ala Pro Ile Leu Ser Thr Leu Pro
     130                 135                 140

Glu Thr Thr Val Val
145

<210> SEQ ID NO 29
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 29

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Cys Leu Leu Asp
                 20                  25                  30

Thr Ala Ala Ala Leu Tyr Arg Asp Ala Leu Glu Ser Pro Glu His Cys
             35                  40                  45

Ser Pro His His Thr Ala Leu Arg Gln Ala Ile Leu Cys Trp Gly Asp
 50                  55                  60

Leu Ser Thr Leu Ala Thr Trp Val Gly Thr Asn Leu Ser Asp Pro Xaa
 65                  70                  75                  80

Ser Arg Asp Leu Val Val Ser Tyr Val Asn Thr Asn Val Gly Leu Lys
                 85                  90                  95

Phe Arg Gln Leu Leu Trp Phe His Ile Ser Cys Leu Thr Phe Gly Arg
             100                 105                 110

Glu Thr Val Leu Glu Tyr Leu Val Ser Phe Gly Val Trp Ile Cys Thr
         115                 120                 125

Pro Pro Ala Tyr Arg Pro Pro Asn Ala Pro Ile Leu Ser Thr Leu Pro
     130                 135                 140

Glu Thr Thr Val Val
145

<210> SEQ ID NO 30
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 30

Met Asp Ile Asp Pro Tyr Lys Glu Phe Gly Ala Thr Val Glu Leu Leu
```

```
                1               5                  10                 15
Ser Phe Leu Pro Ser Asp Phe Phe Pro Ser Val Arg Cys Leu Leu Asp
                20                 25                 30

Thr Ala Ala Ala Leu Tyr Arg Asp Ala Leu Glu Ser Pro Glu His Cys
                35                 40                 45

Ser Pro His His Thr Ala Leu Arg Gln Ala Ile Leu Cys Trp Gly Asp
        50                 55                 60

Leu Ser Thr Leu Ala Thr Trp Val Gly Thr Asn Leu Glu Ser Pro Xaa
65                  70                 75                  80

Ser Arg Asp Leu Val Val Ser Tyr Val Asn Thr Asn Val Gly Leu Lys
                85                 90                 95

Phe Arg Gln Leu Leu Trp Phe His Ile Ser Cys Leu Thr Phe Gly Arg
                100                105                110

Glu Thr Val Leu Glu Tyr Leu Val Ser Phe Gly Val Trp Ile Cys Thr
                115                120                125

Pro Pro Ala Tyr Arg Pro Pro Asn Ala Pro Ile Leu Ser Thr Leu Pro
                130                135                140

Glu Thr Thr Val Val
145
```

<210> SEQ ID NO 31
<211> LENGTH: 149
<212> TYPE: PRT
<213> ORGANISM: Hepatitis B virus
<220> FEATURE:
<221> NAME/KEY: VARIANT
<222> LOCATION: (80)..(80)
<223> OTHER INFORMATION: Xaa = Azidohomoalanine

<400> SEQUENCE: 31

```
Met Asp Ile Asp Pro Tyr Lys Glu Phe Gly Ala Thr Val Glu Leu Leu
1               5                  10                 15

Ser Phe Leu Pro Ser Asp Phe Phe Pro Ser Val Arg Cys Leu Leu Asp
                20                 25                 30

Thr Ala Ala Ala Leu Tyr Arg Asp Ala Leu Glu Ser Pro Glu His Cys
                35                 40                 45

Ser Pro His His Thr Ala Leu Arg Gln Ala Ile Leu Cys Trp Gly Asp
        50                 55                 60

Leu Ser Thr Leu Ala Thr Trp Val Gly Thr Asn Leu Ser Ser Pro Xaa
65                  70                 75                  80

Ser Arg Asp Leu Val Val Ser Tyr Val Asn Thr Asn Val Gly Leu Lys
                85                 90                 95

Phe Arg Gln Leu Leu Trp Phe His Ile Ser Cys Leu Thr Phe Gly Arg
                100                105                110

Glu Thr Val Leu Glu Tyr Leu Val Ser Phe Gly Val Trp Ile Cys Thr
                115                120                125

Pro Pro Ala Tyr Arg Pro Pro Asn Ala Pro Ile Leu Ser Thr Leu Pro
                130                135                140

Glu Thr Thr Val Val
145
```

<210> SEQ ID NO 32
<211> LENGTH: 149
<212> TYPE: PRT
<213> ORGANISM: Hepatitis B virus

<400> SEQUENCE: 32

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Pro Ala
65                  70                  75                  80

Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 33
<211> LENGTH: 149
<212> TYPE: PRT
<213> ORGANISM: Hepatitis B virus

<400> SEQUENCE: 33

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
    50                  55                  60

Leu Ser Thr Leu Ala Thr Trp Val Gly Thr Asn Leu Glu Met Pro Ala
65                  70                  75                  80

Ser Arg Asp Leu Val Val Ser Tyr Val Asn Thr Asn Val Gly Leu Lys
            85                  90                  95

Phe Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 34
<211> LENGTH: 148
<212> TYPE: PRT
<213> ORGANISM: Hepatitis B virus

<400> SEQUENCE: 34

Asp Ile Asp Pro Tyr Lys Glu Phe Gly Ala Thr Val Glu Leu Leu Ser
1               5                   10                  15

```
Phe Leu Pro Ser Asp Phe Pro Ser Val Arg Cys Leu Leu Asp Thr
            20                  25                  30

Ala Ala Ala Leu Tyr Arg Asp Ala Leu Glu Ser Pro Glu His Cys Ser
        35                  40                  45

Pro His His Thr Ala Leu Arg Gln Ala Ile Leu Cys Trp Gly Asp Leu
    50                  55                  60

Ser Thr Leu Ala Thr Trp Val Gly Asn Asn Met Gln Asp Gln Ala Ala
65                  70                  75                  80

Arg Asp Leu Val Val Ser Tyr Val Asn Thr Asn Val Gly Leu Lys Phe
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Cys Thr Pro
        115                 120                 125

Pro Ala Tyr Arg Pro Pro Asn Ala Pro Ile Leu Ser Thr Leu Pro Glu
    130                 135                 140

Thr Thr Val Val
145

<210> SEQ ID NO 35
<211> LENGTH: 149
<212> TYPE: PRT
<213> ORGANISM: Hepatitis B virus

<400> SEQUENCE: 35

Met Asp Ile Asp Pro Tyr Lys Glu Phe Gly Ala Thr Val Glu Leu Leu
1               5                   10                  15

Ser Phe Leu Pro Ser Asp Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Met Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 36
<211> LENGTH: 149
<212> TYPE: PRT
<213> ORGANISM: Hepatitis B virus
<220> FEATURE:
<221> NAME/KEY: VARIANT
<222> LOCATION: (1)..(75)
<223> OTHER INFORMATION: Xaa = Azidohomoalanine

<400> SEQUENCE: 36

Xaa Asp Ile Asp Pro Tyr Lys Glu Phe Gly Ala Thr Val Glu Leu Leu
1               5                   10                  15
```

Ser Phe Leu Pro Ser Asp Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Xaa Leu Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 37
<211> LENGTH: 149
<212> TYPE: PRT
<213> ORGANISM: Hepatitis B virus
<220> FEATURE:
<221> NAME/KEY: VARIANT
<222> LOCATION: (1)..(76)
<223> OTHER INFORMATION: Xaa = Azidohomoalanine

<400> SEQUENCE: 37

Xaa Asp Ile Asp Pro Tyr Lys Glu Phe Gly Ala Thr Val Glu Leu Leu
1               5                   10                  15

Ser Phe Leu Pro Ser Asp Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Xaa Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 38
<211> LENGTH: 149
<212> TYPE: PRT
<213> ORGANISM: Hepatitis B virus
<220> FEATURE:
<221> NAME/KEY: VARIANT
<222> LOCATION: (1)..(77)
<223> OTHER INFORMATION: Xaa = Azidohomoalanine

<400> SEQUENCE: 38

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Xaa Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 39
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 39

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Cys Thr
            115                 120                 125

Pro Pro Ala Tyr Arg Pro Pro Asn Ala Pro Ile Leu Ser Thr Leu Pro
        130                 135                 140

Glu Thr Thr Val Val
145

<210> SEQ ID NO 40
<211> LENGTH: 149
<212> TYPE: PRT

```
<213> ORGANISM: Hepatitis B virus
<220> FEATURE:
<221> NAME/KEY: VARIANT
<222> LOCATION: (1)..(79)
<223> OTHER INFORMATION: Xaa = Azidohomoalanine

<400> SEQUENCE: 40

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Asp Xaa Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 41
<211> LENGTH: 149
<212> TYPE: PRT
<213> ORGANISM: Hepatitis B virus
<220> FEATURE:
<221> NAME/KEY: VARIANT
<222> LOCATION: (1)..(80)
<223> OTHER INFORMATION: Xaa = Azidohomoalanine

<400> SEQUENCE: 41

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Asp Gln Xaa
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145
```

<210> SEQ ID NO 42
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 42

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 43
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 43

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Cys Phe Gly Arg
            100                 105                 110

Glu Thr Val Leu Glu Tyr Leu Cys Ser Phe Gly Val Trp Ile Arg Thr
        115                 120                 125

```
Pro Pro Ala Tyr Arg Pro Pro Asn Ala Pro Ile Leu Ser Thr Leu Pro
        130                 135                 140

Glu Thr Thr Val Val
145

<210> SEQ ID NO 44
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 44

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Cys Arg Pro Pro Cys Ala Pro Ile Leu Ser Thr Leu Pro
    130                 135                 140

Glu Thr Thr Val Val
145

<210> SEQ ID NO 45
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 45

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
```

-continued

```
                100                 105                 110
Glu Thr Val Leu Glu Tyr Leu Val Ser Phe Gly Val Trp Ile Arg Thr
            115                 120                 125

Pro Pro Ala Cys Arg Pro Pro Asn Cys Pro Ile Leu Ser Thr Leu Pro
            130                 135                 140

Glu Thr Thr Val Val
145

<210> SEQ ID NO 46
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 46

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
            115                 120                 125

Pro Pro Ala Tyr Cys Pro Pro Cys Ala Pro Ile Leu Ser Thr Leu Pro
            130                 135                 140

Glu Thr Thr Val Val
145

<210> SEQ ID NO 47
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 47

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80
```

-continued

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Cys Pro Pro Asn Cys Pro Ile Leu Ser Thr Leu Pro
    130                 135                 140

Glu Thr Thr Val Val
145

<210> SEQ ID NO 48
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 48

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Cys Cys Asn Ala Pro Ile Leu Ser Thr Leu Pro
    130                 135                 140

Glu Thr Thr Val Val
145

<210> SEQ ID NO 49
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 49

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Cys Pro Cys Ala Pro Ile Leu Ser Thr Leu Pro
    130                 135                 140

Glu Thr Thr Val Val
145

<210> SEQ ID NO 50
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 50

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
                100                 105                 110

Glu Thr Val Leu Glu Tyr Leu Val Ser Phe Gly Val Trp Ile Arg Thr
                115                 120                 125

Pro Pro Ala Tyr Arg Cys Pro Asn Cys Pro Ile Leu Ser Thr Leu Pro
    130                 135                 140

Glu Thr Thr Val Val
145

<210> SEQ ID NO 51
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 51

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp

```
                20                  25                  30

Thr Ala Ala Leu Tyr Arg Asp Ala Leu Glu Ser Pro Glu His Cys
            35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Cys Cys Ala Pro Ile Leu Ser Thr Leu Pro
    130                 135                 140

Glu Thr Thr Val Val
145

<210> SEQ ID NO 52
<211> LENGTH: 149
<212> TYPE: PRT
<213> ORGANISM: Hepatitis B virus
<220> FEATURE:
<221> NAME/KEY: VARIANT
<222> LOCATION: (1)..(78)
<223> OTHER INFORMATION: Xaa = Azidohomoalanine

<400> SEQUENCE: 52

Xaa Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Cys Leu Leu Asp
            20                  25                  30

Thr Ala Ala Leu Tyr Arg Asp Ala Leu Glu Ser Pro Glu His Cys
            35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Xaa Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Cys Thr
        115                 120                 125

Pro Pro Ala Tyr Arg Cys Pro Cys Ala Pro Ile Leu Ser Thr Leu Pro
    130                 135                 140

Glu Thr Thr Val Val
145

<210> SEQ ID NO 53
<211> LENGTH: 453
<212> TYPE: DNA
<213> ORGANISM: Hepatitis B virus

<400> SEQUENCE: 53
atggatatcg accgtacaa agaattcggc gcgaccgttg aactgctgtc tttcctgccg      60
tctgatttct tcccgtctgt tcgtgacctg ctggacaccg cggcagcact gtaccgtgac     120
```

```
gcgctggaat ctccggaaca ttgttctccg catcacactg cgctgcgtca ggcgattctg    180
tgctggggcg acctgatgac cctggcgact tgggttggca ccaacctgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttaccgtc cgccgaacgc accgatcctg    420
agcaccctgc cggaaaccac tgttgtgtaa taa                                 453
```

<210> SEQ ID NO 54
<211> LENGTH: 453
<212> TYPE: DNA
<213> ORGANISM: Hepatitis B virus

<400> SEQUENCE: 54

```
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttaccgtc cgccgaacgc accgatcctg    420
agcaccctgc cggaaaccac tgttgtgtaa taa                                 453
```

<210> SEQ ID NO 55
<211> LENGTH: 453
<212> TYPE: DNA
<213> ORGANISM: Hepatitis B virus

<400> SEQUENCE: 55

```
atggatatcg acccgtacaa agaattcggc gcgaccgttg aactgctgtc tttcctgccg     60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453
```

<210> SEQ ID NO 56
<211> LENGTH: 453
<212> TYPE: DNA
<213> ORGANISM: Hepatitis B virus

<400> SEQUENCE: 56

```
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
```

```
ctgtggttcc acatctcttg cctgtgcttc ggtcgtgaaa ccgttctgga atacctgtgt    360
tcttttggtg tttggattcg tactccgccg gcttaccgtc cgccgaacgc accgatcctg    420
agcaccctgc cggaaaccac tgttgtgtaa taa                                 453

<210> SEQ ID NO 57
<211> LENGTH: 453
<212> TYPE: DNA
<213> ORGANISM: Hepatitis B virus

<400> SEQUENCE: 57
atggatatcg acccgtacaa agaattcggc gcgaccgttg aactgctgtc tttcctgccg     60
tctgatttct cccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttgccgtc cgccgtgcgc accgatcctg    420
agcaccctgc cggaaaccac tgttgtgtaa taa                                 453

<210> SEQ ID NO 58
<211> LENGTH: 453
<212> TYPE: DNA
<213> ORGANISM: Hepatitis B virus

<400> SEQUENCE: 58
atggatatcg acccgtacaa agaattcggc gcgaccgttg aactgctgtc tttcctgccg     60
tctgatttct cccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttgccgtc cgccgaactg cccgatcctg    420
agcaccctgc cggaaaccac tgttgtgtaa taa                                 453

<210> SEQ ID NO 59
<211> LENGTH: 453
<212> TYPE: DNA
<213> ORGANISM: Hepatitis B virus

<400> SEQUENCE: 59
atggatatcg acccgtacaa agaattcggc gcgaccgttg aactgctgtc tttcctgccg     60
tctgatttct cccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacatgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttactgcc cgccgtgcgc accgatcctg    420
agcaccctgc cggaaaccac tgtt

<210> SEQ ID NO 60
<211> LENGTH: 453
<212> TYPE: DNA
<213> ORGANISM: Hepatitis B virus

<400> SEQUENCE: 60

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcgattctg     180
tgctggggcg acctgagcac cctggcgact tgggttggca ccaacatgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga atacctggtt     360
tcttttggtg tttggattcg tactccgccg gcttactgcc cgccgaactg cccgatcctg     420
agcaccctgc cggaaaccac tgttgtgtaa taa                                  453
```

<210> SEQ ID NO 61
<211> LENGTH: 453
<212> TYPE: DNA
<213> ORGANISM: Hepatitis B virus

<400> SEQUENCE: 61

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcgattctg     180
tgctggggcg acctgagcac cctggcgact tgggttggca ccaacatgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga atacctggtt     360
tcttttggtg tttggattcg tactccgccg gcttaccgtt gctgcaacgc accgatcctg     420
agcaccctgc cggaaaccac tgttgtgtaa taa                                  453
```

<210> SEQ ID NO 62
<211> LENGTH: 453
<212> TYPE: DNA
<213> ORGANISM: Hepatitis B virus

<400> SEQUENCE: 62

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcgattctg     180
tgctggggcg acctgagcac cctggcgact tgggttggca ccaacatgga agatccggcg     240
tctcgtgatc tggttgtttc ttacgttaac actaacgttg gtctgaaatt ccgtcagctg     300
ctgtggttcc acatctcttg cctgaccttc ggtcgtgaaa ccgttctgga atacctggtt     360
tcttttggtg tttggattcg tactccgccg gcttaccgtt gcccgtgcgc accgatcctg     420
agcaccctgc cggaaaccac tgttgtgtaa taa                                  453
```

<210> SEQ ID NO 63
<211> LENGTH: 453
<212> TYPE: DNA
<213> ORGANISM: Hepatitis B virus

<400> SEQUENCE: 63

```
atggatatcg acccgtacaa agaattcggc gcgaccgttg aactgctgtc tttcctgccg    60
tctgatttct tcccgtctgt tcgtgacctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacatgga agatccggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggattcg tactccgccg gcttaccgtt gcccgaactg cccgatcctg   420
agcaccctgc cggaaaccac tgttgtgtaa taa                                453
```

<210> SEQ ID NO 64
<211> LENGTH: 453
<212> TYPE: DNA
<213> ORGANISM: Hepatitis B virus

<400> SEQUENCE: 64

```
atggatatcg acccgtacaa agaattcggc gcgaccgttg aactgctgtc tttcctgccg    60
tctgatttct tcccgtctgt tcgtgacctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacatgga agatccggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggattcg tactccgccg gcttaccgtc gtgctgcgc accgatcctg    420
agcaccctgc cggaaaccac tgttgtgtaa taa                                453
```

<210> SEQ ID NO 65
<211> LENGTH: 453
<212> TYPE: DNA
<213> ORGANISM: Hepatitis B virus

<400> SEQUENCE: 65

```
atggatatcg acccgtacaa agaattcggc gcgaccgttg aactgctgtc tttcctgccg    60
tctgatttct tcccgtctgt tcgtgacctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacatgga agatccggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggattcg tactccgccg gcttaccgtc gcccgaacgc accgatcctg   420
agcaccctgc cggaaaccac tgttgtgtaa taa                                453
```

<210> SEQ ID NO 66
<211> LENGTH: 453
<212> TYPE: DNA
<213> ORGANISM: Hepatitis B virus

<400> SEQUENCE: 66

```
atggatatcg acccgtacaa agaattcggc gcgaccgttg aactgctgtc tttcctgccg    60
tctgatttct tcccgtctgt tcgttgcctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacatgga agatccggcg   240
```

```
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 67
<211> LENGTH: 453
<212> TYPE: DNA
<213> ORGANISM: Hepatitis B virus

<400> SEQUENCE: 67

```
atggatatcg acccgtacaa agaattcggc gcgaccgttg aactgctgtc tttcctgccg       60
tctgatttct cccgtctgt tcgttgcctg ctggacaccg cggcagcact gtaccgtgac       120
gcgctggaat ctccggaaca ttgttctccg catcacactg cgctgcgtca ggcgattctg      180
tgctggggcg acctgagcac cctggcgact tgggttggca tgaacctgga agatccggcg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 68
<211> LENGTH: 453
<212> TYPE: DNA
<213> ORGANISM: Hepatitis B virus

<400> SEQUENCE: 68

```
atggatatcg acccgtacaa agaattcggc gcgaccgttg aactgctgtc tttcctgccg       60
tctgatttct cccgtctgt tcgttgcctg ctggacaccg cggcagcact gtaccgtgac       120
gcgctggaat ctccggaaca ttgttctccg catcacactg cgctgcgtca ggcgattctg      180
tgctggggcg acctgagcac cctggcgact tgggttggca ccaacctgga aatgccggcg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 69
<211> LENGTH: 453
<212> TYPE: DNA
<213> ORGANISM: Hepatitis B virus

<400> SEQUENCE: 69

```
atggatatcg acccgtacaa agaattcggc gcgaccgttg aactgctgtc tttcctgccg       60
tctgatttct cccgtctgt tcgttgcctg ctggacaccg cggcagcact gtaccgtgac       120
gcgctggaat ctccggaaca ttgttctccg catcacactg cgctgcgtca ggcgattctg      180
tgctggggcg acctgagcac cctggcgact tgggttggca ccaacctgag catgccggcg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
```

```
agcaccctgc cggaaaccac tgttgtgtaa taa                                  453
```

<210> SEQ ID NO 70
<211> LENGTH: 453
<212> TYPE: DNA
<213> ORGANISM: Hepatitis B virus

<400> SEQUENCE: 70

```
atggatatcg acccgtacaa agaattcggc gcgaccgttg aactgctgtc tttcctgccg    60
tctgatttct tcccgtctgt tcgttgcctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacagcga aatgccggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggatttg tactccgccg gcttaccgtc cgccgaacgc accgatcctg   420
agcaccctgc cggaaaccac tgttgtgtaa taa                                453
```

<210> SEQ ID NO 71
<211> LENGTH: 453
<212> TYPE: DNA
<213> ORGANISM: Hepatitis B virus

<400> SEQUENCE: 71

```
atggatatcg acccgtacaa agaattcggc gcgaccgttg aactgctgtc tttcctgccg    60
tctgatttct tcccgtctgt tcgttgcctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacagcgc gatgccggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggatttg tactccgccg gcttaccgtc cgccgaacgc accgatcctg   420
agcaccctgc cggaaaccac tgttgtgtaa taa                                453
```

<210> SEQ ID NO 72
<211> LENGTH: 453
<212> TYPE: DNA
<213> ORGANISM: Hepatitis B virus

<400> SEQUENCE: 72

```
atggatatcg acccgtacaa agaattcggc gcgaccgttg aactgctgtc tttcctgccg    60
tctgatttct tcccgtctgt tcgttgcctg ctggacaccg cggcagcact gtaccgtgac   120
gcgctggaat ctccggaaca ttgttctccg catcacactg cgctgcgtca ggcgattctg   180
tgctggggcg acctgagcac cctggcgact tgggttggca ccaacctgga agatatggcg   240
tctcgtgatc tggttgtttc ttacgttaac actaacgttg gtctgaaatt ccgtcagctg   300
ctgtggttcc acatctcttg cctgaccttc ggtcgtgaaa ccgttctgga atacctggtt   360
tcttttggtg tttggatttg tactccgccg gcttaccgtc cgccgaacgc accgatcctg   420
agcaccctgc cggaaaccac tgttgtgtaa taa                                453
```

<210> SEQ ID NO 73
<211> LENGTH: 453
<212> TYPE: DNA
<213> ORGANISM: Hepatitis B virus

<400> SEQUENCE: 73

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgaa agatatggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453
```

<210> SEQ ID NO 74
<211> LENGTH: 453
<212> TYPE: DNA
<213> ORGANISM: Hepatitis B virus

<400> SEQUENCE: 74

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgga aaaaatggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453
```

<210> SEQ ID NO 75
<211> LENGTH: 453
<212> TYPE: DNA
<213> ORGANISM: Hepatitis B virus

<400> SEQUENCE: 75

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgag cgatatggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453
```

<210> SEQ ID NO 76
<211> LENGTH: 453
<212> TYPE: DNA
<213> ORGANISM: Hepatitis B virus

<400> SEQUENCE: 76

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac    120
```

```
gcgctggaat ctccggaaca ttgttctccg catcacactg cgctgcgtca ggcgattctg      180
tgctggggcg acctgagcac cctggcgact tgggttggca ccaacctgga aagcatggcg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                  453
```

<210> SEQ ID NO 77
<211> LENGTH: 453
<212> TYPE: DNA
<213> ORGANISM: Hepatitis B virus

<400> SEQUENCE: 77

```
atggatatcg acccgtacaa agaattcggc gcgaccgttg aactgctgtc tttcctgccg      60
tctgatttct cccgtctgt tcgttgcctg ctggacaccg cggcagcact gtaccgtgac      120
gcgctggaat ctccggaaca ttgttctccg catcacactg cgctgcgtca ggcgattctg      180
tgctggggcg acctgagcac cctggcgact tgggttggca ccaacctgag cagcatggcg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                  453
```

<210> SEQ ID NO 78
<211> LENGTH: 453
<212> TYPE: DNA
<213> ORGANISM: Hepatitis B virus

<400> SEQUENCE: 78

```
atggatatcg acccgtacaa agaattcggc gcgaccgttg aactgctgtc tttcctgccg      60
tctgatttct cccgtctgt tcgttgcctg ctggacaccg cggcagcact gtaccgtgac      120
gcgctggaat ctccggaaca ttgttctccg catcacactg cgctgcgtca ggcgattctg      180
tgctggggcg acctgagcac cctggcgact tgggttggca ccaacctgga agatccgatg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                  453
```

<210> SEQ ID NO 79
<211> LENGTH: 453
<212> TYPE: DNA
<213> ORGANISM: Hepatitis B virus

<400> SEQUENCE: 79

```
atggatatcg acccgtacaa agaattcggc gcgaccgttg aactgctgtc tttcctgccg      60
tctgatttct cccgtctgt tcgttgcctg ctggacaccg cggcagcact gtaccgtgac      120
gcgctggaat ctccggaaca ttgttctccg catcacactg cgctgcgtca ggcgattctg      180
tgctggggcg acctgagcac cctggcgact tgggttggca ccaacctgaa agatccgatg      240
tctcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
```

```
tcttttggtg tttggatttg tactccgccg gcttaccgtc cgccgaacgc accgatcctg    420
agcaccctgc cggaaaccac tgttgtgtaa taa                                 453

<210> SEQ ID NO 80
<211> LENGTH: 453
<212> TYPE: DNA
<213> ORGANISM: Hepatitis B virus

<400> SEQUENCE: 80
atggatatcg acccgtacaa agaattcggc gcgaccgttg aactgctgtc tttcctgccg    60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgga aaaaccgatg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453

<210> SEQ ID NO 81
<211> LENGTH: 453
<212> TYPE: DNA
<213> ORGANISM: Hepatitis B virus

<400> SEQUENCE: 81
atggatatcg acccgtacaa agaattcggc gcgaccgttg aactgctgtc tttcctgccg    60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgag cgatccgatg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453

<210> SEQ ID NO 82
<211> LENGTH: 453
<212> TYPE: DNA
<213> ORGANISM: Hepatitis B virus

<400> SEQUENCE: 82
atggatatcg acccgtacaa agaattcggc gcgaccgttg aactgctgtc tttcctgccg    60
tctgatttct tcccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgga aagcccgatg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453

<210> SEQ ID NO 83
```

```
<211> LENGTH: 453
<212> TYPE: DNA
<213> ORGANISM: Hepatitis B virus

<400> SEQUENCE: 83
atggatatcg acccgtacaa agaattcggc gcgaccgttg aactgctgtc tttcctgccg      60
tctgatttct ccccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgag cagcccgatg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453

<210> SEQ ID NO 84
<211> LENGTH: 453
<212> TYPE: DNA
<213> ORGANISM: Hepatitis B virus

<400> SEQUENCE: 84
atggatatcg acccgtacaa agaattcggc gcgaccgttg aactgctgtc tttcctgccg      60
tctgatttct ccccgtctgt tcgtgacctg ctggacaccg cggcagcact gtaccgtgac    120
gcgctggaat ctccggaaca ttgttctccg catcacactg cgctgcgtca ggcgattctg    180
tgctggggcg acctgatgac cctggcgact tgggttggca ccaacctgga agatccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggattcg tactccgccg gcttaccgtc cgccgaacgc accgatcctg    420
agcaccctgc cggaaaccac tgttgtgtaa taa                                 453

<210> SEQ ID NO 85
<211> LENGTH: 453
<212> TYPE: DNA
<213> ORGANISM: Hepatitis B virus

<400> SEQUENCE: 85
atggatatcg acccgtacaa agaattcggc gcgaccgttg aactgctgtc tttcctgccg      60
tctgatttct ccccgtctgt tcgttgcctg ctggacaccg cggcagcact gtaccgtgac    120
gcgctggaat ctccggaaca ttgttctccg catcacactg cgctgcgtca ggcgattctg    180
tgctggggcg acctgagcac cctggcgact tgggttggca ccaacctgga aatgccggcg    240
tctcgtgatc tggttgtttc ttacgttaac actaacgttg gtctgaaatt ccgtcagctg    300
ctgtggttcc acatctcttg cctgaccttc ggtcgtgaaa ccgttctgga atacctggtt    360
tcttttggtg tttggatttg tactccgccg gcttaccgtc cgccgaacgc accgatcctg    420
agcaccctgc cggaaaccac tgttgtgtaa taa                                 453

<210> SEQ ID NO 86
<211> LENGTH: 453
<212> TYPE: DNA
<213> ORGANISM: Hepatitis B virus

<400> SEQUENCE: 86
atggatatcg acccgtacaa agaattcggc gcgaccgttg aactgctgtc tttcctgccg      60
```

```
tctgatttct ccccgtctgt tcgttgcctg ctggacaccg cggcagcact gtaccgtgac      120
gcgctggaat ctccggaaca ttgttctccg catcacactg cgctgcgtca ggcgattctg      180
tgctggggcg acctgagcac cctggcgact tgggttggca acaacatgca ggatcaggcg      240
gcgcgtgatc tggttgtttc ttacgttaac actaacgttg gtctgaaatt ccgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                    453

<210> SEQ ID NO 87
<211> LENGTH: 453
<212> TYPE: DNA
<213> ORGANISM: Hepatitis B virus

<400> SEQUENCE: 87
atggatatcg acccgtacaa agaattcggc gcgaccgttg aactgctgtc tttcctgccg       60
tctgatttct ccccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acaacatgca ggatcaggcg      240
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                    453

<210> SEQ ID NO 88
<211> LENGTH: 453
<212> TYPE: DNA
<213> ORGANISM: Hepatitis B virus

<400> SEQUENCE: 88
atggatatcg acccgtacaa agaattcggc gcgaccgttg aactgctgtc tttcctgccg       60
tctgatttct ccccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acatgctgca ggatcaggcg      240
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                    453

<210> SEQ ID NO 89
<211> LENGTH: 453
<212> TYPE: DNA
<213> ORGANISM: Hepatitis B virus

<400> SEQUENCE: 89
atggatatcg acccgtacaa agaattcggc gcgaccgttg aactgctgtc tttcctgccg       60
tctgatttct ccccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acaacatgca ggatcaggcg      240
```

-continued

```
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 90
<211> LENGTH: 453
<212> TYPE: DNA
<213> ORGANISM: Hepatitis B virus

<400> SEQUENCE: 90

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acaacctgat ggatcaggcg      240
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 91
<211> LENGTH: 453
<212> TYPE: DNA
<213> ORGANISM: Hepatitis B virus

<400> SEQUENCE: 91

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acaacctgca gatgcaggcg      240
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 92
<211> LENGTH: 453
<212> TYPE: DNA
<213> ORGANISM: Hepatitis B virus

<400> SEQUENCE: 92

```
atggatatcg acccgtacaa agaattcggc gcgaccgttg aactgctgtc tttcctgccg      60
tctgatttct tcccgtctgt tcgttgcctg ctggacaccg cggcagcact gtaccgtgac      120
gcgctggaat ctccggaaca ttgttctccg catcacactg cgctgcgtca ggcggtgagc      180
tgctggcgcg aagtgaccga ttttggcgat tgggtgggca acaacctgca ggatatggcg      240
gcgcgcgatc tggtggtgaa ctatgtgaac gcgaacattg gcctgaaaat tcgtcagctg      300
ctgtggttcc acatctcttg cctgaccttc ggtcgtgaaa ccgttctgga atacctggtt      360
tcttttggtg tttggatttg tactccgccg gcttaccgtc cgccgaacgc accgatcctg      420
agcaccctgc cggaaaccac tgttgtgtaa taa                                   453
```

<210> SEQ ID NO 93
<211> LENGTH: 453
<212> TYPE: DNA
<213> ORGANISM: Hepatitis B virus

<400> SEQUENCE: 93

| | | |
|---|---|---|
| atggatatcg acccgtacaa agaattcggc gcgaccgttg aactgctgtc tttcctgccg | 60 |
| tctgatttct ccccgtctgt tcgttgcctg ctggacaccg cggcagcact gtaccgtgac | 120 |
| gcgctggaat ctccggaaca ttgttctccg catcacactg cgctgcgtca ggcggtgagc | 180 |
| tgctggcgcg aagtgaccga ttttggcgat tgggtgggca acaacctgca ggatcagatg | 240 |
| gcgcgcgatc tggtggtgaa ctatgtgaac gcgaacattg gcctgaaaat cgtcagctg | 300 |
| ctgtggttcc acatctcttg cctgaccttc ggtcgtgaaa ccgttctgga atacctggtt | 360 |
| tcttttggtg tttggatttg tactccgccg gcttaccgtc cgccgaacgc accgatcctg | 420 |
| agcacccctgc cggaaaccac tgttgtgtaa taa | 453 |

<210> SEQ ID NO 94
<211> LENGTH: 453
<212> TYPE: DNA
<213> ORGANISM: Hepatitis B virus

<400> SEQUENCE: 94

| | | |
|---|---|---|
| atggatatcg acccgtacaa agaattcggc gcgaccgttg aactgctgtc tttcctgccg | 60 |
| tctgatttct ccccgtctgt tcgttgcctg ctggacaccg cggcagcact gtaccgtgac | 120 |
| gcgctggaat ctccggaaca ttgttctccg catcacactg cgctgcgtca ggcggtgagc | 180 |
| tgctggcgcg aagtgaccga ttttggcgat tgggtgggca acaacctgca gatgcaggcg | 240 |
| gcgcgcgatc tggtggtgaa ctatgtgaac gcgaacattg gcctgaaaat cgtcagctg | 300 |
| ctgtggttcc acatctcttg cctgaccttc ggtcgtgaaa ccgttctgga atacctggtt | 360 |
| tcttttggtg tttggatttg tactccgccg gcttaccgtc cgccgaacgc accgatcctg | 420 |
| agcacccctgc cggaaaccac tgttgtgtaa taa | 453 |

<210> SEQ ID NO 95
<211> LENGTH: 453
<212> TYPE: DNA
<213> ORGANISM: Hepatitis B virus

<400> SEQUENCE: 95

| | | |
|---|---|---|
| atggatatcg acccgtacaa agaattcggc gcgaccgttg aactgctgtc tttcctgccg | 60 |
| tctgatttct ccccgtctgt tcgtgacctg ctggacaccg cggcagcact gtaccgtgac | 120 |
| gcgctggaat ctccggaaca ttgttctccg catcacactg cgctgcgtca ggcggtgagc | 180 |
| tgctggcgcg aagtgaccga ttttggcgat tgggtgggca acaacctgca gatgcaggcg | 240 |
| gcgcgcgatc tggtggtgaa ctatgtgaac gcgaacattg gcctgaaaat cgtcagctg | 300 |
| ctgtggttcc acatctcttg cctgtgcttc ggtcgtgaaa ccgttctgga atacctgtgt | 360 |
| tcttttggtg tttggattcg tactccgccg gcttaccgtc cgccgaacgc accgatcctg | 420 |
| agcacccctgc cggaaaccac tgttgtgtaa taa | 453 |

<210> SEQ ID NO 96
<211> LENGTH: 453
<212> TYPE: DNA
<213> ORGANISM: Hepatitis B virus

<400> SEQUENCE: 96

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacctgca gatgcaggcg     240
gcgcgcgatc tggtggtgaa ctatgtgaac gcgaacattg gcctgaaaat tcgtcagctg     300
ctgtggttcc acatctcttg cctgaccttc ggtcgtgaaa ccgttctgga atacctggtt     360
tcttttggtg tttggattcg tactccgccg gcttgccgtc cgccgtgcgc accgatcctg     420
agcaccctgc cggaaaccac tgttgtgtaa taa                                  453
```

<210> SEQ ID NO 97
<211> LENGTH: 453
<212> TYPE: DNA
<213> ORGANISM: Hepatitis B virus

<400> SEQUENCE: 97

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacctgca gatgcaggcg     240
gcgcgcgatc tggtggtgaa ctatgtgaac gcgaacattg gcctgaaaat tcgtcagctg     300
ctgtggttcc acatctcttg cctgaccttc ggtcgtgaaa ccgttctgga atacctggtt     360
tcttttggtg tttggattcg tactccgccg gcttgccgtc cgccgaactg cccgatcctg     420
agcaccctgc cggaaaccac tgttgtgtaa taa                                  453
```

<210> SEQ ID NO 98
<211> LENGTH: 453
<212> TYPE: DNA
<213> ORGANISM: Hepatitis B virus

<400> SEQUENCE: 98

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacctgca gatgcaggcg     240
gcgcgcgatc tggtggtgaa ctatgtgaac gcgaacattg gcctgaaaat tcgtcagctg     300
ctgtggttcc acatctcttg cctgaccttc ggtcgtgaaa ccgttctgga atacctggtt     360
tcttttggtg tttggattcg tactccgccg gcttactgcc cgccgtgcgc accgatcctg     420
agcaccctgc cggaaaccac tgttgtgtaa taa                                  453
```

<210> SEQ ID NO 99
<211> LENGTH: 453
<212> TYPE: DNA
<213> ORGANISM: Hepatitis B virus

<400> SEQUENCE: 99

```
atggatatcg acccgtacaa agaattcggc gcgaccgttg aactgctgtc tttcctgccg      60
tctgatttct tcccgtctgt tcgtgacctg ctggacaccg cggcagcact gtaccgtgac     120
gcgctggaat ctccggaaca ttgttctccg catcacactg cgctgcgtca ggcggtgagc     180
```

```
tgctggcgcg aagtgaccga ttttggcgat tgggtgggca acaacctgca gatgcaggcg    240
gcgcgcgatc tggtggtgaa ctatgtgaac gcgaacattg gcctgaaaat tcgtcagctg    300
ctgtggttcc acatctcttg cctgaccttc ggtcgtgaaa ccgttctgga atacctggtt    360
tcttttggtg tttggattcg tactccgccg gcttactgcc cgccgaactg cccgatcctg    420
agcaccctgc cggaaaccac tgttgtgtaa taa                                 453
```

<210> SEQ ID NO 100
<211> LENGTH: 453
<212> TYPE: DNA
<213> ORGANISM: Hepatitis B virus

<400> SEQUENCE: 100

```
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcggtgagc    180
tgctggcgcg aagtgaccga ttttggcgat tgggtgggca acaacctgca gatgcaggcg    240
gcgcgcgatc tggtggtgaa ctatgtgaac gcgaacattg gcctgaaaat tcgtcagctg    300
ctgtggttcc acatctcttg cctgaccttc ggtcgtgaaa ccgttctgga atacctggtt    360
tcttttggtg tttggattcg tactccgccg gcttaccgtt gctgcaacgc accgatcctg    420
agcaccctgc cggaaaccac tgttgtgtaa taa                                 453
```

<210> SEQ ID NO 101
<211> LENGTH: 453
<212> TYPE: DNA
<213> ORGANISM: Hepatitis B virus

<400> SEQUENCE: 101

```
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcggtgagc    180
tgctggcgcg aagtgaccga ttttggcgat tgggtgggca acaacctgca gatgcaggcg    240
gcgcgcgatc tggtggtgaa ctatgtgaac gcgaacattg gcctgaaaat tcgtcagctg    300
ctgtggttcc acatctcttg cctgaccttc ggtcgtgaaa ccgttctgga atacctggtt    360
tcttttggtg tttggattcg tactccgccg gcttaccgtt gcccgtgcgc accgatcctg    420
agcaccctgc cggaaaccac tgttgtgtaa taa                                 453
```

<210> SEQ ID NO 102
<211> LENGTH: 453
<212> TYPE: DNA
<213> ORGANISM: Hepatitis B virus

<400> SEQUENCE: 102

```
atggatatcg acccgtacaa agaattcggc gcgaccgttg aactgctgtc tttcctgccg     60
tctgatttct tcccgtctgt tcgtgacctg ctggacaccg cggcagcact gtaccgtgac    120
gcgctggaat ctccggaaca ttgttctccg catcacactg cgctgcgtca ggcggtgagc    180
tgctggcgcg aagtgaccga ttttggcgat tgggtgggca acaacctgca gatgcaggcg    240
gcgcgcgatc tggtggtgaa ctatgtgaac gcgaacattg gcctgaaaat tcgtcagctg    300
ctgtggttcc acatctcttg cctgaccttc ggtcgtgaaa ccgttctgga atacctggtt    360
```

```
tcttttggtg tttggattcg tactccgccg gcttaccgtt gcccgaactg cccgatcctg      420
agcaccctgc cggaaaccac tgttgtgtaa taa                                   453
```

<210> SEQ ID NO 103
<211> LENGTH: 453
<212> TYPE: DNA
<213> ORGANISM: Hepatitis B virus

<400> SEQUENCE: 103

```
atggatatcg acccgtacaa agaattcggc gcgaccgttg aactgctgtc tttcctgccg      60
tctgatttct ccccgtctgt tcgtgacctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacctgca gatgcaggcg     240
gcgcgcgatc tggtggtgaa ctatgtgaac gcgaacattg gcctgaaaat cgtcagctg     300 ctgtggttcc acatctcttg cctgaccttc ggtcgtgaaa ccgttctgga atacctggtt     360
tcttttggtg tttggattcg tactccgccg gcttaccgtc cgtgctgcgc accgatcctg     420
agcaccctgc cggaaaccac tgttgtgtaa taa                                   453
```

<210> SEQ ID NO 104
<211> LENGTH: 453
<212> TYPE: DNA
<213> ORGANISM: Hepatitis B virus

<400> SEQUENCE: 104

```
atggatatcg acccgtacaa agaattcggc gcgaccgttg aactgctgtc tttcctgccg      60
tctgatttct ccccgtctgt tcgttgcctg ctggacaccg cggcagcact gtaccgtgac     120
gcgctggaat ctccggaaca ttgttctccg catcacactg cgctgcgtca ggcggtgagc     180
tgctggcgcg aagtgaccga ttttggcgat tgggtgggca acaacctgca gatgcaggcg     240
gcgcgcgatc tggtggtgaa ctatgtgaac gcgaacattg gcctgaaaat cgtcagctg     300 ctgtggttcc acatctcttg cctgaccttc ggtcgtgaaa ccgttctgga atacctggtt     360
tcttttggtg tttggatttg tactccgccg gcttaccgtt gcccgtgcgc accgatcctg     420
agcaccctgc cggaaaccac tgttgtgtaa taa                                   453
```

<210> SEQ ID NO 105
<211> LENGTH: 149
<212> TYPE: PRT
<213> ORGANISM: Hepatitis B virus

<400> SEQUENCE: 105

```
Met Asp Ile Asp Pro Tyr Lys Glu Phe Gly Ala Ser Val Glu Leu Leu
1               5                   10                  15

Ser Phe Leu Pro Ser Asp Phe Tyr Pro Ser Val Arg Asp Leu Leu Asp
            20                  25                  30

Thr Ala Ser Ala Leu His Arg Asp Ala Leu Glu Ser Pro Glu His Cys
        35                  40                  45

Ser Pro His His Thr Ala Leu Arg Gln Ala Val Ser Cys Trp Arg Glu
    50                  55                  60

Val Thr Asp Phe Gly Asp Trp Val Gly Asn Asn Leu Gln Asp Gln Ala
65                  70                  75                  80

Ala Arg Asp Leu Val Val Asn Tyr Val Asn Ala Asn Ile Gly Leu Lys
                85                  90                  95

Ile Arg Gln Leu Leu Trp Phe His Ile Ser Cys Leu Thr Phe Gly Arg
```

```
                    100                 105                 110
Glu Thr Val Ile Glu Tyr Leu Val Ser Phe Gly Val Trp Ile Arg Thr
                115                 120                 125

Pro Pro Ala Tyr Arg Pro Pro Asn Ala Pro Ile Leu Ser Thr Leu Pro
            130                 135                 140

Glu Thr Thr Val Val
145

<210> SEQ ID NO 106
<211> LENGTH: 39
<212> TYPE: PRT
<213> ORGANISM: Hepatitis B virus

<400> SEQUENCE: 106

Ile Leu Cys Trp Gly Asp Leu Met Thr Leu Ala Thr Trp Val Gly Thr
1               5                   10                  15

Asn Leu Glu Asp Pro Ala Ser Arg Asp Leu Val Val Ser Tyr Val Asn
            20                  25                  30

Thr Asn Val Gly Leu Lys Phe
            35

<210> SEQ ID NO 107
<211> LENGTH: 39
<212> TYPE: PRT
<213> ORGANISM: Hepatitis B virus

<400> SEQUENCE: 107

Val Ser Cys Trp Arg Glu Val Thr Asp Phe Gly Asp Trp Val Gly Asn
1               5                   10                  15

Asn Leu Gln Asp Gln Ala Ala Arg Asp Leu Val Val Asn Tyr Val Asn
            20                  25                  30

Ala Asn Ile Gly Leu Lys Ile
            35

<210> SEQ ID NO 108
<211> LENGTH: 153
<212> TYPE: PRT
<213> ORGANISM: Hepatitis B virus

<400> SEQUENCE: 108

Ala His Ala Asp Ile Asp Pro Tyr Lys Glu Phe Gly Ala Thr Val Glu
1               5                   10                  15

Leu Leu Ser Phe Leu Pro Ser Asp Phe Phe Pro Ser Val Arg Cys Leu
            20                  25                  30

Leu Asp Thr Ala Ala Ala Leu Tyr Arg Asp Ala Leu Glu Ser Pro Glu
        35                  40                  45

His Cys Ser Pro His His Thr Ala Leu Arg Gln Ala Ile Leu Cys Trp
    50                  55                  60

Gly Asp Leu Ser Thr Leu Ala Thr Trp Val Gly Thr Asn Leu Glu Ala
65                  70                  75                  80

His Ala Pro Ala Ser Arg Asp Leu Val Val Ser Tyr Val Asn Thr Asn
                85                  90                  95

Val Gly Leu Lys Phe Arg Gln Leu Leu Trp Phe His Ile Ser Cys Leu
            100                 105                 110

Thr Phe Gly Arg Glu Thr Val Leu Glu Tyr Leu Val Ser Phe Gly Val
        115                 120                 125

Trp Ile Cys Thr Pro Pro Ala Tyr Arg Pro Pro Asn Ala Pro Ile Leu
    130                 135                 140
```

```
Ser Thr Leu Pro Glu Thr Thr Val Val
145                 150

<210> SEQ ID NO 109
<211> LENGTH: 153
<212> TYPE: PRT
<213> ORGANISM: Hepatitis B virus

<400> SEQUENCE: 109

Ala His Ala Asp Ile Asp Pro Tyr Lys Glu Phe Gly Ala Thr Val Glu
1               5                   10                  15

Leu Leu Ser Phe Leu Pro Ser Asp Phe Phe Pro Ser Val Arg Cys Leu
            20                  25                  30

Leu Asp Thr Ala Ala Ala Leu Tyr Arg Asp Ala Leu Glu Ser Pro Glu
        35                  40                  45

His Cys Ser Pro His His Thr Ala Leu Arg Gln Ala Ile Leu Cys Trp
    50                  55                  60

Gly Asp Leu Ser Thr Leu Ala Thr Trp Val Gly Asn Asn Ala His Ala
65                  70                  75                  80

Gln Asp Gln Ala Ala Arg Asp Leu Val Val Ser Tyr Val Asn Thr Asn
                85                  90                  95

Val Gly Leu Lys Phe Arg Gln Leu Leu Trp Phe His Ile Ser Cys Leu
            100                 105                 110

Thr Phe Gly Arg Glu Thr Val Leu Glu Tyr Leu Val Ser Phe Gly Val
        115                 120                 125

Trp Ile Cys Thr Pro Pro Ala Tyr Arg Pro Pro Asn Ala Pro Ile Leu
    130                 135                 140

Ser Thr Leu Pro Glu Thr Thr Val Val
145                 150

<210> SEQ ID NO 110
<211> LENGTH: 153
<212> TYPE: PRT
<213> ORGANISM: Hepatitis B virus

<400> SEQUENCE: 110

Ala His Ala Asp Ile Asp Pro Tyr Lys Glu Phe Gly Ala Thr Val Glu
1               5                   10                  15

Leu Leu Ser Phe Leu Pro Ser Asp Phe Phe Pro Ser Val Arg Cys Leu
            20                  25                  30

Leu Asp Thr Ala Ala Ala Leu Tyr Arg Asp Ala Leu Glu Ser Pro Glu
        35                  40                  45

His Cys Ser Pro His His Thr Ala Leu Arg Gln Ala Val Ser Cys Trp
    50                  55                  60

Arg Glu Val Thr Asp Phe Gly Asp Trp Val Gly Asn Asn Ala His Ala
65                  70                  75                  80

Gln Asp Gln Ala Ala Arg Asp Leu Val Val Asn Tyr Val Asn Ala Asn
                85                  90                  95

Ile Gly Leu Lys Ile Arg Gln Leu Leu Trp Phe His Ile Ser Cys Leu
            100                 105                 110

Thr Phe Gly Arg Glu Thr Val Leu Glu Tyr Leu Val Ser Phe Gly Val
        115                 120                 125

Trp Ile Cys Thr Pro Pro Ala Tyr Arg Pro Pro Asn Ala Pro Ile Leu
    130                 135                 140

Ser Thr Leu Pro Glu Thr Thr Val Val
145                 150
```

```
<210> SEQ ID NO 111
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 2-183 of HBV ID:
      Q89612

<400> SEQUENCE: 111
```

Asp Ile Asp Pro Tyr Lys Glu Phe Gly Ala Ser Val Glu Leu Val Ser
1               5                   10                  15

Phe Leu Pro Ser Asp Phe Phe Pro Ser Ile Arg Asp Leu Leu Asp Thr
                20                  25                  30

Ala Ala Ala Leu Tyr Arg Glu Ala Leu Glu Ser Pro Glu His Cys Ser
            35                  40                  45

Ala His His Thr Ala Leu Arg Gln Ala Ile Leu Cys Trp Gly Glu Leu
        50                  55                  60

Met Asn Leu Ala Thr Trp Val Gly Ser Asn Leu Glu Asp Pro Ala Ser
65                  70                  75                  80

Arg Glu Leu Val Val Ser Tyr Val Asn Val Asn Met Gly Leu Lys Leu
                85                  90                  95

Arg Gln Ile Leu Trp Phe His Ile Ser Cys Leu Met Phe Gly Arg Glu
            100                 105                 110

Thr Val Leu Glu Tyr Leu Val Ser Phe Gly Val Trp Ile Arg Thr Pro
        115                 120                 125

Thr Ala Tyr Arg Pro Pro Asn Ala Pro Ile Leu Ser Thr Leu Pro Glu
    130                 135                 140

Thr Thr Val Ile Arg Gln Arg Arg Arg Ser Pro Arg Arg Arg Thr Pro
145                 150                 155                 160

Ser Pro Arg Arg Arg Arg Ser Gln Ser Pro Arg Arg Arg Arg Ser Gln
                165                 170                 175

Ser Arg Glu Ser Gln Cys
            180

```
<210> SEQ ID NO 112
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 2-183 of HBV ID:
      Q67976

<400> SEQUENCE: 112
```

Asp Ile Asp Pro Tyr Lys Glu Phe Gly Ala Thr Val Glu Leu Leu Ser
1               5                   10                  15

Phe Leu Pro Ser Asp Phe Phe Pro Ser Val Arg Asp Leu Leu Asp Thr
                20                  25                  30

Ala Ala Ala Leu Phe Arg Glu Ala Leu Glu Ser Pro Glu His Cys Thr
            35                  40                  45

Pro His His Thr Ala Leu Arg Gln Ala Ile Leu Cys Trp Gly Glu Leu
        50                  55                  60

Met Ser Leu Ala Thr Trp Val Gly Val Asn Leu Glu Asp Gln Ala Ser
65                  70                  75                  80

Arg Asp Leu Val Val Arg Tyr Val Asn Asp His Met Gly Ile Lys Phe

```
                    85                  90                  95
Arg Gln Leu Leu Trp Phe His Ile Ser Cys Leu Thr Phe Gly Arg Asp
                100                 105                 110

Thr Val Ile Glu Tyr Leu Val Ser Phe Gly Val Trp Ile Arg Thr Pro
            115                 120                 125

Pro Pro Tyr Arg Pro Pro Asn Ala Pro Ile Leu Ser Thr Leu Pro Glu
        130                 135                 140

Thr Thr Val Val Arg Arg Arg Gly Arg Ser Pro Arg Arg Arg Thr Pro
145                 150                 155                 160

Ser Pro Arg Arg Arg Arg Ser Gln Ser Pro Arg Arg Arg Arg Thr Gln
                165                 170                 175

Ser Arg Glu Ser Gln Cys
                180

<210> SEQ ID NO 113
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 2-183 of HBV ID:
      Q91719

<400> SEQUENCE: 113

Asp Ile Asp Pro Tyr Lys Glu Phe Gly Ala Ser Val Glu Leu Leu Ser
1               5                   10                  15

Phe Leu Pro Ser Asp Phe Phe Pro Ser Ile Arg Asp Leu Leu Asp Thr
            20                  25                  30

Ala Ser Ala Leu Phe Leu Gln Ala Leu Glu Ser Pro Glu His Cys Ser
        35                  40                  45

Pro His His Thr Ala Ile Arg Gln Ala Val Leu Cys Trp Gly Glu Leu
    50                  55                  60

Met Thr Leu Ala Thr Trp Val Gly Val Asn Leu Glu Asp Pro Ser Ser
65                  70                  75                  80

Arg Asp Leu Val Val Ser Tyr Val Asn Thr Asn Met Gly Leu Lys Phe
                85                  90                  95

Arg Gln Leu Leu Trp Phe His Ile Ser Cys Leu Thr Phe Gly Arg Glu
                100                 105                 110

Ile Val Ile Glu Tyr Leu Val Ser Phe Gly Val Trp Ile Arg Thr Pro
            115                 120                 125

Pro Ala Tyr Arg Pro Pro Asn Ser Pro Ile Leu Ser Thr Leu Pro Glu
        130                 135                 140

Thr Thr Val Val Arg Arg Arg Gly Arg Ser Pro Arg Arg Arg Thr Pro
145                 150                 155                 160

Ser Pro Arg Arg Arg Arg Ser Gln Ser Pro Arg Arg Arg Arg Ser Gln
                165                 170                 175

Ser Arg Glu Ser Gln Cys
                180

<210> SEQ ID NO 114
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 2-183 of HBV ID:
      Q6R610
```

<400> SEQUENCE: 114

```
Asp Ile Asp Pro Tyr Lys Glu Phe Gly Ala Ser Val Glu Leu Leu Ser
1               5                   10                  15

Phe Leu Pro Ala Asp Phe Ser Pro Ser Val Arg Asp Leu Leu Asp Thr
            20                  25                  30

Ala Ser Ala Leu Phe Arg Asp Ala Leu Glu Ser Pro Glu His Cys Ser
        35                  40                  45

Pro His Thr Ala Leu Arg Gln Ala Ile Leu Cys Trp Gly Asp Leu
    50                  55                  60

Met Ser Leu Ala Thr Trp Val Gly Gly Asn Leu Glu Asp Pro Thr Ser
65                  70                  75                  80

Arg Asp Leu Val Val Ser Tyr Val Asn Thr Asp Met Gly Leu Lys Phe
                85                  90                  95

Arg Gln Leu Leu Trp Phe His Ile Ser Cys Leu Thr Phe Gly Arg Glu
                100                 105                 110

Thr Val Val Glu Tyr Leu Val Ser Phe Gly Val Trp Ile Arg Thr Pro
            115                 120                 125

Pro Ala Tyr Arg Pro Gln Asn Ala Pro Ile Leu Ser Thr Leu Pro Glu
130                 135                 140

Thr Ala Val Val Arg Arg Ser Arg Thr Pro Arg Gly Arg Thr Pro
145                 150                 155                 160

Ser Pro Arg Arg Arg Ser Gln Ser Pro Arg Arg Arg Ser Gln
                165                 170                 175

Ser Arg Asp Ser Gln Cys
            180
```

<210> SEQ ID NO 115
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 2-183 of HBV ID: Q67970

<400> SEQUENCE: 115

```
Asp Ile Ser Pro Tyr Lys Glu Phe Gly Ala Ser Val Glu Leu Leu Ser
1               5                   10                  15

Phe Leu Pro Val Asp Phe Phe Pro Ser Val Arg Asp Leu His Asp Thr
            20                  25                  30

Ala Thr Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Gly Asn Leu Glu Asp Ser Thr Ser
65                  70                  75                  80

Arg Asp Leu Val Val Ser Tyr Val Asn Thr Asn Met Gly Leu Lys Phe
                85                  90                  95

Arg Gln Leu Leu Trp Phe His Val Ser Cys Leu Met Phe Gly Arg Glu
                100                 105                 110

Leu Val Val Glu Tyr Leu Val Ser Phe Gly Val Trp Ile Arg Thr Pro
            115                 120                 125

Pro Ala Tyr Arg Pro Ser Asn Ala Pro Ile Leu Ser Thr Leu Pro Glu
130                 135                 140
```

Thr Cys Val Val Arg Arg Arg Gly Arg Ser Pro Arg Arg Arg Thr Pro
145                 150                 155                 160

Ser Pro Arg Arg Arg Ser Gln Ser Pro Arg Arg Arg Ser Gln
            165                 170                 175

Ser Arg Glu Ser Gln Cys
            180

<210> SEQ ID NO 116
<211> LENGTH: 184
<212> TYPE: PRT
<213> ORGANISM: Hepatitis B virus
<220> FEATURE:
<221> NAME/KEY: MISC_FEATURE
<222> LOCATION: (1)..(184)
<223> OTHER INFORMATION: Sequence is from positions 2-185 of HBV ID:
      CAPSO

<400> SEQUENCE: 116

Asp Ile Asp Pro Tyr Lys Glu Phe Gly Ala Thr Val Glu Leu Leu Ser
1               5                   10                  15

Phe Leu Pro Ser Asp Phe Phe Pro Ser Val Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Thr Leu Ala Thr Trp Val Gly Asn Asn Leu Glu Asp Pro Ala Ser
65                  70                  75                  80

Arg Asp Leu Val Val Asn Tyr Val Asn Thr Asn Val Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125

Pro Ala Tyr Arg Pro Pro Asn Ala Pro Ile Leu Ser Thr Leu Pro Glu
    130                 135                 140

Thr Thr Val Val Arg Arg Arg Asp Arg Gly Arg Ser Pro Arg Arg Arg
145                 150                 155                 160

Thr Pro Ser Pro Arg Arg Arg Arg Ser Pro Ser Pro Arg Arg Arg Arg
            165                 170                 175

Ser Gln Ser Arg Glu Ser Gln Cys
            180

<210> SEQ ID NO 117
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 31-212 of HBV ID:
      Q8B6N7

<400> SEQUENCE: 117

Asp Ile Asp Pro Tyr Lys Glu Phe Gly Ala Ser Val Glu Leu Leu Ser
1               5                   10                  15

Phe Leu Pro Ser Asp Phe Tyr Pro Ser Val Arg Asp Leu Leu Asp Thr
            20                  25                  30

Ala Ser Ala Leu His Arg Asp Ala Leu Glu Ser Pro Glu His Cys Ser
        35                  40                  45

```
Pro His His Thr Ala Leu Arg Gln Ala Val Ser Cys Trp Arg Glu Val
    50                  55                  60

Thr Asp Phe Gly Asp Trp Val Gly Asn Asn Leu Gln Asp Gln Ala Ala
 65                  70                  75                  80

Arg Asp Leu Val Val Asn Tyr Val Asn Ala Asn Ile Gly Leu Lys Ile
                 85                  90                  95

Arg Gln Leu Leu Trp Phe His Ile Ser Cys Leu Thr Phe Gly Arg Glu
                100                 105                 110

Thr Val Ile Glu Tyr Leu Val Ser Phe Gly Val Trp Ile Arg Thr Pro
            115                 120                 125

Pro Ala Tyr Arg Pro Asn Ala Pro Ile Leu Ser Thr Leu Pro Glu
            130                 135                 140

Thr Thr Val Val Arg Gln Arg Gly Arg Ala Pro Arg Arg Arg Thr Pro
145                 150                 155                 160

Ser Pro Arg Arg Arg Ser Gln Ser Pro Arg Arg Arg Arg Ser Gln
                165                 170                 175

Ser Pro Ser Ser Lys Cys
            180
```

<210> SEQ ID NO 118
<211> LENGTH: 182
<212> TYPE: PRT
<213> ORGANISM: Hepatitis B virus
<220> FEATURE:
<221> NAME/KEY: MISC_FEATURE
<222> LOCATION: (1)..(182)
<223> OTHER INFORMATION: Sequence is from positions 31-212 of HBV ID:
      Q9E946

<400> SEQUENCE: 118

```
Asp Ile Asp Pro Tyr Lys Glu Phe Gly Ala Thr Val Glu Leu Leu Ser
  1               5                  10                  15

Phe Leu Pro Ser Asp Phe Phe Pro Ser Gly Arg Asp Leu Leu Asp Thr
                 20                  25                  30

Ala Arg Ala Leu Tyr Gln Glu Ala Leu Thr Ser Ala Asp His Tyr Ser
             35                  40                  45

Ser His His Thr Ala Leu Arg Gln Ala Ile Trp Cys Trp Glu Asp Phe
 50                  55                  60

Ile Ser Leu Ala Ser Trp Val Gly Asn Glu Leu Glu Asp Pro Ile Ser
 65                  70                  75                  80

Lys Glu Leu Val Ile Thr Tyr Val Asp Thr Asn Leu Gly Leu Lys Ile
                 85                  90                  95

Arg Gln Leu Leu Trp Phe His Ile Ser Cys Leu Thr Phe Gly Arg Glu
                100                 105                 110

Thr Val Leu Glu Tyr Leu Val Ser Phe Gly Val Trp Ile Arg Thr Pro
            115                 120                 125

Pro Ala Tyr Arg Pro Gln Asn Ala Pro Ile Leu Ser Ile Ser Glu
            130                 135                 140

Thr Ile Val Val Gly Arg Thr Gly Arg Ser Ser Arg Arg Arg Thr Pro
145                 150                 155                 160

Ser Pro Arg Arg Arg Ser Gln Ser Thr Cys Arg Arg Arg Ser Gln
                165                 170                 175

Ser Pro Ala Ser Gln Cys
            180
```

STABILIZED HEPATITIS B CORE POLYPEPTIDES

This application is an 111a application of PCT/US2014/012586, filed Jan. 22, 2014, which claims the benefit of U.S. Provisional Application No. 61/755,850, filed Jan. 23, 2013 and U.S. Provisional Application No. 61/901,243, filed Nov. 7, 2013, the contents of all of which are incorporated herein by reference in their entireties into the present application.

Throughout this application various publications are referenced. The disclosures of these publications in their entireties are hereby incorporated by reference into this application in order to more fully describe the state of the art to which this invention pertains.

BACKGROUND OF THE INVENTION

Virus-like particles (VLPs) are non-infectious, have repetitive surfaces that can display molecules with a high surface density, and have comparable cellular uptake and intracellular trafficking compared to natural virus. All of these functional attributes make them attractive as the assembly core for vaccines, diagnostics, and therapeutics. They can potentially serve as polyvalent scaffolds for the display of nucleic acids, proteins, and other chemical moieties. VLPs are particularly attractive as vaccines as they offer in vivo stability, trafficking to lymph nodes, and stimulation of B and T cell responses by the displayed epitopes. They can also be filled with cargo to serve as delivery vehicles.

Cell-free protein synthesis (CFPS) can be an effective method for producing VLPs, for example those comprising Hepatitis B core protein (HBc), MS2 bacteriophage coat protein, and Qβ bacteriophage coat protein, and the like. CFPS also provides a facile means for introducing non-natural amino acids (nnAAs) into proteins, which allows for the direct protein-protein coupling of antigens to VLPs using Cu(I)-catalyzed [3+2] cycloaddition click chemistry.

Among different types of VLPs, the HBc VLP is a flexible and promising model for knowledge-based display of foreign peptide sequences. The HBc particle was first reported as a promising VLP carrier in 1986. Being one of the first VLP candidates and the first icosahedral VLP carrier, HBc VLP has been well characterized and widely used as a carrier for over 100 different foreign sequences. The HBc capsid protein is 183 to 185 amino acids long. The arginine-rich C-terminus of HBc protein is dispensable for VLP assembly, so the HBc protein truncated at amino acid 149 is widely used. The truncated HBc (1-149) proteins can self-assemble into the particle with an average diameter of 28 to 30 nm and a dominant icosahedral symmetry of T=4.

However, in current applications of HBc VLPs, there is a serious problem. The VLP is not stable during click chemistry conjugations, and can disassemble after conjugation with functional molecules. Two truncated HBc monomers (16.7 kDa) form a dimer (33.5 kDa) by an intradimer C61-C61 disulfide bond. Then 120 dimers self-assemble into one VLP by hydrophobic interactions. Because the interdimer contacts are weak, conjugation of functional molecules onto the VLP surface can disturb the interactions between VLP dimers, resulting in VLP instability. The second problem is molecules with negative charges conjugate poorly to VLPs. At physiological pH, the surface of the HBc VLP is negatively charged. Because like charges repel, molecules with negative charges cannot get close to HBc VLP, and therefore the click chemistry conjugation cannot proceed effectively.

The present invention addresses these two problems, and provides stabilized HBc VLPs and a modified VLP surface.

Relevant Literature

Methods of introducing unnatural amino acids during CFPS are described in patent publication US 2010-0093024 A1. Methods of directly linking antigens and other polypeptides to a virus-like particle through unnatural amino acids are described in patent application US-2010-0168402-A1. Methods of encapsidating cargo into virus-like particles produced by CFPS are described in patent publication US-2010-0167981-A1. Each of these documents are herein specifically incorporated by reference.

SUMMARY OF THE INVENTION

Genetically modified hepatitis B core (HBc) proteins are provided, which proteins comprise sequence modification that enhance the stability and/or utility of the protein. In some embodiments of the invention, at least two amino acids of the native sequence are substituted with cysteine residues that provide for intermolecular disulfide bonding. In some embodiments four amino acids are substituted with cysteines. The HBc protein is thus stabilized and is maintained as a virus-like particle (VLP) under conditions otherwise unfavorable to retention of the quaternary structure, for example during click chemistry reactions.

In some embodiments, at least two amino acids present in an HBc monomer, usually two amino acids or four amino acids, for example a sequence set forth in SEQ ID NO:1, SEQ ID NO:2, SEQ ID NO:34, SEQ ID NO:35, or a comparable HBc polypeptide, are replaced with cysteine, which replacements stabilize the protein assembly. Exemplary pairs of amino acid substitutions include, without limitation and using relative to SEQ ID NO:1, SS1: D29C, R127C; SS2: T109C, V120C; SS3: Y132C, N136C; SS4: Y132C, A137C; SS5: R133C, N136C; SS6: R133C, A137C; SS7: P134C, P135C; SS8: P134C, N136C; SS9: P134C, A137C; and SS10: P135C, N136C. In some embodiments the amino acid substitutions are D29C and R127C. In other embodiments the amino acid substitutions are P134C and N136C. In some embodiments the amino acid substitutions are D29C, R127C, P134C and N136C.

In other embodiments, the HBc protein alternatively or in addition comprises a set of amino acid substitutions that reduces the negative charge on the "spike tip" of the protein, i.e., i.e. the region of residues 73-81, relative to SEQ ID NO:1 or SEQ ID NO:2. In some embodiments the set of amino acid substitutions is derived from a naturally occurring virus genotype with a reduced charge. In some embodiments, the set of amino acid changes, relative to SEQ ID NO:1 or SEQ ID NO:2 are I59V, L60S, G63R, D64E, L65V, M66T, T67D, L68F, A69G, T70D, T74N, L76M, E77Q, P79Q, S81A, S87N, T91A, V93I, and F97I. In some embodiments the set of amino acid changes is T74N, L76M, E77Q, P79Q, and S81A. In some embodiments, the amino acid sequence of the HBc protein with a reduced negative charge is SEQ ID NO:34 or SEQ ID NO:35.

The HBc protein, either cysteine stabilized, charge reduced, or both, can further comprise one or more unnatural amino acids at a pre-determined site. Unnatural amino acids of interest include without limitation azidohomoalanine, p-acetyl-phenylalanine, p-ethynyl-phenylalanine, p-propargyloxyphenylalanine, p-azido-phenylalanine, etc. The unnatural amino acid(s) may be positioned at the spike of the HBc protein. Sites of interest include, for example, N75, T74, L76, Q77, D78, Q79 and A80. In some embodiments the unnatural amino acid replaces D78. In some embodiments the unnatural amino acid is azidohomoalanine.

HBc polypeptides, or VLP generated therefrom may comprise a conjugated moiety other than an HBc polypeptide, where such a moiety is conjugated to the HBc at the introduced unnatural amino acid, e.g. by click chemistry. Suitable moieties include polypeptides, nucleic acids, polysaccharides, therapeutic drugs, imaging moieties, and the like. In a related embodiment, a method is provided, where the unnatural amino acid in HBc is utilized in a click chemistry reaction to join an additional moiety to the HBc of the invention, or a VLP comprising HBc of the invention.

The HBc polypeptides of this invention can be made by transforming host cells with nucleic acid encoding the polypeptide, culturing the host cell and recovering the polypeptide from the culture, or alternatively by generating a nucleic acid construct encoding the HBc polypeptides and producing the polypeptide by cell free synthesis, which synthesis may include coupled transcription and translation reactions. Also provided are vectors and polynucleotides encoding the HBc polypeptides. In some embodiments a VLP comprising polypeptides of the invention is provided.

In one embodiment of the invention, a method is provided for the cell-free protein synthesis (CFPS) of the protein of the invention. In some embodiments the CFPS product is synthesized; and may further be assembled into a VLP, in a reducing environment. The CFPS product may be dialyzed in a solution of from about 1M to about 2 M salt, e.g. about 1.5 M salt, e.g. NaCl, etc. The assembled VLP may be isolated in a reducing environment. Following synthesis and assembly into a VLP, the VLP may be switched to an oxidizing environment to generate stabilizing disulfide bonds.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A-1C. Illustration of Hepatitis B core protein (HBc) VLP assembly, disassembly and its conjugation with foreign molecules. (FIG. 1A) HBc VLP is formed by self-assembly of 120 dimers. (FIG. 1B) The T=4 capsid structure of Hepatitis B core protein ($HBc_{1-149}$) VLP constructed from 12 pentamers and 30 hexamers. (FIG. 1C) The structures of the pentamer and the hexamer subunits FIG. 2A-2I. Synthesis and functional verification of stabilized HBc VLP with correct disulfide bonds. (FIG. 2A) The schematic replication cycle of HBV. (FIG. 2B) Schematic for the introduction of artificial disulfide (S—S) bond network. (FIG. 2C) Selection of possible S—S bonds between side chains of dimers or between C-terminus of monomers for both the 5-fold units (top) and the 6-fold units (bottom). (FIG. 2D) Size-exclusion chromatography (SEC) analysis of stabilized VLPs. O: Original HBc. (FIG. 2E) The non-reducing SDS-PAGE and the autoradiogram analysis after the oxidization treatment of purified VLPs. (FIG. 2F) Transmission electron microscope (TEM) images of VLPs. Arrows indicate examples where the HBc antigen protein did not assemble into the VLP completely. (FIG. 2G) SEC analysis of purified VLPs after overnight incubation in different buffers. The purified VLPs were initially formulated in the assembly buffer. The buffers were then exchanged into different buffers (the assembly buffer, PBS buffer, and 10 mM Tris-HCl (pH 7.4) buffer without NaCl salt) by dialysis. The SEC running buffer was the same as the dialysis buffer. (FIG. 2H) Sucrose gradient centrifugation analysis of HBc VLPs after one freeze-thaw cycle. The VLPs in the assembly buffer were flash frozen in the liquid N2 and stored at −80° C. After one week, the VLPs were thawed on ice and then analyzed by sucrose gradient centrifugation. (FIG. 2I) Reducing SDS-PAGE analysis of click-reaction products. Cu(I) was not added to the reaction as the control. HBc VLPs (monomer: 16.7 kDa) were radioactive. Flagellin (52.7 kDa) and GMCSF (16.1 kDa) were not radioactive.

FIG. 3A-3H. Stabilization of HBc VLP with artificial disulfide bonds. (FIG. 3A) The procedure for the HBc protein synthesis, VLP self-assembly, VLP purification, S—S bond formation and the verification of correct S—S bonding. The dialysis buffer: 10 mM Tris-HCl(pH 7.4), 0.5 M NaCl. (FIG. 3B) CFPS yields of original HBc protein and mutants. (FIG. 3C) Autoradiogram analysis of non-reducing SDS-PAGE. (FIG. 3D) Self-assembly analysis of HBc VLP in the 10 mM Tris-HCl (pH 7.4) buffer with different NaCl concentrations using size-exclusion chromatography (SEC). (FIG. 3E) The non-reducing SDS-PAGE and the autoradiogram analysis after the oxidization treatment of purified VLPs. The SEC fractions 9-11 were pooled as the purified VLPs. Hydrogen peroxide and diamide were used as oxidants. (FIG. 3F) Sucrose gradient centrifugation analysis of original HBc VLP and oxidized SS1, SS7, SS8, SS9 and SS10 VLPs. (FIG. 3G) Diagram of Cu(I)-catalyzed [3+2] cycloaddition click chemistry reaction for the direct coupling of functional molecules to HBc VLPs. (FIG. 3H) Reducing SDS-PAGE analysis of click-reaction products. Cu(I) was not added to the reaction as the control. HBc VLPs (monomer: 16.7 kDa) were radioactive. Flagellin (52.7 kDa) and GMCSF (16.1 kDa) were not radioactive.

FIG. 4A-4H. New mutants produced by transplanting the spike region of the natural mutant, Q8B6N7, into HBc SS1. (FIG. 4A) The difference between the HBc protein used in this study (UniProt accession number: P03147) (SEQ ID NO: 32)and a natural mutant (UniProt accession number: Q8B6N7) (SEQ ID NO: 105). The residue differences are shown in the protein structures and amino acid sequences. Both protein sequences are truncated at 149. The differences are underlined and marked in yellow. (FIG. 4B) Illustration for the creation of two new mutants (SS1(ST) and SS1(HP)). (FIG. 4C) The CFPS yields and soluble yields after dialysis against buffer with 0.5 M NaCl or 1.5 M NaCl. (FIG. 4D) SEC analysis after dialysis against buffer with 0.5 M NaCl or 1.5 M NaCl. (FIG. 4E) Testing different conjugation sites on the SS1(HP) protein spike tip. Six different nnAA sites (N75AHA, L76AHA, Q77AHA, D78AHA, Q79AHA, and A80AHA) were selected. (FIG. 4F) The soluble CFPS yields and soluble yields after 1.5M NaCl dialysis. (FIG. 4G) The TEM image of HBc SS1(HP) 78AHA VLP. (FIG. 4H) The reducing SDS-PAGE autoradiogram analysis of click-reaction products of HBc SS1(HP) VLP with flagellin, GMCSF, IM9-ScFv and CpG DNA. Cu(I) was not added to the control reaction.

FIG. 5 CFPS yields of mutants HBc(D78M), HBc(ST) and HBc(HP). HBc(D78M), HBc(ST), and HBc(HP) were stabilized by introducing new disulfide bridges (D29C-R127C).

FIG. 6A-6G. Transplant of the spike region of natural mutant Q8B6N7 to P03147. (FIG. 6A) The alignment of protein sequences (P03147 (SEQ ID NO: 32)and Q8B6N7) (SEQ ID NO: 105)) . The differences are highlighted in pink. HBc protein (UniProt accession number: P03147) was originally used in this study. (FIG. 6B) The non-reducing SDS-PAGE and the autoradiogram analysis after the oxidization treatment of purified VLPs. Diamide was used as the oxidant. (FIG. 6C) Sucrose gradient centrifugation analysis of oxidized VLPs. (FIG. 6D) SEC analysis after dialysis against buffer with 1.5 M NaCl. Six different nnAA sites (N75AHA, L76AHA, Q77AHA, D78AHA, Q79AHA, and A80AHA) were selected on the spike tip of mutant HBc (HP). (FIG. 6E) The non-reducing SDS-PAGE and the autoradiogram analysis after the oxidization treatment of purified VLPs. Diamide was used as the oxidant. (FIG. 6F) Synthesis of HBc HP 78AHA VLP with disulfide bridges. Ten positions were selected and compared, including SS1 (D29C-R127C), SS2 (T109C-V120C), SS3 (Y132C-N136C), SS4 (Y132C-A137C), SS5 (R133C-N136C), SS6 (R133C-A137C), SS7 (P134C-P135C), SS8 (P134C-N136C), SS9 (P134C-A137C), SS10 (P135C-N136C). Separation of VLPs by size-exclusion chromatography (SEC) using 10 mM Tris-HCl buffer (pH 7.4) with 1.5 M NaCl. The mutants SS3, SS4, SS5, and SS6 might affect the interactions between HBc monomer or dimers, so that they could not self-assemble into VLPs very well. (FIG. 6G) The non-reducing SDS-PAGE and the autoradiogram analysis after the oxidization treatment of purified VLPs. The SEC fractions 8-13 were pooled as the purified VLPs. Diamide was used as the oxidant. Only SS1 particles all stayed in the well of SDS-PAGE gel, which demonstrated that all S—S bonds were formed in SS1 VLPs. Based on these results, mutant SS1 is a preferred embodiment of the invention. Mutants SS8 and SS10 are other preferred embodiments of the invention.

FIG. 7A-7F. The CFPS protein yields, SEC profiles and click-reaction results of HBc VLP mutants with reduced negative surface charges. (FIG. 7A) The charge distribution of the HBc VLP surface at physiological pH, the distribution of charged amino acids in the dimer spike, and mutations for reducing or removing the negative charges of the HBc VLP surface. Different AHA sites on the dimer spike were also evaluated. All of these mutations were based on mutant SS1. (FIG. 7B) Illustration of HBc VLP conjugation with desired surface additions. Negatively charged molecules are less suitable for conjugation to this VLP. (FIG. 7C) The SEC profiles after dialysis against buffer with 0.5 M NaCl. (FIG. 7D) SEC results after dialysis against 1.5 M NaCl. (FIG. 7E) The surface charge distribution of the four attachment molecules at physiological pH and the position of the non-natural amino acid (nnAA) with an alkyne moiety. (FIG. 7F) The reducing SDS-PAGE autoradiograms of the click-reaction products. The column labels refer to the VLPs listed in part A.

FIG. 8A-8F. Optimization of CFPS conditions for improving the soluble CFPS yields and the VLP assembly of HBc mutants. (FIG. 8A) The CFPS yields and soluble yields after dialysis against buffer with 0.5 M NaCl. (FIG. 8B) Effects of potassium glutamate concentration on the CFPS yields of different mutants. The potassium glutamate concentration in standard CFPS system is 175 mM. (FIG. 8C) Effects of Mg2+concentration on the CFPS yield of the mutant B1 (D78AHA) at different potassium glutamate concentrations. The Mg2+ concentration in standard CFPS system is 16 mM. (FIG. 8D) Effects of temperature and the addition of detergent on the CFPS yields of different mutants. Addition of the detergent Brij 35 improved the soluble yield greatly. (FIG. 8E) Effects of Brij 35 concentration on the CFPS yield of the mutant B1 (D78AHA). The HBc protein was completely soluble when the Brij 35 concentration in the CFPS system was above 0.05% (w/v). (FIG. 8F) Sucrose gradient centrifugation (SGC) analysis of HBc protein (mutant B1 (D78AHA)) from the CFPS system with 0.05% (w/v) Brij 35. The results showed that Brij 35 improved the soluble yield but disrupted the VLP assembly.

FIG. 9A-9D. Optimization of dialysis conditions for improving the soluble yield and the VLP assembly of HBc mutants. (FIG. 9A) The procedure for the CFPS, dialysis, SEC and S—S bond formation. The dialysis after CFPS is a key step for the HBc protein folding and VLP assembly. The dialysis buffer is 10 mM Tris-HCl, pH 7.4, 0.5 M NaCl. (FIG. 9B) Effects of dialysis temperature on the soluble yield of the mutant B1 (D78AHA). The standard temperature in the dialysis step is 4° C. Higher dialysis temperature (37° C.) decreased the solubility of HBc protein. (FIG. 9C) Effects of pH of dialysis buffer on the soluble yield of the mutant B1 (D78AHA) and B2 (D78AHA+E77S). The standard pH of the dialysis buffer is 7.4. The pH 7.4 was still the best. (FIG. 9D) SEC analysis of the CFPS product after the dialysis at different pH values. The SEC running buffer was the same as the dialysis buffer. pH did not affect the VLP assembly.

(FIG. 10A) Salts in Hofmeister series. (FIG. 10B) Effects of different salts (Na2SO4, K2SO4, (NH4)2SO4, Na2HPO4 and NaCl) on the solubility of HBc mutants. (FIG. 10C) Effects of different concentrations of Na2SO4. The analyses of solubility after dialysis and size-exclusion chromatography (SEC) showed that Na2SO4 could improve the solubility a little but disrupt the VLP assembly. (FIG. 10D) Effects of different concentrations of KSCN. The analyses of solubility after dialysis, size-exclusion chromatography (SEC), and sucrose gradient centrifugation (SGC) showed that KSCN denatured the HBc antigen protein.

FIG. 11A-11C. Effects of amino acid salts and polyacrylic acid (PAA) on the solubility and the VLP assembly of HBc mutants (B1 (D78AHA), B2 (D78AHA+E77S), and C6 (P79AHA+E77S+D78S)). We used 10 mM Tris-HCl (pH 7.4) buffer with different salts in the dialysis step after CFPS. (FIG. 11A) Effects of arginine. The arginine (0.5 M) was added in the dialysis buffer and the pH was adjusted to 7.4. When pH is 7.4, arginine is positively charged, which might affect the assembly of HBc VLP. (FIG. 11B) Effects of salts of glutamic acid and aspartic acid. The glutamic acid (5 mM) and aspartic acid (5 mM) were added in the dialysis buffer and the pH was adjusted to 7.4. When pH is 7.4, glutamic acid and aspartic acid are negatively charged, which might affect the assembly of HBc VLP. (FIG. 11C) Effects of PAA. PAA is thought to be able to induce the HBc VLP assembly (Newman et al., 2009). The PAA (1 g/L) was added in the dialysis buffer and the pH was adjusted to 7.4. The analyses of solubility after dialysis and size-exclusion chromatography (SEC) showed that addition of amino acid salts and PAA almost had no effect on the solubility and the VLP assembly of HBc mutants.

FIG. 12A-12D. Effects of mutation F97L and different disulfide bond networks on the solubility and the VLP assembly of HBc mutants (B1 (D78AHA), B2 (D78AHA+E77S), and C6 (P79AHA+E77S+D78S)). We used 10 mM Tris-HCl (pH 7.4) buffer with two different NaCl concentrations (0.5 M and 1.5 M) in the dialysis step after CFPS. Three different disulfide bond networks were tried, including SS1 (D29C-R127C), SS8 (P134C-N136C) and SS10 (P135C-N136C). (FIG. 12A) Position of mutation F97L in the HBc dimer. In chronic hepatitis B virus (HBV) infections, one of the most common mutations to the virus occurs at amino acid 97, where leucine (FIG. 12L) replaces phenylalanine (FIG. 12F). Residue 97 is located in a hydrophobic pocket in the middle of the four-helix assembly. Its mutation could affect virus assembly thermodynamics and kinetics (Ceres et al., 2004). (FIG. 12B) SEC analysis for the mutant b1 with newly introduced mutations. (FIG. 12C) SEC analysis for the mutant b2 with newly introduced mutations. (FIG. 12D) SEC analysis for the mutant c6 with newly introduced mutations. The SEC analysis results demonstrated that introduction of F97L and different S—S bonds did not significantly improve the VLP assembly of mutants B1, B2, and C6.

(FIG. 13A) The refolding procedure. (FIG. 13B) The soluble percentage in the final 7 different dialysis buffers after protein refolding. (FIG. 13C) The SEC analysis of soluble refolded proteins. The running buffers were the same as the dialysis buffers. The results showed that the protein refolding was not effective.

FIG. 14A-14C. Sequence alignment of Hepatitis core proteins. (FIG. 14A) Sequence alignment of the Hepatitis core protein family PF00906 from the Pfam protein domain database (Punta et al., 2012). We started with the seed alignment which contained 12 members and removed 4 members not from human host. Of the remaining 8 sequences, none of the seed sequences had both negative charges removed (E77, D78) but one sequence, Q8B6N7 had a mutation at E77. The Q8B6N7 mutant was fairly novel. Comparing it to the rest of around 7000 members of PF00906, it was the only one with its series of mutations in the spike domain. The SEQ ID NOs for the 8 aligned sequences (top to bottom) are (SEQ ID NOs: 111-118), respectively. (FIG. 14B) Twelve sequences for the seed alignment of the Hepatitis core protein sequences using the Hepatitis core family PF00906 from Pfam protein domain database. (FIG. 14C) Natural HBc protein mutants with mutations at position 77. The amino acid at the position 77 in original HBc protein is Glutamic acid (FIG. 14E). The net negative charges on the dimer spike are from E77 and D78. D78 is conserved in all natural HBc mutants.

FIG. 15A-15B. Importance of electrostatic repulsion on HBc VLP assembly for wild type (P03147) and HP spike (Q8B6N7) variants. (FIG. 15A) The radar charts summarize the effects of spike tip charges on HBc solubility and VLP assembly at different NaCl concentrations. (FIG. 15B) Intradimer hydrophobic interactions in HBc wild-type (WT) (SEQ ID NO: 106)and HBc HP (SEQ ID NO: 107). The same amino acid sequences between HBc WT and HBc HP were marked as grey color in the structures. The amino acid sequences of the hydrophobic pockets are shown below the structure.

(FIG. 16A) The main core antigenic loop (red color) at the tip of HBc dimer. (FIG. 16B) ELISA assay of HBc VLPs with antibody C1-5. (FIG. 16C) ELISA assay of mice sera for evaluating the B-cell response. (D) Lymphocyte proliferation assay for evaluating the T-cell response.

(FIG. 17B) Reduced SDS Page gel—Comparing SEC purified assembled VLP and purified monomers.

FIG. 18 shows a representative SEC profile from one of the triplicate runs. The load on this column was 23.9 μg.

DETAILED DESCRIPTION OF THE EMBODIMENTS

Figure 5:
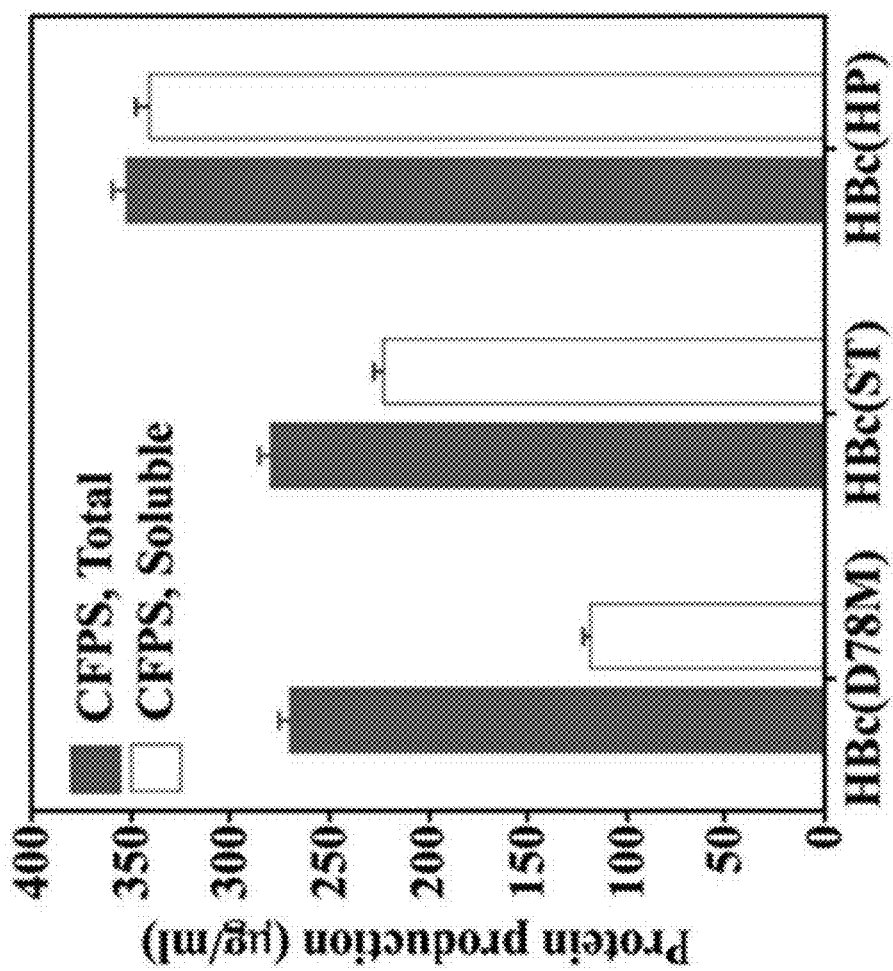
Figures 10A, 10B, 10C, 10D:
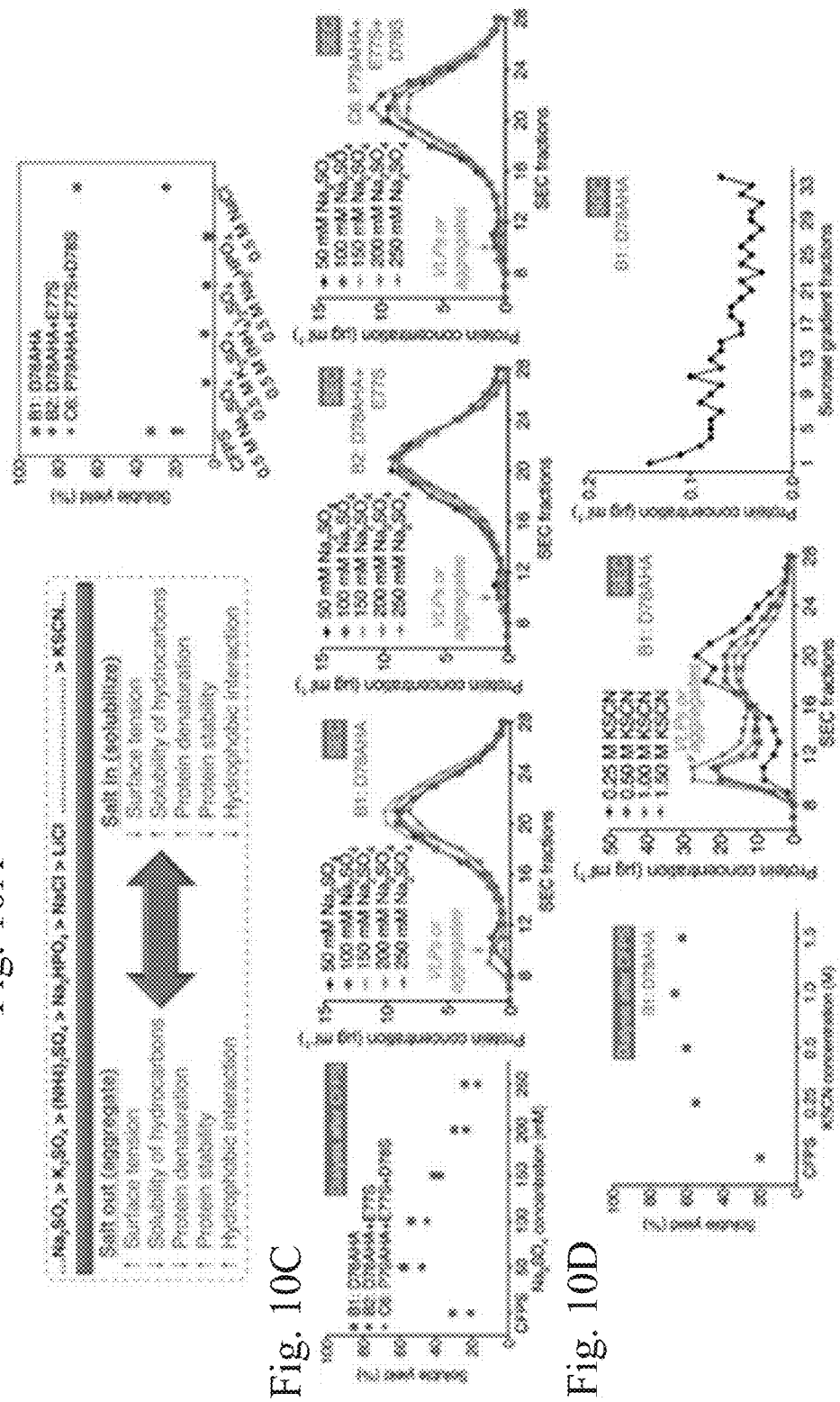
FIG. 10A-10D. Effects of salts on the solubility and the VLP assembly of HBc mutants (B1 (D78AHA), B2 (D78AHA+E77S), and C6 (P79AHA+E77S+D78S)). We used 10 mM Tris-HCl (pH 7.4) buffer with different salts in the dialysis step after CFPS.
Figure 13B:
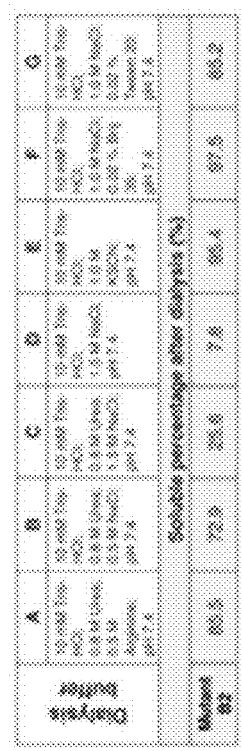
FIG. 13A-13C. Refolding of insoluble HBc protein mutant B2 (D78AHA+E77S) after CFPS reaction.
Figure 13C:
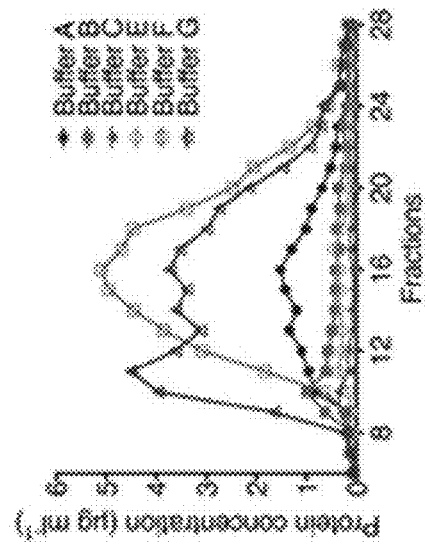
Figure 13A:
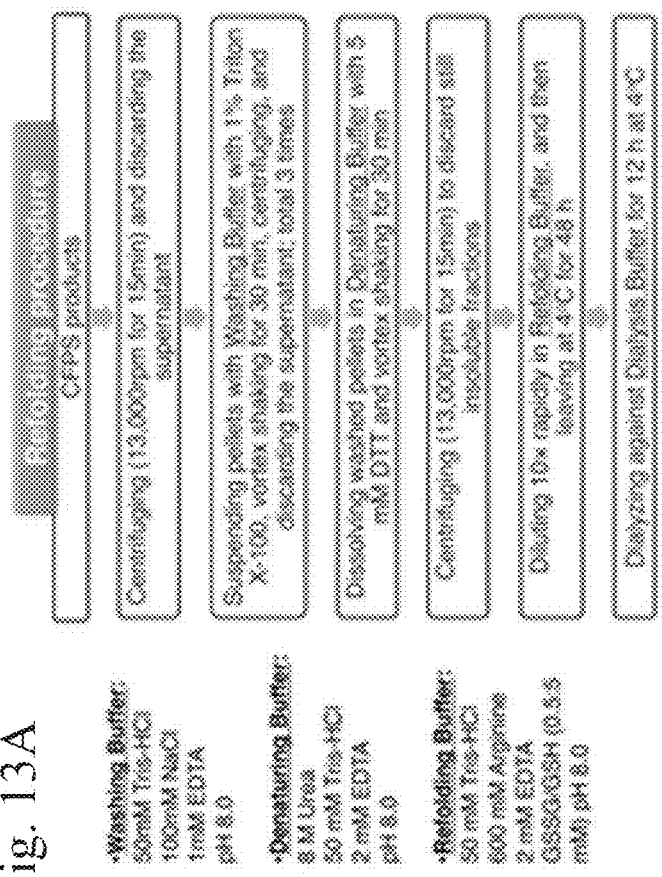

Genetically modified hepatitis B core (HBc) proteins are provided, which proteins comprise sequence modification that enhance the stability and/or utility of the protein. In some embodiments HBc polypeptides are provided in which the structure is stabilized by disulfide bonds. The substituted HBc protein is thus stabilized and is maintained as a VLP under conditions otherwise unfavorable to retention of the quaternary structure. In other embodiments, the amino acid sequence of an HBc protein comprises a set of amino acid substitutions that reduces the negative charge on the "spike tip" of the protein, i.e. the region of residues 74-81, relative to SEQ ID NO:1 or SEQ ID NO:2. In other embodiments an HBc protein comprises one or more unnatural amino acids at a pre-determined site, for example, N75, T74, L76, Q77, D78, Q79 and A80. In certain embodiments, an HBc protein of the invention comprises all three classes of modification: disulfide bond stabilization, negative charge reduction, and an unnatural amino acid at a pre-determined site.

The HBc polypeptides of the invention find particular use as a component of a VLP, and particularly a VLP designed for conjugation to one or more additional moieties through, for example, click chemistry. In some embodiments the unnatural amino acid is used to link the HBc protein to the additional moiety(s).

In some embodiments, the invention provides a use of a conjugate, compound, or composition herein in the manufacture of a medicament. In an embodiment, the invention provides a use of a conjugate, compound, or composition herein in the manufacture of a medicament, e.g. a vaccine, for the prevention or treatment of an infection. In some embodiments, the invention provides a use of a conjugate, compound, or composition herein for the prevention or treatment of an infection.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

The term "HBc" refers to the amino acid peptide sequence of the Hepatitis B core protein, or to a truncated version thereof as set forth in SEQ ID NO:1 or SEQ ID NO:2, or a comparable protein, for example as set forth in any one of SEQ ID NO:3-SEQ ID NO:52. One of skill in the art will understand that minor amino acid changes can be made in the sequence without altering the function of the protein, e.g. changes of 1, 2, 3, 4, 5, 6, 7, 8, 9, or up to about 10 amino acids, and that a full-length protein may be substituted for the truncated versions exemplified herein. HBc is functionally capable of self-assembling to form an icosahedral virus like particle. The HBc polypeptides of the invention comprise amino acid substitutions as described above, which include one or more of: (a) introducing one or more pairs of cysteine residues capable of forming intermolecular disulfide bonds when assembled into a VLP; (b) one or more unnatural amino acids at a predetermined site, preferably those capable of participating in a click chemistry reaction; and (c) one or more amino acid substitutions to decrease the negative charge of the proteins.

As used herein, the terms "purified" and "isolated" when used in the context of a polypeptide that is substantially free of contaminating materials from the material from which it was obtained, e.g. cellular materials, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide that is chemically synthesized refers to a polypeptide which is substantially free of chemical precursors or other chemicals which are involved in the syntheses of the polypeptide.

The term "polypeptide," "peptide," "oligopeptide," and "protein," are used interchangeably herein, and refer to a polymeric form of amino acids of any length, which can include coded and non-coded amino acids, chemically, or biochemically modified or derivatized amino acids, and polypeptides having modified peptide backbones.

The polypeptides may be isolated and purified in accordance with conventional methods of recombinant synthesis or cell free protein synthesis. Exemplary coding sequences are provided, however one of skill in the art can readily design a suitable coding sequence based on the provided amino acid sequences. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided in autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

As used herein, the term "virus like particle" refers to a stable macromolecular assembly of one or more virus proteins, usually viral coat proteins. The number of separate protein chains in a VLP will usually be at least about 60 proteins, about 80 proteins, at least about 120 proteins, or more, depending on the specific viral geometry. In the methods of the invention, the HBc is maintained in conditions permissive for self-assembly into the capsid structure, particularly reducing conditions. The methods of the invention provide for synthesis of the coat protein in the absence of the virus polynucleotide genome, and thus the capsid may be empty, or contain non-viral components, e.g. mRNA fragments, etc.

A stable VLP maintains the association of proteins in a capsid structure under physiological conditions for extended periods of time, e.g. for at least about 24 hrs, at least about 1 week, at least about 1 month, or more. Once assembled, the VLP can have a stability commensurate with the native virus particle, e.g. upon exposure to pH changes, heat, freezing, ionic changes, etc. Additional components of VLPs, as known in the art, can be included within or disposed on the VLP. VLPs do not contain intact viral nucleic acids, and they are non-infectious.

An "effective amount" or a "sufficient amount" of a substance is that amount sufficient to cause a desired biological effect, such as beneficial results, including clinical results, and, as such, an "effective amount" depends upon the context in which it is being applied. In the context of this invention, an example of an effective amount of a vaccine is an amount sufficient to induce an immune response (e.g., antibody production) in an individual. An effective amount can be administered in one or more administrations.

Folding, as used herein, refers to the process of forming the three-dimensional structure of polypeptides and proteins, where interactions between amino acid residues act to stabilize the structure. Non-covalent interactions are important in determining structure, and the effect of membrane contacts with the protein may be important for the correct structure. For naturally occurring proteins and polypeptides or derivatives and variants thereof, the result of proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

Separation procedures of interest include affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural biospecific binding of one molecular species to separate and purify a second species from a mixture. Antibodies are commonly used in affinity chromatography. Preferably a microsphere or matrix is used as the support for affinity chromatography. Such supports are known in the art and are commercially available, and include activated supports that can be combined to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

Proteins may also be separated by ion exchange chromatography, and/or concentrated, filtered, dialyzed, etc., using methods known in the art. The methods of the present invention provide for proteins containing unnatural amino acids that have biological activity comparable to the native protein. One may determine the specific activity of a protein in a composition by determining the level of activity in a functional assay, quantitating the amount of protein present in a non-functional assay, e.g. immunostaining, ELISA, quantitation on coomassie or silver stained gel, etc., and determining the ratio of biologically active protein to total protein. Generally, the specific activity as thus defined will be at least about 5% that of the native protein, usually at least about 10% that of the native protein, and may be about 25%, about 50%, about 90% or greater.

A modified HBc protein of the invention will usually comprise at least one unnatural amino acid at a pre-determined site, and may comprise or contain 1, 2, 3, 4, 5 or more unnatural amino acids. If present at two or more sites in the polypeptide, the unnatural amino acids can be the same or different. Where the unnatural amino acids are different, an orthogonal tRNA and cognate tRNA synthetase will be present for each unnatural amino acid.

Examples of unnatural amino acids that can be used in the methods of the invention include: an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an a,a disubstituted amino acid; a β-amino acid; a cyclic amino acid other than proline, etc.

Unnatural amino acids of interest include, without limitation, amino acids that provide a reactant group for CLICK chemistry reactions (see *Click Chemistry: Diverse Chemical Function from a Few Good Reactions* Hartmuth C. Kolb, M. G. Finn, K. Barry Sharpless Angewandte Chemie International Edition Volume 40, 2001, P. 2004, herein specifically incorporated by reference). For example, the amino acids azidohomoalanine, p-acetyl-L-phenylalanine and p-azido-L-phenylalanine are of interest.

In some embodiments, the unnatural amino acid is introduced by global replacement of methionine on the protein, e.g. methionine can be left out of a cell-free reaction mixture, and substituted by from 0.25-2.5 mM azidohomoalanine (AHA). In such embodiments it is preferred to substitute natural methionines, e.g. M66, with a different amino acid.

Alternatively the unnatural amino acid is introduced by orthogonal components. Orthogonal components include a tRNA aminoacylated with an unnatural amino acid, where the orthogonal tRNA base pairs with a codon that is not normally associated with an amino acid, e.g. a stop codon; a 4 by codon, etc. The reaction mixture may further comprise a tRNA synthetase capable of aminoacylating (with an unnatural amino acid) the cognate orthogonal tRNA. Such components are known in the art, for example as described in U.S. Pat. No. 7,045,337, issued May 16, 2006. The orthogonal tRNA recognizes a selector codon, which may be nonsense codons, such as, stop codons, e.g., amber, ochre, and opal codons; four or more base codons; codons derived from natural or unnatural base pairs and the like. The orthogonal tRNA anticodon loop recognizes the selector codon on the mRNA and incorporates the unnatural amino acid at this site in the polypeptide.

Orthogonal tRNA synthetase can be synthesized exogenously, purified and added to the reaction mix of the invention, usually in a defined quantity, of at least about 10 µg/ml, at least about 20 µg/ml, at least about 30 µg/ml, and not more than about 200 µg/ml. The protein may be synthesized in bacterial or eukaryotic cells and purified, e.g. by affinity chromatography, PAGE, gel exclusion chromatography, reverse phase chromatography, and the like, as known in the art.

The terms "conjugation partner" or "selected additional moiety(s)" are used interchangeably and refer generally to any moiety, for example a peptide or protein, nucleic acid, polysaccharide, label, etc. that is conjugated to a HBc polypeptide of the invention. The conjugation partner may comprise a complementary active group for CLICK chemistry conjugation to the HBc polypeptide of the invention. For example, it may be synthesized with one or more unnatural amino acids, which allow for the conjugation to the unnatural amino acid present on the HBc protein. One of skill in the art will understand that the chemistry for conjugation is well-known and can be readily applied to a variety of groups, e.g. CpG, detectable label, antigen, polypeptide, etc.

In some embodiments the conjugation partner is a structural protein, e.g. a collagen, keratin, actin, myosin, elastin, fibrillin, lamin, etc. In some embodiments the conjugation partner is an immunogen, e.g. a pathogen protein useful in immunization, including without limitation influenza proteins such as hemagglutinin. Virus coat proteins of interest include any of the known virus types, e.g. dsDNA viruses, such as smallpox (variola); vaccinia; herpesviruses including varicella-zoster; HSV1, HSV2, KSVH, CMV, EBV; adenovirus; hepatitis B virus; SV40; T even phages such as T4 phage, T2 phage; lambda phage; etc. Single stranded DNA viruses include phiX-174; adeno-associated virus, etc. Negative-stranded RNA viruses include measles virus; mumps virus; respiratory syncytial virus (RSV); parainfluenza viruses (PIV); metapneumovirus; rabies virus; Ebola virus; influenza virus; etc. Positive-stranded RNA viruses include polioviruses; rhinoviruses; coronaviruses; rubella; yellow fever virus; West Nile virus; dengue fever viruses; equine encephalitis viruses; hepatitis A and hepatitis C viruses; tobacco mosaic virus (TMV); etc. Double-stranded RNA viruses include reovirus; etc. Retroviruses include rous sarcoma virus; lentivirus such as HIV-1 and HIV-2; etc.

Examples of polypeptides suitable as conjugation partner include, but are not limited to, antigenic proteins such as tumor antigens, viral proteins, bacterial proteins, including tuberculosis antigens, protozoan proteins, including malarial proteins, renin; growth hormones, including human growth hormone; bovine growth hormone; growth hormone releasing factor; parathyroid hormone; thyroid stimulating hormone; lipoproteins; alpha-1-antitrypsin; insulin A-chain; insulin; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES and other chemokines; human macrophage inflammatory protein (MIP-1α); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3,-4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-α and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-18; superoxide dismutase; T-cell receptors; surface membrane proteins; decay accelerating factor; viral antigen such as, for example, a portion of the AIDS envelope; transport proteins; homing receptors; addressins; regulatory proteins; antibodies particularly single chain Fv antibodies; and fragments of any of the above-listed polypeptides.

Cell free protein synthesis, as used herein, refers to the cell-free synthesis of polypeptides in a reaction mix comprising biological extracts and/or defined reagents. The reaction mix will comprise a template for production of the macromolecule, e.g. DNA, mRNA, etc.; monomers for the macromolecule to be synthesized, e.g. amino acids, nucleotides, etc., and such co-factors, enzymes and other reagents that are necessary for the synthesis, e.g. ribosomes, tRNA, polymerases, transcriptional factors, etc. Such synthetic reaction systems are well-known in the art, and have been described in the literature. The cell free synthesis reaction may be performed as batch, continuous flow, or semi-continuous flow, as known in the art.

The CFPS and other subsequent steps may be performed under reducing conditions, e.g. in the presence of 1 mM DTT or the equivalent. Following assembly of the VLP the conditions may be changed to an oxidizing environment, e.g. by dialysis to remove the reducing agent, optionally in the presence of a salt, e.g. up to about 1M salt, up to about 1.5M salt, up to about 2 M salt, e.g. NaCl, etc., then oxidizing to form disulfide bonds by adding 5-10 mM $H_2O_2$, 5-10 mM diamide, or the equivalent.

In some embodiments of the invention, cell free synthesis is performed in a reaction where oxidative phosphorylation is activated, e.g. the CYTOMIM™ system. The activation of the respiratory chain and oxidative phosphorylation is evidenced by an increase of polypeptide synthesis in the presence of $O_2$. In reactions where oxidative phosphorylation is activated, the overall polypeptide synthesis in presence of $O_2$ is reduced by at least about 40% in the presence of a specific electron transport chain inhibitor, such as HQNO, or in the absence of $O_2$. The reaction chemistry may be as described in international patent application WO 2004/016778, herein incorporated by reference.

The CYTOMIM™ environment for synthesis utilizes cell extracts derived from bacterial cells grown in medium containing glucose and phosphate, where the glucose is present initially at a concentration of at least about 0.25% (weight/volume), more usually at least about 1%; and usually not more than about 4%, more usually not more than about 2%. An example of such media is 2YTPG medium, however one of skill in the art will appreciate that many culture media can be adapted for this purpose, as there are many published media suitable for the growth of bacteria such as E. coli, using both defined and undefined sources of nutrients (see Sambrook, J., E. F. Fritsch, and T. Maniatis. 1989. Molecular Cloning: A Laboratory Manual, $2^{nd}$ edition. Cold Spring Harbor University Press, Cold Spring Harbor, NY for examples of glucose containing media). Alternatively, the culture may be grown using a protocol in which the glucose is continually fed as required to maintain a high growth rate in either a defined or complex growth medium. The reaction mixture may be supplemented by the inclusion of vesicles, e.g. an inner membrane vesicle solution. Where provided, such vesicles may comprise from about 0 to about 0.5 volumes, usually from about 0.1 to about 0.4 volumes.

In some embodiments, PEG will be present in not more than trace amounts, for example less than 0.1%, and may be less than 0.01%. Reactions that are substantially free of PEG contain sufficiently low levels of PEG that, for example, oxidative phosphorylation is not PEG-inhibited. The molecules spermidine and putrescine may be used in the place of PEG. Spermine or spermidine is present at a concentration of at least about 0.5 mM, usually at least about 1 mM, preferably about 1.5 mM, and not more than about 2.5 mM. Putrescine is present at a concentration of at least about 0.5 mM, preferably at least about 1 mM, preferably about 1.5 mM, and not more than about 2.5 mM. The spermidine and/or putrescine may be present in the initial cell extract or may be separately added.

The concentration of magnesium in the reaction mixture affects the overall synthesis. Often there is magnesium present in the cell extracts, which may then be adjusted with additional magnesium to optimize the concentration. Sources of magnesium salts useful in such methods are known in the art. In one embodiment of the invention, the source of magnesium is magnesium glutamate. A preferred concentration of magnesium is at least about 5 mM, usually at least about 10 mM, and preferably a least about 12 mM; and at a concentration of not more than about 25 mM, usually not more than about 20 mM. Other changes that may enhance synthesis or reduce cost include the omission of HEPES buffer and phosphoenol pyruvate from the reaction mixture.

The system can be run under aerobic and anaerobic conditions. Oxygen may be supplied, particularly for reactions larger than 15 µl, in order to increase synthesis yields.

The headspace of the reaction chamber can be filled with oxygen; oxygen may be infused into the reaction mixture; etc. Oxygen can be supplied continuously or the headspace of the reaction chamber can be refilled during the course of protein expression for longer reaction times. Other electron acceptors, such as nitrate, sulfate, or fumarate may also be supplied in conjunction with preparing cell extracts so that the required enzymes are active in the cell extract.

It is not necessary to add exogenous cofactors for activation of oxidative phosphorylation. Compounds such as nicotinamide adenine dinucleotide (NADH), NAD$^+$, or acetyl-coenzyme A may be used to supplement protein synthesis yields but are not required. Addition of oxalic acid, a metabolic inhibitor of phosphoenolpyruvate synthetase (Pps), may be beneficial in increasing protein yields, but is not necessary.

The template for cell-free protein synthesis can be either mRNA or DNA, preferably a combined system continuously generates mRNA from a DNA template with a recognizable promoter. Either an endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Other salts, particularly those that are biologically relevant, such as manganese, may also be added. Potassium is generally present at a concentration of at least about 50 mM, and not more than about 250 mM. Ammonium may be present, usually at a concentration of not more than 200 mM, more usually at a concentration of not more than about 100 mM. Usually, the reaction is maintained in the range of about pH 5-10 and a temperature of about 20°-50° C.; more usually, in the range of about pH 6-9 and a temperature of about 25°-40° C. These ranges may be extended for specific conditions of interest.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Polypeptides

HBc polypeptides are provided in which the quaternary structure is stabilized by the introduction of cysteine residues that form intermolecular disulfide bonds. Polypeptides of the invention comprise an HBc sequence, for example with reference to SEQ ID NO:1 or SEQ ID NO:2, wherein at least one pair of amino acids are substituted with cysteine, including substitutions of two pairs, three pairs, etc. In some embodiments the amino acid substitutions are selected from [D29C, R127C]; [T109C, V120C]; [Y132C, N136C]; [Y132C, A137C]; [R133C, N136C]; [R133C, A137C]; [P134C, P135C]; [P134C, N136C]; [P134C, A137C]; and [P135C, N136C]. In some embodiments the amino acid substitutions are D29C, R127C; P134C and N136C; or D29C, R127C, P134C and N136C. Amino acid sequences of interest include those set forth in the Examples, e.g. SEQ ID NO:3-SEQ ID NO:52.

In some embodiments HBc polypeptide comprises at least one unnatural amino acid at a pre-determined site, usually in combination with the introduction of cysteine residues as described above. The unnatural amino acid(s) may be positioned at the spike of the HBc protein. Sites of interest include, for example, N75, T74, L76, Q77, D78, Q79 and A80. In some embodiments the unnatural amino acid replaces D78. In some embodiments the unnatural amino acid is azidohomoalanine. In some embodiments the naturally occurring methionine at residue 66 is replaced with serine, M66S, and the unnatural amino acid is introduced by methionine substitution.

In other embodiments, the HBc protein alternatively or in addition comprises a set of amino acid substitutions that reduces the negative charge on the "spike tip" of the protein, i.e. , i.e. the region of residues 73-81, relative to SEQ ID NO:1 or SEQ ID NO:2. In some embodiments the set of amino acid substitutions is derived from a naturally occurring virus genotype with a reduced charge. Viral genotypes of interest for this purpose include Uniprot accession number Q8B6N7, provided herein for reference as SEQ ID NO:32.

In some embodiments, the set of amino acid changes, relative to SEQ ID NO:1 or SEQ ID NO:2 are I59V, L60S, G63R, D64E, L65V, M66T, T67D, L68F, A69G, T70D, T74N, L76M, E77Q, P79Q, S81A, S87N, T91A, V93I, and F97I. In some embodiments the set of amino acid changes is T74N, L76M, E77Q, P79Q, and S81A. In some embodiments, the amino acid sequence of the HBc protein with a reduced negative charge is SEQ ID NO:34 or SEQ ID NO:35, which sequences also comprise the optional substitutions of M66S, and D29C, R127C.

HBc polypeptides of interest include, without limitation, those comprising the set of amino acid substitutions, which may be made relative to SEQ ID NO:1, SEQ ID NO:2, etc.:
{D29C, R127C}; {P134C ,N136C}; or {D29C, R127C, P134C and N136C};
M66S
N75AHA, T74AHA, L76AHA, Q77AHA, D78AHA, Q79AHA or A80AHA
{I59V, L60S, G63R, D64E, L65V, M66T, T67D, L68F, A69G, T70D, T74N, L76M, E77Q, P79Q, S81A, S87N, T91A, V93I, F97I}; or {T74N, L76M, E77Q, P79Q, S81A}.

In certain embodiments the HBc polypeptides comprise the set of amino acid substitutions:
{D29C, R127C, P134C and N136C};
M66S
D78AHA
{I59V, L60S, G63R, D64E, L65V, M66T, T67D, L68F, A69G, T70D, T74N, L76M, E77Q, P79Q, S81A, S87N, T91A, V93I, F97I}.

In certain embodiments the HBc polypeptide is one of SEQ ID NO:3-SEQ ID NO:31, SEQ ID NO:34-SEQ ID NO:52. In some embodiments the HBc polypeptide is one of SEQ ID NO:39, SEQ ID NO:42, or SEQ ID NO:52.

In some embodiments of the invention, a monomeric form of the HBc polypeptide of the invention is provided. In other embodiments a dimeric form of the HBc polypeptide of the invention is provided. In some embodiments the HBc polypeptide is assembled into a VLP, that can be stabilized by intermolecular disulfide bonds upon oxidation.

If desired, various groups may be introduced into the peptide during synthesis or during expression, which allow for linking to other molecules or to a surface. The introduced groups need not be included in the HBc domain itself, but may be introduced as a tag or fusion C-terminal or N-terminal to the HBc domain. Thus cysteines can be used to make thioethers, histidines for linking to a metal ion complex, carboxyl groups for forming amides or esters, amino groups for forming amides, and the like. In some embodiments an unnatural amino acid is included at one or more defined sites in the protein, including without limitation.

The HBc polypeptides of the invention may include an unnatural amino acid for the control of direct attachment to a conjugation partner. Conjugation partners may have an active group for conjugation to the unnatural amino acid(s) on the HBc polypeptide. In some embodiments the conjugation partner is modified to comprise an unnatural amino acid, are reacted with a HBc polypeptide, usually a HBc polypeptide that also comprises an unnatural amino acid and that is assembled in a disulfide stabilized VLP. The unnatural amino acid on the conjugation partner is different from, and reactive with, the unnatural amino acid present on the HBc polypeptide(s). In one embodiment, at least 5%, at least 10%, at least 20%, at least 40%, at least 50%, at least 60%, at least 70%, at least 80% or at least 90% of the unnatural amino acids present on the HBc polypeptides are stably attached to a conjugation partner.

Where the active groups for conjugation are reactive azide and alkyne groups, the reaction between HBc and partner may by catalyzed with a copper(I) catalyst at a concentration sufficient for catalysis, e.g. at least about 1 µM, at least about 0.1 mM, at least about 1 mM, etc., as is known in the art. The reaction can be performed using commercial sources of copper(I) such as cuprous bromide or iodide or a compound such as tetrakis(acetonitrile)copper(I)hexafluorophosphate as long as the reaction is performed under anaerobic conditions. The reaction can be run in a variety of solvents, and mixtures of water and a variety of (partially) miscible organic solvents including alcohols, DMSO, DMF, tBuOH and acetone work well. The reaction will proceed at room temperature, and is allowed to proceed to the desired level of completion, e.g. at least about 15 minutes, at least about one hour, at least about 4 hours, at least about 8 hours, or more.

This invention additionally provides various modified, e.g., chimeric, HBc polypeptides. In one embodiment, the chimeric HBc polypeptide comprises sequences of (1) a first native HBc polypeptide and (2) an internal sequence from a second different HBc polypeptide. For example, at least two amino acids of the native HBc polypeptide may be substituted with cysteine residues that can form intermolecular disulfide bonds after the chimeric HBc is assembled into a VLP. In so doing, an artificial disulfide bond network is produced which stabilizes the VLP. Further, the internal sequence of the second, different HBc polypeptide may include a spike tip with a lower number of net negative charges at neutral pH than the corresponding portion of the native HBc polypeptide so replaced or substituted. The resulting chimeric HBc polypeptide thus possesses lower net negative charges at the spike tip than, e.g., the two net negative charges at neutral pH at the spike tip of a native HBc polypeptide or amino acid residues 74-81 of SEQ ID NO:1.

In accordance with the practice of the invention, the internal sequence include an HBc spike tip, an HBc hydrophobic pocket, or an HBc spike or a portion thereof. In an embodiment of the invention, the HBc spike tip includes residues 74-81 of SEQ ID NO:1.

In another embodiment, the sequences for the HBc spike tip, the HBc hydrophobic pocket, or the HBc spike is included in any of UniProt accession number: P0C692, O91532, Q4R1S0, O92920, P03149, P0C696, P0C698, Q9QBF2, P0C677, Q8AZ62, Q9WMW8, D2U608, D2U612, Q8B6N7, and Q9WMB7. For example, within those sequences, the HBc spike tip may be determined after sequence alignment with SEQ ID NO: 1 and may correspond to residues 74-81 of SEQ ID NO:1. In another example, the location of the HBc hydrophobic pocket may be determined after sequence alignment with SEQ ID NO:1 and may correspond to residues 59-97 of SEQ ID NO:1. In yet a further example, the location of the HBc spike may be determined after sequence alignment with SEQ ID NO: 1 and may correspond to residues 50-110 of SEQ ID NO:1.

Merely by way of example, the chimeric HBc polypeptide may have a sequence shown in any of SEQ ID Nos.: 34, 35, 36, 37, 38, 39, 40, 41, 42, 48, 49, 50, 51, and 52. In a preferred embodiment, the chimeric HBc polypeptide has a sequence as shown in SEQ ID NO:35. Additionally, in yet another embodiment, the chimeric HBc polypeptide may have any of the amino acid sequences encoded by the nucleic acid sequence designated as SS1(ST) or SS1(HP) of Table S2.

Additionally, in one embodiment of the invention, the two amino acids of the HBC polypeptide so substituted include any of D29-R127, T109-V120, P134-P135, P134-N136, P134-A137, and P135-N136 as shown in SEQ ID NO:1 or SEQ ID NO:2. Alternatively, the two amino acids so substituted can be any amino acid pair at corresponding positions of D29-R127, T109-V120, P134-P135, P134-N136, P134-A137, and P135-N136 as shown in SEQ ID NO:1 or SEQ ID NO:2 in aligned sequences of an HBc polypeptide.

The invention also provides HBc polypeptides further comprising a non-natural amino acid, preferably at the spike tip replacing a negatively charged amino acid with a neutral or lower charged amino acid at neutral pH. For example, at the spike tip, leucine at amino acid position 76 (L76) or aspartic acid at amino acid position 78 (D78) of SEQ ID NO: 1 or any amino acid at the same corresponding position for an HBc polypeptide differing in sequence, following sequence alignment with SEQ ID NO:1 may be replaced with azidohomoalanine, homopropargylglycine, p-propargyloxyphenylalanine or an unnatural amino acid that provides a reactant group for Click chemistry reaction.

Additionally provided as part of the invention are HBc polypeptides further comprising a non-methionine amino acid at residue 66 of SEQ ID NO:1 or equivalent position to residue 66 of SEQ ID NO:1.

In one embodiment, the HBc polypeptides further comprises a substitution of a cysteine at amino acid position 48, 61 or 107 of SEQ ID NO:1 or equivalent to position 48, 61 or 107 of SEQ ID NO:1 with a non-cysteine amino acid so as to further stabilize a VLP or reduce possibility of self-assembly to a VLP with T=3 icosahedral symmetry. In one example, the non-cysteine amino acid is a serine.

In yet another embodiment of the invention, in the HBc polypeptide so modified, the two amino acids so replaced or substituted are selected based on proximity between side chains of HBc dimers or proximity between C-terminal regions of HBc monomers forming both 5-fold units and 6-fold units of a VLP.

C-terminal regions of HBc monomers may extend from the very end of the carboxyl terminus to the mid-point of the HBc polypeptide in some embodiment and in other embodiments may describe any of the regions between the carboxyl terminus and the mid-point of the HBc polypeptide. For example, for a truncated HBc having the first 149 amino acids that can assemble into a VLP, the C-terminal regions may extend from residues at position 75-149 or any region encompassed by residues at position 75-149.

Further, the HBc polypeptide may be modified to contain a spike tip that has a lower negative charge than the -2 charge of the spike tip of SEQ ID NO:1 at neutral pH. For example, the lower negative charge may be achieved by substituting E77 of SEQ ID NO:1 with a non-negatively charged amino acid at neutral pH. Examples of non-negatively charged amino acids include, but are not limited to, glutamine, serine, and lysine. In another example, a lower negative charge is no net negative charge at neutral pH which may be achieved by substituting E77 and D78 of SEQ ID NO:1 with non-negatively charged amino acids. In a further example, E77 may be substituted with a glutamine and D78 may be substituted with either methionine, azidohomoalanine, homopropargylglycine or an unnatural amino acid that provides a reactant group for Click chemistry reaction. In one embodiment, azidohomoalanine, homopropargylglycine or an unnatural amino acid provides a reactant group for Click chemistry reaction at the spike tip.

The invention further provides nucleic acids encoding the HBc polypeptides of the invention. As will be appreciated by those in the art, due to the degeneracy of the genetic code, an extremely large number of nucleic acids may be made, all of which encode the HBc polypeptides of the present invention. Thus, having identified a particular amino acid sequence, those skilled in the art could make any number of different nucleic acids, by simply modifying the sequence of one or more codons in a way that does not change the amino acid sequence.

Using the nucleic acids of the present invention that encode a HBc polypeptide, a variety of expression constructs can be made. The expression constructs may be self-replicating extrachromosomal vectors or vectors which integrate into a host genome. Alternatively, for purposes of cell-free expression the construct may include those elements required for transcription and translation of the desired polypeptide, but may not include such elements as an origin of replication, selectable marker, etc. Cell-free constructs may be replicated in vitro, e.g. by PCR, and may comprise terminal sequences optimized for amplification reactions.

Generally, expression constructs include transcriptional and translational regulatory nucleic acid operably linked to the nucleic acid encoding the fusion protein. The term "control sequences" refers to DNA sequences necessary for the expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading phase. Linking is accomplished by ligation or through amplification reactions. Synthetic oligonucleotide adaptors or linkers may be used for linking sequences in accordance with conventional practice.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention. In a preferred embodiment, the promoters are strong promoters, allowing high expression in in vitro expression systems, such as the T7 promoter.

In addition, the expression construct may comprise additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Stablilized VLPs

The invention provides stabilized, virus like particles (VLPs) having an artificial disulfide bond network comprising multiple HBc polypeptides of the invention. In one embodiment, the network is formed under oxidizing condition following self-assembly of HBc polypeptides into a VLP under reducing condition, so as to produce correct or functional disulfide bond formation.

In another embodiment, the VLP contains multiple HBc polypeptides having at least two amino acids of each of the HBc polypeptides substituted with cysteine residues that can form interdimer disulfide bonds after the HBc is assembled into the VLP thereby forming the artificial disulfide bond network that stabilizes the VLP.

For example, the two amino acids so substituted may be located in the C-terminal half of each HBc polypeptide in a HBc dimer forming both a 5-fold unit and 6-fold unit of the VLP such that the VLP is stabilized through the C-terminal half of a capsid protein (also referred to herein as an HBc polypeptide) that forms the VLP. In one embodiment, the two amino acids of the HBc polypeptide so chosen for substitution may be located in proximity between HBc dimer interfaces forming both 5-fold units and 6-fold units of the VLP. In another example, the two amino acids of an HBc polypeptide so substituted are located in proximity between the C-terminal regions of HBc monomers forming both 5-fold units and 6-fold units of a VLP. Merely by way of example, the two amino acids may be within about 4 to 7 Angstroms of each other. In particular embodiments, the two amino acids of the HBC polypeptide of so substituted are D29-R127 as shown in SEQ ID NO:1 or SEQ ID NO:2; or an amino acid pair at the same corresponding positions for an HBc polypeptide without an aspartic acid at amino acid position 29 or arginine at amino acid position 127 following alignment of a different HBc polypeptide sequence to SEQ ID NO: 1 or SEQ ID NO: 2. In additional particular embodiments, the two amino acids of the HBC polypeptide so substituted are any of P134-P135, P134-N136, P134-A137, or P135-N136 as shown in SEQ ID NO:1 or SEQ ID NO:2 or an amino acid pair at the same corresponding positions for an HBc polypeptide differing in sequence, following sequence alignment with SEQ ID NO: 1 or SEQ ID NO: 2. In yet a further particular embodiment, the two amino acids of an HBC polypeptide selected for substitution are D29-R127 as provided in SEQ ID NO:1 or SEQ ID NO:2 or the same amino acid pairs at corresponding positions in aligned sequences of HBc polypeptides. In an alternative embodiment, the two amino acids of the HBc polypeptide so substituted are P134-N136 as shown in SEQ ID NO:1 or SEQ ID NO:2 or amino acid pair at the same corresponding positions for an HBc polypeptide differing in sequence, following sequence alignment with SEQ ID NO: 1 or SEQ ID NO: 2.

In another embodiment of the invention, the VLP is a stabilized chimeric VLP in that each of the HBc polypeptides of the VLP comprises a transplanted spike polypeptide sequence of an HBc polypeptide which is different from the spike polypeptides sequence of the wildtype HBc polypeptide. Further, two HBc polypeptides dimerize to form a spike. For example, the spike may include a hydrophobic pocket or portion thereof and a spike tip.

In one embodiment, the spike tip is an 8-amino acid sequence of SS1(ST) underlined in Table S2 starting with amino acid residue at position 74 and ending with amino acid sequence at position 81 of SEQ ID NO: 1 or UniProt accession number P03147 or equivalent thereof. In another embodiment, the spike tip is an 8-amino acid sequence starting with amino acid residue at position 103 and ending with amino acid residue at position 110 of UniProt accession number Q8B6N7 or equivalent thereof.

Figure 14A:
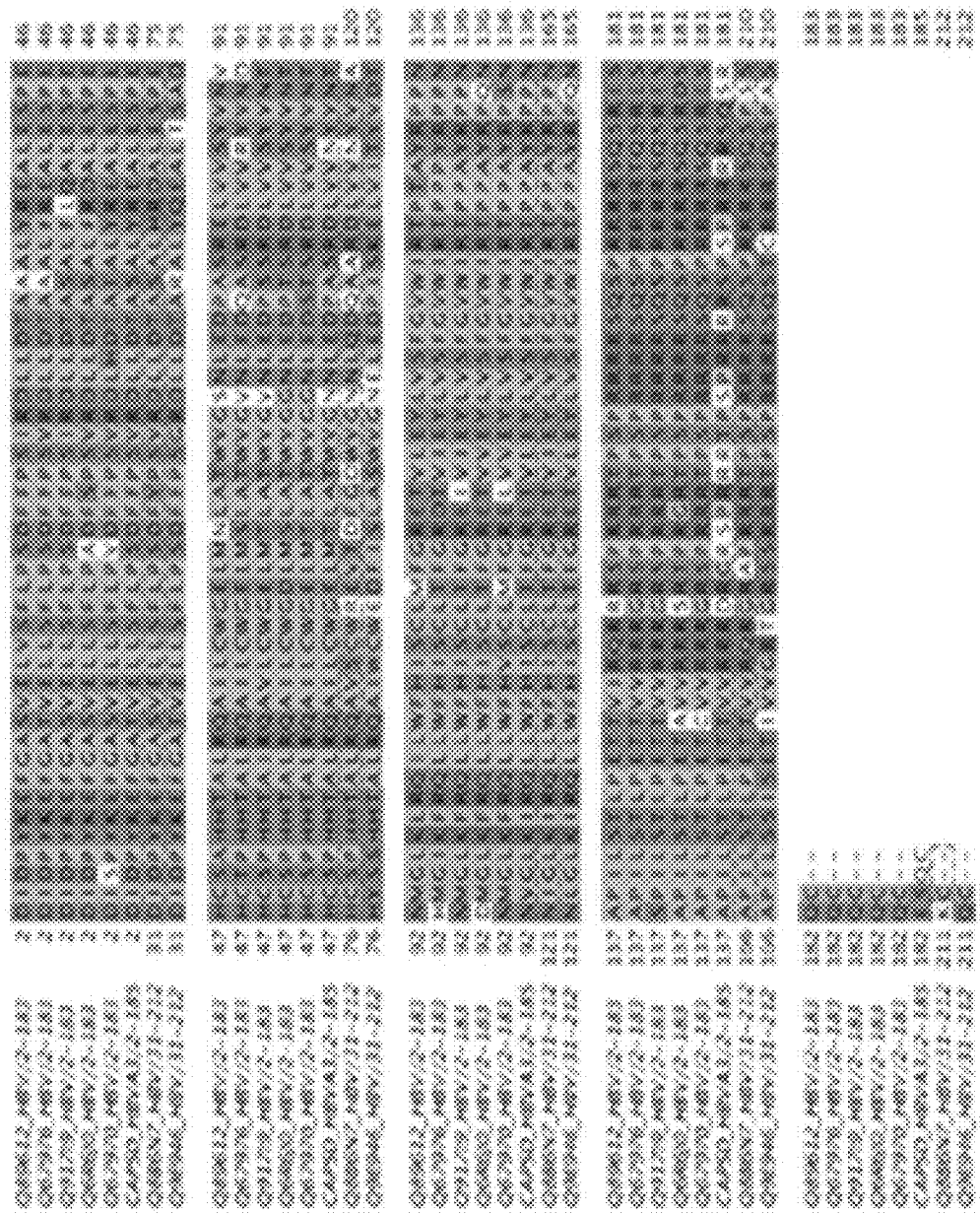

In yet another embodiment, amino acid residues equivalent to about position 74 to 81 of SEQ ID NO: 1 in aligned HBV sequences are shown in FIG. 14A beginning at about amino acid position 74 and ending at amino acid position 81 for the top six aligned HBV sequences or additional aligned HBV sequences or portions thereof corresponding to about position 74 to 81 of SEQ ID NO: 1 or UniProt accession number P03147 (FIG. 4A) and/or top six aligned HBV sequences shown in FIG. 14A. In a further embodiment, the amino acid residues equivalent to about position 103 to 110 of UniProt accession number Q8B6N7 (FIG. 4A) in aligned HBV sequences are shown in FIG. 14A beginning at about amino acid position 103 and ending at about amino acid position 110 for the bottom two aligned HBV sequences or additional aligned HBV sequences or portions thereof corresponding to about position 103 to 110 of UniProt accession number Q8B6N7 and/or bottom two aligned HBV sequences shown in FIG. 14A.

In another embodiment of the VLP of the invention, one or more or each of the HBc polypeptides comprises a spike sequence of an HBc polypeptide which has been modified to have a lower negative charge or neutral charge compared to the spike sequence of the wild-type HBc polypeptide at neutral pH.

In a further embodiment of the VLP of the invention, the spike sequence of the HBc polypeptide may include a sequence from the amino-to-carboxyl end of (1) twenty four amino acids that form a long alpha helix 3 (α3) with 6.4 alpha helical turns followed by (2) five amino acids that loop back joined to (3) thirty-two amino acids that form alpha helix 4 (α4) with a kink that breaks the alpha helix 4 at the thirteenth amino acid separating α4 into (i) twelve amino acids that form three alpha helical turns of alpha helix 4a (α4a) and (ii) nineteen amino acids that form five alpha helical turns of alpha helix 4b (α4b) which forms a hairpin structure and (b) participates in a 4-helix bundle in the HBc dimer, or portion thereof.

Examples of sequences forming alpha helix 3 (α3) to end of alpha helix 4b (α4b) includes, but are not limited to, a sequence starting with amino acid residue at position 50 and ending with amino acid residue at position 110 of SEQ ID NO: 1 of UniProt accession number P03147 or equivalent thereof; or a sequence starting with amino acid residue at position 79 and ending with amino acid residue at position 139 of UniProt accession number Q8B6N7 or equivalent thereof;

In one embodiment, the amino acid residues equivalent to position 50 to 110 of SEQ ID NO: 1 or UniProt accession number P03147 include any of the top six aligned HBV sequences shown in FIG. 14A beginning with amino acid residue at position 50 and ending with amino acid 110.

In another embodiment, amino acid residues equivalent to position 79 to 139 of UniProt accession number Q8B6N7 in aligned HBV sequences include any of the bottom two aligned HBV sequences shown in FIG. 14A beginning with amino acid residue at position 79 and ending with amino acid residue at 139 or additional aligned HBV sequences or portions thereof corresponding to position 79 to 139 of UniProt accession number Q8B6N7.

The hydrophobic pocket may include (a) a sequence beginning with about amino acid residue at position 59 and ending with about amino acid sequence at position 97 of SEQ ID NO: 1 or UniProt accession number P03147 or equivalent thereof;(b) a sequence beginning with about amino acid residue at position 88 and ending with about amino acid residue at position 126 of UniProt accession number Q8B6N7 or equivalent thereof; or (3) a 39-amino acid sequence of SS1(HP) as underlined and shown in Table S2. In one embodiment, amino acid residues equivalent to about position 59 to 97 of SEQ ID NO: 1 or UniProt accession number P03147 are shown in FIG. 14A beginning at about amino acid 59 and ending at about amino acid 97 for the top six aligned HBV sequences. In another embodiment, amino acid residues equivalent to position 59 to 97 of SEQ ID NO: 1 or UniProt accession number P03147 are shown in top six aligned HBV sequences shown in FIG. 14A. It would be understood and recognized by those skilled in the art that the hydrophobic pocket would include or encompass sequences as identified by the methods described herein that will allow proper folding and assembly into the stable VLPs of the invention.

In yet another embodiment, amino acid residues equivalent to position 88 and ending at amino acid position 126 of UniProt accession number Q8B6N7 are shown in FIG. 14A beginning at amino acid position 88 and ending at amino acid position 126 for the bottom two aligned HBV sequences or additional aligned HBV sequences or portions thereof corresponding to position 88 to 126 of UniProt accession number Q8B6N7. In yet another embodiment, amino acid residues equivalent to position 88 and ending at amino acid position 126 of UniProt accession number Q8B6N7 are shown in the bottom two aligned HBV sequences shown in FIG. 14A.

Merely by way of example, the stabilized VLP of the invention may have any of the sequences shown in SEQ ID No. 16, 17, 18, 19, 21, 22, 23, 24, 25, 27, 28, 29, 30, 31, 33, 34, 35, 36, 37, 38, 39, 40, 41, or amino acid sequence encoded by the nucleic acid sequence provided as: (i) B1, C2, C4, C5, D2, D4 or D5 of Table 1, or (ii) SS1(B1), SS1(ST), or SS1(HP) of Table S2.

Additionally, as an example, the aligned HBV sequences or portions thereof can be from any of the Hepatitis core family PF00906 sequences of the Pfam database, aligned HBc/HBV protein sequences from the UniProt database, aligned HBc/HBV protein sequences from a public database, GenBank database, European Nucleotide Archive database, and/or any alignment/aligned output of publically available HBc/HBV protein sequences or conceptually translated HBV protein sequences using a sequence alignment/search computer program.

Method For Making a Chimeric VLP

Additionally, the invention provides methods for making a chimeric VLP of the invention having a transplanted spike sequence or portion thereof. In one embodiment, the method comprises replacing a spike sequence of a first native HBc or portion thereof with a corresponding spike sequence or portion thereof, of a second, different HBc polypeptide comprising a different spike sequence, so as to produce a chimeric VLP coat or capsid protein. The method further comprises permitting the chimeric VLP coat protein to undergo self-assembly into a chimeric VLP, thereby making a chimeric VLP having a transplanted spike sequence or portion thereof. In an embodiment of the method of the invention, replacing the spike sequence or portion thereof in (a) is effected by replacing nucleic acid sequence encoding spike sequence with a nucleic acid sequence encoding a different spike sequence and producing the polypeptide encoded by the nucleic acid so as to produce a chimeric VLP coat or capsid protein.

In a further embodiment, the method comprises aligning amino acid sequences of VLP coat or capsid proteins; identifying amino acid sequence with a desired spike sequence or portion thereof from the aligned sequences; replacing nucleic acid sequence encoding a spike sequence or portion thereof of a VLP coat or capsid protein with nucleic acid sequence encoding the desired spike sequence or portion thereof so as to produce a nucleic acid sequence encoding a chimeric VLP coat or capsid protein with a transplanted spike sequence or portion thereof. The method further comprises producing the chimeric VLP coat or capsid protein with a transplanted spike sequence or portion thereof from the nucleic acid sequence. The chimeric VLP coat or capsid protein is then permitted to undergo self-assembly to form the chimeric VLP having a transplanted spike sequence or portion thereof.

In accordance with the practice of the invention, self-assembly in (e) may be performed under high salt condition. For example, the high salt condition may comprise greater than 0.5 M NaCl or equivalent, preferably around 1.5 M NaCl or equivalent.

Formulations and Uses

The HBc polypeptides, including VLP comprised of HBc; and monomers, dimers or VLPs comprising one or more conjugated moieties, may be provided in a pharmaceutically acceptable excipient, and may be in various formulations. As is well known in the art, a pharmaceutically acceptable excipient is a relatively inert substance that facilitates administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington's Pharmaceutical Sciences 19th Ed. Mack Publishing (1995).

Generally, these compositions are formulated for administration by injection or inhalation, e.g., intraperitoneally, intravenously, subcutaneously, intramuscularly, etc. Accordingly, these compositions are preferably combined with pharmaceutically acceptable vehicles such as saline, Ringer's solution, dextrose solution, and the like. The particular dosage regimen, i.e., dose, timing and repetition, will depend on the particular individual and that individual's medical history.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the reagents, cells, constructs, and methodologies that are described in the publications, and which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Stabilization and Modification of Hepatitis B Core (HBc) Virus-Like Particles (VLPs)

Materials and Methods

Plasmid construction. The sequence encoding the human Hepatitis B core (HBc) capsid monomer of subtype adyw (Pasek et al., 1979) with the C-terminus truncated at amino acid 149 was optimized for *E. coli* tRNA concentrations and was synthesized from oligonucleotides designed with DNAworks v3.0. The vector pET24a-HBc149 was generated by ligation (T4 DNA ligase, New England Biolabs, Ipswich, Mass.) of the optimized HBc protein gene into the pET-24a (+) vector (Novagen, San Diego, Calif.) at the Nde I and Xho I restriction sites. To incorporate methionine analogues, two mutations (M66S and L76M) were introduced. pET24a-HBc149-M66S-L76M was transformed into DH5a cells and the plasmid was purified with Qiagen Plasmid Maxi Kit (Qiagen, Valencia, Calif.) for use in cell-free protein synthesis (CFPS). All mutants were constructed using QuikChange PCR (Stratagene, La Jolla, Calif.).

Sequences of HBc protein variants. The sequences of 10 different variants with different cysteine mutations intended to stabilize the VLPs (Table 1):

TABLE 1

| Variants | Protein sequence | DNA encoding sequence |
|---|---|---|
| Wild-type (HBc149) | MDIDPYKEFGATVELLS FLPSDFFPSVRDLLDTA AALYRDALESPEHCSPH HTALRQAILCWGDLMTL ATWVGTNLEDPASRDL VVSYVNTNVGLKFRQLL WFHISCLTFGRETVLEY LVSFGVWIRTPPAYRPP NAPILSTLPETTVV (SEQ ID NO: 1) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGATGACCCTGGCGACTTGGGTTGGCACCA ACCTGGAAGATCCGGCTCTCGTGATCTGGTTGTTTCT TACGTTAACACTAACGTTGGTCTGAAATTCCGTCAGCT GCTGTGGTTCCACATCTCTTGCCTGACCTTCGGTCGTG AAACCGTTCTGGAATACCTGGTTTCTTTTGGTGTTTGG ATTCGTACTCCGCCGGCTTACCGTCCGCCGAACGCAC CGATCCTGAGCACCCTGCCGGAAACCACTGTTGTGTA ATAA (SEQ ID NO: 53) |
| Original (M66S-L76M) | MDIDPYKEFGATVELLS FLPSDFFPSVRDLLDTA AALYRDALESPEHCSPH HTALRQAILCWGDLSTL ATWVGTNMEDPASRDL VVSYVNTNVGLKFRQLL WFHISCLTFGRETVLEY LVSFGVWIRTPPAYRPP NAPILSTLPETTVV (SEQ ID NO: 2) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACCGTCCGCCGAACGCACC GATCCTGAGCACCCTGCCGGAAACCACTGTTGTGTAAT AA (SEQ ID NO: 54) |
| SS1: D29C-R127C | MDIDPYKEFGATVELLS FLPSDFFPSVRCLLDTA AALYRDALESPEHCSPH HTALRQAILCWGDLSTL ATWVGTNMEDPASRDL VVSYVNTNVGLKFRQLL WFHISCLTFGRETVLEY LVSFGVWICTPPAYRPP NAPILSTLPETTVV (SEQ ID NO: 3) | ATGGATATCGACCCGTACAAAGAATTCGGCGCGACCG TTGAACTGCTGTCTTTCCTGCCGTCTGATTTCTTCCCG TCTGTTCGTTGCCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTTGTACTCCGCCGGCTTACCGTCCGCCGAACGCACC GATCCTGAGCACCCTGCCGGAAACCACTGTTGTGTAAT AA (SEQ ID NO: 55) |
| SS2: T109C-V120C | MDIDPYKEFGATVELLS FLPSDFFPSVRDLLDTA AALYRDALESPEHCSPH HTALRQAILCWGDLSTL ATWVGTNMEDPASRDL WSYVNTNVGLKFRQLL WFHISCLCFGRETVLEY LCSFGVWIRTPPAYRPP NAPILSTLPETTVV (SEQ ID NO: 4) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTTGCTTCGGTCGTGA AACCGTTCTGGAATACCTGTGCTCTTTTGGTGTTTGGA TTCGTACTCCGCCGGCTTACCGTCCGCCGAACGCACC GATCCTGAGCACCCTGCCGGAAACCACTGTTGTGTAAT AA (SEQ ID NO: 56) |
| SS3: Y132C-N136C | MDIDPYKEFGATVELLS FLPSDFFPSVRDLLDTA AALYRDALESPEHCSPH HTALRQAILCWGDLSTL ATWVGTNMEDPASRDL WSYVNTNVGLKFRQLL WFHISCLTFGRETVLEY LVSFGVWIRTPPACRPP CAPILSTLPETTVV (SEQ ID NO: 5) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTGCCGTCCGCCTGCGCACC GATCCTGAGCACCCTGCCGGAAACCACTGTTGTGTAAT AA (SEQ ID NO: 57) |
| SS4: Y132C-A137C | MDIDPYKEFGATVELLS FLPSDFFPSVRDLLDTA AALYRDALESPEHCSPH HTALRQAILCWGDLSTL ATWVGTNMEDPASRDL WSYVNTNVGLKFRQLL WFHISCLTFGRETVLEY LVSFGVWIRTPPACRPP | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG |

TABLE 1-continued

| Variants | Protein sequence | DNA encoding sequence |
| --- | --- | --- |
| | NCPILSTLPETTVV (SEQ ID NO: 6) | CTGTGGTTCCACATCTCTTGCCTGACCTTCGGTCGTGA AACCGTTCTGGAATACCTGGTTTCTTTTGGTGTTTGGA TTCGTACTCCGCCGGCTTGCCGTCCGCCGAACTGCCC GATCCTGAGCACCCTGCCGGAAACCACTGTTGTGTAAT AA (SEQ ID NO: 58) |
| SS5: R133C-N136C | MDIDPYKEFGATVELLS FLPSDFFPSVRDLLDTA AALYRDALESPEHCSPH HTALRQAILCWGDSTL ATWVGTNMEDPASRDL WSYVNTNVGLKFRQLL WFHISCLTFGRETVLEY LVSFGVWIRTPPAYCPP CAPILSTLPETTVV (SEQ ID NO: 7) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACTGCCCGCCGTGCGCACC GATCCTGAGCACCCTGCCGGAAACCACTGTTGTGTAAT AA (SEQ ID NO: 59) |
| SS6: R133C-A137C | MDIDPYKEFGATVELLS FLPSDFFPSVRDLLDTA AALYRDALESPEHCSPH HTALRQAILCWGDLSTL ATWVGTNMEDPASRDL WSYVNTNVGLKFRQLL WFHISCLTFGRETVLEY LVSFGVWIRTPPAYCPP NCPILSTLPETTVV (SEQ ID NO: 8) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACTGCCCGCCGAACTGCCC GATCCTGAGCACCCTGCCGGAAACCACTGTTGTGTAAT AA (SEQ ID NO: 60) |
| SS7: P134C-P135C | MDIDPYKEFGATVELLS FLPSDFFPSVRDLLDTA AALYRDALESPEHCSPH HTALRQAILCWGDSTL ATWVGTNMEDPASRDL WSYVNTNVGLKFRQLL WFHISCLTFGRETVLEY LVSFGVWIRTPPAYRCC NAPILSTLPETTVV (SEQ ID NO: 9) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACCGTTGCTGCAACGCACC GATCCTGAGCACCCTGCCGGAAACCACTGTTGTGTAAT AA (SEQ ID NO: 61) |
| SS8: P134C-N136C | MDIDPYKEFGATVELLS FLPSDFFPSVRDLLDTA AALYRDALESPEHCSPH HTALRQAILCWGDSTL ATWVGTNMEDPASRDL WSYVNTNVGLKFRQLL WFHISCLTFGRETVLEY LVSFGVWIRTPPAYRCP CAPILSTLPETTVV (SEQ ID NO: 10) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatcGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACCGTTGCCCGTGCGCACC GATCCTGAGCACCCTGCCGGAAACCACTGTTGTGTAAT AA (SEQ ID NO: 62) |
| SS9: P134C-A137C | MDIDPYKEFGATVELLS FLPSDFFPSVRDLLDTA AALYRDALESPEHCSPH HTALRQAILCWGDSTL ATWVGTNMEDPASRDL WSYVNTNVGLKFRQLL WFHISCLTFGRETVLEY LVSFGVWIRTPPAYRCP NCPILSTLPETTVV (SEQ ID NO: 11) | ATGGATATCGACCCGTACAAAGAATTCGGCGCGACCG TTGAACTGCTGTCTTTCCTGCCGTCTGATTTCTTCCCG TCTGTTCGTGACCTGCTGGACACCGCGGCAGCACTGT ACCGTGACGCGCTGGAATCTCCGGAACATTGTTCTCC GCATCACACTGCGCTGCGTCAGGCGATTCTGTGCTGG GGCGACCTGagcACCCTGGCGACTTGGGTTGGCACCA ACatgGAAGATCCGGCGTCTCGTGATCTGGTTGTTTCTT ACGTTAACACTAACGTTGGTCTGAAATTCCGTCAGCTG CTGTGGTTCCACATCTCTTGCCTGACCTTCGGTCGTGA AACCGTTCTGGAATACCTGGTTTCTTTTGGTGTTTGGA TTCGTACTCCGCCGGCTTACCGTTGCCCGAACTGCCC GATCCTGAGCACCCTGCCGGAAACCACTGTTGTGTAAT AA (SEQ ID NO: 63) |
| SS10: P135C-N136C | MDIDPYKEFGATVELLS FLPSDFFPSVRDLLDTA | ATGGATATCGACCCGTACAAAGAATTCGGCGCGACCG TTGAACTGCTGTCTTTCCTGCCGTCTGATTTCTTCCCG |

TABLE 1-continued

| Variants | Protein sequence | DNA encoding sequence |
|---|---|---|
| | AALYRDALESPEHCSPH<br>HTALRQAILCWGDLSTL<br>ATWVGTNMEDPASRDL<br>WSYVNTNVGLKFRQLL<br>WFHISCLTFGRETVLEY<br>LVSFGVWIRTPPAYRPC<br>CAPILSTLPETTVV<br>(SEQ ID NO: 12) | TCTGTTCGTGACCTGCTGGACACCGCGGCAGCACTGT<br>ACCGTGACGCGCTGGAATCTCCGGAACATTGTTCTCC<br>GCATCACACTGCGCTGCGTCAGGCGATTCTGTGCTGG<br>GGCGACCTGagcACCCTGGCGACTTGGGTTGGCACCA<br>ACatgGAAGATCCGGCGTCTCGTGATCTGGTTGTTTCTT<br>ACGTTAACACTAACGTTGGTCTGAAATTCCGTCAGCTG<br>CTGTGGTTCCACATCTCTTGCCTGACCTTCGGTCGTGA<br>AACCGTTCTGGAATACCTGGTTTCTTTTGGTGTTTGGA<br>TTCGTACTCCGCCGGCTTACCGTCCGTGCTGCGCACC<br>GATCCTGAGCACCCTGCCGGAAACCACTGTTGTGTAAT<br>AA (SEQ ID NO: 64) |

The sequences of 17 different variants with different AHA sites or different negative surface charge mutations intended to change surface charge and improve conjugation efficiency without affecting expression and assembly yields. All sequences include the SS1 mutations (red codons) and the M66S mutation (blue codon). AHA signifies azidohomoalanine, the non-natural amino acid tested.

TABLE 2

| Variants | Protein sequence | DNA encoding sequence |
|---|---|---|
| 00. Original<br>(L76AHA) | MDIDPYKEFGATVE<br>LLSFLPSDFFPSVR<br>DLLDTAAALYRDAL<br>ESPEHCSPHHTAL<br>RQAILCWGDLSTLA<br>TWVGTN**(AHA)**EDP<br>ASRDLVVSYVNTN<br>VGLKFRQLLWFHIS<br>CLTFGRETVLEYLV<br>SFGVWIRTPPAYR<br>PPNAPILSTLPETT<br>VV<br>(SEQ ID NO: 13) | ATGGATATCGACCCGTACAAAGAATTCGGCGCGACC<br>GTTGAACTGCTGTCTTTCCTGCCGTCTGATTTCTTTCCC<br>GTCTGTTCGTGACCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACatgGAAGATCCGGCGTCTCGTGATCTGGTTGT<br>TTCTTACGTTAACACTAACGTTGGTCTGAAATTCCGTC<br>AGCTGCTGTGGTTCCACATCTCTTGCCTGACCTTCGG<br>TCGTGAAACCGTTCTGGAATACCTGGTTTCTTTTGGT<br>GTTTGGATTCGTACTCCGCCGGCTTACCGTCCGCCG<br>AACGCACCGATCCTGAGCACCCTGCCGGAAACCACT<br>GTTGTGTAATAA (SEQ ID NO: 65) |
| 0. SS1 (L76AHA) | MDIDPYKEFGATVE<br>LLSFLPSDFFPSVR<br>CLLDTAAALYRDAL<br>ESPEHCSPHHTAL<br>RQAILCWGDLSTLA<br>TWVGTN**(AHA)**EDP<br>ASRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 14) | ATGGATATCGACCCGTACAAAGAATTCGGCGCGACC<br>GTTGAACTGCTGTCTTTCCTGCCGTCTGATTTCTTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACatgGAAGATCCGGCGTCTCGTGATCTGGTTGT<br>TTCTTACGTTAACACTAACGTTGGTCTGAAATTCCGTC<br>AGCTGCTGTGGTTCCACATCTCTTGCCTGACCTTCGG<br>TCGTGAAACCGTTCTGGAATACCTGGTTTCTTTTGGT<br>GTTTGGATTTGTACTCCGCCGGCTTACCGTCCGCCGA<br>ACGCACCGATCCTGAGCACCCTGCCGGAAACCACTG<br>TTGTGTAATAA (SEQ ID NO: 66) |
| 1. T74AHA | MDIDPYKEFGATVE<br>LLSFLPSDFFPSVR<br>CLLDTAAALYRDAL<br>ESPEHCSPHHTAL<br>RQAILCWGDLSTLA<br>TWVG**(AHA)**NLEDP<br>ASRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 15) | ATGGATATCGACCCGTACAAAGAATTCGGCGCGACC<br>GTTGAACTGCTGTCTTTCCTGCCGTCTGATTTCTTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>atgAACCTGGAAGATCCGGCGTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATGAGCACCCTGCCGGAAACCACTGT<br>TGTGTAATAA (SEQ ID NO: 67) |
| 2. D78AHA | MDIDPYKEFGATVE<br>LLSFLPSDFFPSVR<br>CLLDTAAALYRDAL<br>ESPEHCSPHHTAL<br>RQAILCWGDLSTLA<br>TVVVGTNLE**(AHA)**P<br>ASRDLVVSYVNTN<br>VGLKFRQLLWFHIS<br>CLTFGRETVLEYLV<br>SFGVWICTPPAYR | ATGGATATCGACCCGTACAAAGAATTCGGCGCGACC<br>GTTGAACTGCTGTCTTTCCTGCCGTCTGATTTCTTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACCTGGAAatgCCGGCGTCTCGTGATCTGGTTGT<br>TTCTTACGTTAACACTAACGTTGGTCTGAAATTCCGTC<br>AGCTGCTGTGGTTCCACATCTCTTGCCTGACCTTCGG<br>TCGTGAAACCGTTCTGGAATACCTGGTTTCTTTTGGT |

TABLE 2-continued

| Variants | Protein sequence | DNA encoding sequence |
|---|---|---|
| | PPNAPILSTLPETT VV (SEQ ID NO: 16) | GTTTGGATTTGTACTCCGCCGGCTTACCGTCCGCCGA ACGCACCGATCCTGAGCACCCTGCCGGAAACCACTG TTGTGTAATAA (SEQ ID NO: 68) |
| 3. D78AHA + E77S | MDIDPYKEFGATVE LLSFLPSDFFPSVR CLLDTAAALYRDAL ESPEHCSPHHTAL RQAILCWGDLSTLA TWVGTNLS (AHA) P ASRDLVVSYVNTN VGLKFRQLLWFHIS CLTFGRETVLEYLV SFGVWICTPPAYR PPNAPILSTLPETT VV (SEQ ID NO: 17) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGAd-GCGCTGGAATCTCCGGAACATTGTTCT CCGCATCACACTGCGCTGCGTCAGGCGATTCTGTGC TGGGGCGACCTGagcACCCTGGCGACTTGGGTTGGC ACCAACCTGagcatgCCGGCGTCTCGTGATCTGGTTGT TCTTACGTTAACACTAACGTTGGTCTGAAATTCCGTC AGCTGCTGTGGTTCCACATCTCTTGCCTGACCTTCGG TCGTGAAACCGTTCTGGAATACCTGGTTTCTTTTGGT GTTTGGATTTGTACTCCGCCGGCTTACCGTCCGCCGA ACGCACCGATCCTGAGCACCCTGCCGGAAACCACTG TTGTGTAATAA (SEQ ID NO: 69) |
| 4. D78AHA + L76S | MDIDPYKEFGATVE LLSFLPSDFFPSVR CLLDTAAALYRDAL ESPEHCSPHHTAL RQAILCWGDLSTLA TWVGTNSE (AHA) P ASRDLVVSYVNTN VGLKFRQLLWFHIS CLTFGRETVLEYLV SFGVWICTPPAYR PPNAPILSTLPETT VV (SEQ ID NO: 18) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGGC ACCAACagcGAAatgCCGGCGTCTCGTGATCTGGTTGT TCTTACGTTAACACTAACGTTGGTCTGAAATTCCGTC AGCTGCTGTGGTTCCACATCTCTTGCCTGACCTTCGG TCGTGAAACCGTTCTGGAATACCTGGTTTCTTTTGGT GTTTGGATTTGTACTCCGCCGGCTTACCGTCCGCCGA ACGCACCGATCCTGAGCACCCTGCCGGAAACCACTG TTGTGTAATAA (SEQ ID NO: 70) |
| 5. D78AHA + L76S + E77A | MDIDPYKEFGATVE LLSFLPSDFFPSVR CLLDTAAALYRDAL ESPEHCSPHHTAL RQAILCWGDLSTLA TWVGTNA (AHA) P ASRDLVVSYVNTN VGLKFRQLLWFHIS CLTFGRETVLEYLV SFGVWICTPPAYR PPNAPILSTLPETT VV (SEQ ID NO: 19) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGGC ACCAACagcgcgatgCCGGCGTCTCGTGATCTGGTTGTT TCTTACGTTAACACTAACGTTGGTCTGAAATTCCGTCA GCTGCTGTGGTTCCACATCTCTTGCCTGACCTTCGGT CGTGAAACCGTTCTGGAATACCTGGTTTCTTTTGGTG TTTGGATTTGTACTCCGCCGGCTTACCGTCCGCCGAA CGCACCGATCCTGAGCACCCTGCCGGAAACCACTGT TGTGTAATAA (SEQ ID NO: 71) |
| 6. P79AHA | MDIDPYKEFGATVE LLSFLPSDFFPSVR CLLDTAAALYRDAL ESPEHCSPHHTAL RQAILCWGDLSTLA TVVVGTNLED**(AHA)** ASRDLVVSYVNTN VGLKFRQLLWFHIS CLTFGRETVLEYLV SFGVWICTPPAYR PPNAPILSTLPETT VV (SEQ ID NO: 20) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGGC ACCAACCTGGAAGATatgGCGTCTCGTGATCTGGTTGT TCTTACGTTAACACTAACGTTGGTCTGAAATTCCGTC AGCTGCTGTGGTTCCACATCTCTTGCCTGACCTTCGG TCGTGAAACCGTTCTGGAATACCTGGTTTCTTTTGGT GTTTGGATTTGTACTCCGCCGGCTTACCGTCCGCCGA ACGCACCGATCCTGAGCACCCTGCCGGAAACCACTG TTGTGTAATAA (SEQ ID NO: 72) |
| 7. P79AHA + E77K | MDIDPYKEFGATVE LLSFLPSDFFPSVR CLLDTAAALYRDAL ESPEHCSPHHTAL RQAILCWGDLSTLA TWVGTNLKD (AHA) ASRDLVVSYVNTN VGLKFRQLLWFHIS CLTFGRETVLEYLV SFGVWICTPPAYR PPNAPILSTLPETT VV (SEQ ID NO: 21) | ATGGATATCGACCCGTACAAAGAATTCGGCGCGACC GTTGAACTGCTGTCTTTCCTGCCGTCTGATTTCTTCCC GTCTGTTCGTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGGC ACCAACCTGaaaGATatgGCGTCTCGTGATCTGGTTGTT TCTTACGTTAACACTAACGTTGGTCTGAAATTCCGTCA GCTGCTGTGGTTCCACATCTCTTGCCTGACCTTCGGT CGTGAAACCGTTCTGGAATACCTGGTTTCTTTTGGTG TTTGGATTTGTACTCCGCCGGCTTACCGTCCGCCGAA CGCACCGATCCTGAGCACCCTGCCGGAAACCACTGT TGTGTAATAA (SEQ ID NO: 73) |

TABLE 2-continued

| Variants | Protein sequence | DNA encoding sequence |
|---|---|---|
| 8. P7AHA + D78K | MDIDPYKEFGATVE LLSFLPSDFFPSVR CLLDTAAALYRDAL ESPEHCSPHHTAL RQAILCWGDLSTLA TWVGTNLEK(AHA) ASRDLVVSYVNTN VGLKFRQLLWFHIS CLTFGRETVLEYLV SFGVWICTPPAYR PPNAPILSTLPETT VV (SEQ ID NO: 22) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGCC ACCAACCTGGAAaaaatgGCGTCTCGTGATCTGGTTGT TCTTACGTTAACACTAACGTTGGTCTGAAATTCCGTC AGCTGCTGTGGTTCCACATCTCTTGCCTGACCTTCGG TCGTGAAACCGTTCTGGAATACCTGGTTTCTTTTGGT GTTTGGATTTGTACTCCGCCGGCTTACCGTCCGCCGA ACGCACCGATCCTGAGCACCCTGCCGGAAACCACTG TTGTGTAATAA (SEQ ID NO: 74) |
| 9. P79AHA + E77S | MDIDPYKEFGATVE LLSFLPSDFFPSVR CLLDTAAALYRDAL ESPEHCSPHHTAL RQAILCWGDLSTLA TWVGTNLSD(AHA) ASRDLVVSYVNTN VGLKFRQLLWFHIS CLTFGRETVLEYLV SFGVWICTPPAYR PPNAPILSTLPETT VV (SEQ ID NO: 23) | ATGGATATCGACCCGTACAAAGAATTCGGCGCGACC GTTGAACTGCTGTCTTTCCTGCCGTCTGATTTCTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGCC ACCAACCTGagcGATatgGCGTCTCGTGATCTGGTTGTT TCTTACGTTAACACTAACGTTGGTCTGAAATTCCGTCA GCTGCTGTGGTTCCACATCTCTTGCCTGACCTTCGGT CGTGAAACCGTTCTGGAATACCTGGTTTCTTTTGGTG TTTGGATTTGTACTCCGCCGGCTTACCGTCCGCCGAA CGCACCGATCCTGAGCACCCTGCCGGAAACCACTGT TGTGTAATAA (SEQ ID NO: 75) |
| 10. P79AHA + D78S | MDIDPYKEFGATVE LLSFLPSDFFPSVR CLLDTAAALYRDAL ESPEHCSPHHTAL RQAILCWGDLSTLA TVVVGTNLES(AHA) ASRDLVVSYVNTN VGLKFRQLLWFHIS CLTFGRETVLEYLV SFGVWICTPPAYR PPNAPILSTLPETT VV (SEQ ID NO: 24) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGCC ACCAACCTGGAAagcatgGCGTCTCGTGATCTGGTTGTT TCTTACGTTAACACTAACGTTGGTCTGAAATTCCGTCA GCTGCTGTGGTTCCACATCTCTTGCCTGACCTTCGGT CGTGAAACCGTTCTGGAATACCTGGTTTCTTTTGGTG TTTGGATTTGTACTCCGCCGGCTTACCGTCCGCCGAA CGCACCGATCCTGAGCACCCTGCCGGAAACCACTGT TGTGTAATAA (SEQ ID NO: 76) |
| 11. P79AHA + E77S + D78S | MDIDPYKEFGATVE LLSFLPSDFFPSVR CLLDTAAALYRDAL ESPEHCSPHHTAL RQAILCWGDLSTLA TWVGTNLSS(AHA) ASRDLVVSYVNTN VGLKFRQLLWFHIS CLTFGRETVLEYLV SFGVWICTPPAYR PPNAPILSTLPETT VV (SEQ ID NO: 25) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGCC ACCAACCTGagcagcatgGCGTCTCGTGATCTGGTTGTT TCTTACGTTAACACTAACGTTGGTCTGAAATTCCGTCA GCTGCTGTGGTTCCACATCTCTTGCCTGACCTTCGGT CGTGAAACCGTTCTGGAATACCTGGTTTCTTTTGGTG TTTGGATTTGTACTCCGCCGGCTTACCGTCCGCCGAA CGCACCGATCCTGAGCACCCTGCCGGAAACCACTGT TGTGTAATAA (SEQ ID NO: 77) |
| 12. A80AHA | MDIDPYKEFGATVE LLSFLPSDFFPSVR CLLDTAAALYRDAL ESPEHCSPHHTAL RQAILCWGDLSTLA TWVGTNLEDPSS(AHA) SRDLVVSYVNTN VGLKFRQLLWFHIS CLTFGRETVLEYLV SFGVWICTPPAYR PPNAPILSTLPETT VV (SEQ ID NO: 26) | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC TGGGGCGACCTGagcACCCTGGCGACTTGGGTTGCC ACCAACCTGGAAGATCCatgTCGTGATCTGGTTGT TCTTACGTTAACACTAACGTTGGTCTGAAATTCCGTC AGCTGCTGTGGTTCCACATCTCTTGCCTGACCTTCGG TCGTGAAACCGTTCTGGAATACCTGGTTTCTTTTGGT GTTTGGATTTGTACTCCGCCGGCTTACCGTCCGCCGA ACGCACCGATCCTGAGCACCCTGCCGGAAACCACTG TTGTGTAATAA (SEQ ID NO: 78) |
| 13. A80AHA + E77K | MDIDPYKEFGATVE LLSFLPSDFFPSVR CLLDTAAALYRDAL ESPEHCSPHHTAL RQAILCWGDLSTLA | ATGGATATCGACCCGTACAAAGAATTCGGCGCGACC GTTGAACTGCTGTCTTTCCTGCCGTCTGATTTCTTCCC GTCTGTTCGTTGCCTGCTGGACACCGCGGCAGCACT GTACCGTGACGCGCTGGAATCTCCGGAACATTGTTCT CCGCATCACACTGCGCTGCGTCAGGCGATTCTGTGC |

TABLE 2-continued

| Variants | Protein sequence | DNA encoding sequence |
|---|---|---|
| | TVVVGTNLKDP_(AH_<br>_A)_SRDLVVSYVNYN<br>VGLKFRQLLWFHIS<br>CLTFGRETVLEYLV<br>SFGVWICTPPAYR<br>PPNAPILSTLPETT<br>VV<br>(SEQ ID NO: 27) | TGGGGCGACCTGagcACCCTGGCGACTTGGGTTGGC<br>ACCAACCTGaaaGATCCGatgTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATCCTGAGCACCCTGCCGGAAACCACTGT<br>TGTGTAATAA (SEQ ID NO: 79) |
| 14. A80AHA +<br>D78K | MDIDPYKEFGATVE<br>LLSFLPSDFFPSVR<br>CLLDTAAALYRDAL<br>ESPEHCSPHHTAL<br>RQAILCWGDLSTLA<br>TVVVGTNLEKP_(AH_<br>_A)_SRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 28) | ATGGATATCGACCCGTACAAAGAATTCGGCGCGACC<br>GTTGAACTGCTGTCTTTCCTGCCGTCTGATTTCTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACCTGGAAaaaCCGatgTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATCCTGAGCACCCTGCCGGAAACCACTGT<br>TGTGTAATAA (SEQ ID NO: 80) |
| 15. A80AHA +<br>E77S | MDIDPYKEFGATVE<br>LLSFLPSDFFPSVR<br>CLLDTAAALYRDAL<br>ESPEHCSPHHTAL<br>RQAILCWGDLSTLA<br>TWVGTNLSDP_(AH_<br>_A)_SRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 29) | ATGGATATCGACCCGTACAAAGAATTCGGCGCGACC<br>GTTGAACTGCTGTCTTTCCTGCCGTCTGATTTCTTCCC<br>GTCTGTTCGTTGCCTGCTGGACACCGCGGCAGCACT<br>GTACCGTGAdkaCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACCTGaaaGATCCGatgTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATCCTGAGCACCCTGCCGGAAACCACTGT<br>TGTGTAATAA (SEQ ID NO: 81) |
| 16. A80AHA +<br>D78S | MDIDPYKEFGATVE<br>LLSFLPSDFFPSVR<br>CLLDTAAALYRDAL<br>ESPEHCSPHHTAL<br>RQAILCWGDLSTLA<br>TWVGTNLESP_(AH_<br>_A)_SRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 30) | ATGGATATCGACCCGTACAAAGAATTCGGCGCGACC<br>GTTGAACTGCTGTCTTTCCTGCCGTCTGATTTCTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACCTGGAAagcCCGatgTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATCCTGAGCACCCTGCCGGAAACCACTGT<br>TGTGTAATAA (SEQ ID NO: 82) |
| 17.<br>A80AHA + E77S +<br>D78S | MDIDPYKEFGATVE<br>LLSFLPSDFFPSVR<br>CLLDTAAALYRDAL<br>ESPEHCSPHHTAL<br>RQAILCWGDLSTLA<br>TWVGTNLSSP_(AH_<br>_A)_SRDLVVSYVNTN<br>VGLKFRQLLWFHIS<br>CLTFGRETVLEYLV<br>SFGVWICTPPAYR<br>PPNAPILSTLPETT<br>VV<br>(SEQ ID NO: 31) | ATGGATATCGACCCGTACAAAGAATTCGGCGCGACC<br>GTTGAACTGCTGTCTTTCCTGCCGTCTGATTTCTTCCC<br>GTCTGTTCGTTGCCTGCTGGACACCGCGGCAGCACT<br>GTACCGTGACGCGCTGGAATCTCCGGAACATTGTTCT<br>CCGCATCACACTGCGCTGCGTCAGGCGATTCTGTGC<br>TGGGGCGACCTGagcACCCTGGCGACTTGGGTTGGC<br>ACCAACCTGagcagcCCGatgTCTCGTGATCTGGTTGTT<br>TCTTACGTTAACACTAACGTTGGTCTGAAATTCCGTCA<br>GCTGCTGTGGTTCCACATCTCTTGCCTGACCTTCGGT<br>CGTGAAACCGTTCTGGAATACCTGGTTTCTTTTGGTG<br>TTTGGATTTGTACTCCGCCGGCTTACCGTCCGCCGAA<br>CGCACCGATCCTGAGCACCCTGCCGGAAACCACTGT<br>TGTGTAATAA (SEQ ID NO: 83) |

Cell-free protein synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 45 μg/mL plasmid, approximately 100-300 μg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of *E. coli* KC6 S30 extract (Goerke and Swartz 2008). For global replacement of methionines in HBc proteins, methionine was left out of cell-free reaction mixtures, and substituted by 1 mM azidohomoalanine (AHA) (Medchem Source LLP, Federal Way, Wash.), a non-natural amino acid that displays an azide moiety. All reagents were obtained from Sigma-Aldrich (St. Louis, Miss.) unless otherwise noted.

CFPS reactions to produce the HBc protein were conducted at 30° C. for 6 h. Small-scale CFPS reactions were carried out in 20 µL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 µM L-[U-$^{14}$C]-Leucine (PerkinElmer, Waltham, MA) was added to small-scale reactions and to 20 µL aliquots of preparative-scale reactions for measuring protein yields using a previously described trichloroacetic acid protein precipitation protocol and a Beckman LS3801 liquid scintillation counter (Beckman Coulter, Fullerton, Calif.).

The production of GM-CSF, IM9-ScFv and CpG DNA with an alkyne moiety were described by Patel et al. The production of flagellin with an alkyne moiety was described by Lu et al.

Size-exclusion chromatography (SEC). To remove unincorporated L-[U-14C] leucine, the cell-free product was immediately dialyzed in 6-8000 MWCO Specra/Pro Molecularporous Membrane Tubing (Spectrum Labs, Rancho Dominguez, Calfi.) against Dialysis Buffer (10 mM Tris-HCl, pH 7.4, 0.5 M NaCl) with 1 mM DTT with 2 buffer exchanges. The dialyzed cell-free reaction product was loaded on an SEC (size-exclusion chromatography) column packed with Sepharose 6 FastFlow resin (GE Healthcare). The running buffer is as the dialysis buffer with 5 mM DTT. The protein concentrations of eluate fractions were determined based on radioactivity.

Sucrose gradient sedimentation. The isolated VLPs from SEC were firstly dialyzed against the Dialysis Buffer to remove DTT, and were then oxidized to form disulfide bonds by adding 10 mM $H_2O_2$ or 10 mM diamide and incubating at room temperature for 1 h. The oxidants were removed by dialysis against the Dialysis Buffer with 2 buffer exchanges. The oxidized VLPs were assessed by velocity sedimentation. Ten to forty percentage weight per volume continuous sucrose density gradients were prepared in Dialysis Buffer in Polyallose 16×102 mm Centrifuge Tubes (Beckman) with the Gradient Master Ver3.05L Gradient Maker (Biocomp Instruments, Inc., Fredericton, Canada). The VLP product (200 µL) was layered on top of the sucrose and centrifuged at 31,000 rpm in a Beckman Coulter SW-32.1 swinging bucket rotor (Fullerton, Calif.) in a Beckman L8-M ultracentrifuge at 4° C. for 7 h with profile 7 slow acceleration and deceleration. One-half milliliter fractions were collected and the concentration in each fraction was determined by radioactivity measurement.

SDS-PAGE and autoradiogram. Protein size was analyzed by SDS-PAGE and autoradiography. NuPAGE Novex precast gels and reagents were purchased from Invitrogen (Carlsbad, Calif.). For reducing SDS-PAGE, samples were denatured for 10 min at 95° C. in loading buffer (1× LDS running buffer and 50 mM dithiothreitol). For non-reducing SDS-PAGE, samples were only mixed with LDS running buffer, without addition of dithiothreitol and heat treatment. The samples were loaded onto a 10% (w/v) Bis-Tris precast gel with SeeBlue Plus2 molecular weight protein standard, and electrophoresed in MES/SDS running buffer. Simply-Blue SafeStain was used to stain and fix the gels according to the manufacturer's recommendations. The gels were dried using a gel dryer model 583 (Bio-Rad, Richmond, Calif.), before exposure to a storage phosphor screen (Molecular Dynamics), which was subsequently scanned using a Typhoon Scanner (GE Healthcare).

Azide-Alkyne conjugation and purification. The [3+2] cycloaddition click reactions were conducted in an anaerobic glovebox (Coy Laboratories, Grass Lake, Mich.) to preserve the reduced state of the tetrakis(acetonitrile)copper (I)hexafluorophosphate catalyst ([(CH3CN)4Cu]PF6 or simply Cu (I) catalyst) (Sigma Aldrich, St. Louis, Miss.). Cu (I) catalyst was added to reactions at 1 mM in addition to 0.5 mM of the enhancer ligand, tris(triazolylmethyl) amine (TTMA), to improve the rate of the click reactions. HBc VLPs and functional molecules (flagellin, GM-CSF, IM9-ScFv or CpG DNA) were mixed with the Cu (I) catalyst and TTMA enhancer with 0.01% Tween 20. Before addition of the Cu (I) catalyst, click reaction components were deoxygenated in 1.5 mL microcentrifuge tubes for 1 h in the anaerobic glovebox. The click reactions for attaching functional molecules to HBc VLPs were conducted overnight.

Results and Discussions

Stabilization of HBc VLP by introducing covalent disulfide bonds. In this study, HBc capsid protein truncated at V149 was used. The truncated HBc protein self-assembles into VLPs, composed of 240 subunits arranged with T=4 icosahedral symmetry. The T=4 icosahedral capsid has 12 regular pentagonal faces and 30 regular hexagonal faces, as shown in FIG. 1. Each pentamer is surrounded by 5 hexamers. A five-fold unit of HBc dimers and a six-fold unit of HBc dimers comprise one pentamer and one hexamer, respectively, as shown in FIG. 1. The 5-fold unit and the 6-fold unit share one dimer, and are cross-linked to form the VLP.

There are four types of bonding interactions between "side chains" including: hydrogen bonding, salt bridges, disulfide bonds, and non-polar hydrophobic interactions. The covalent disulfide bonds are the strongest. After analyzing the results of many conjugation reactions, we discovered that the HBc VLP scaffold was not stable during the click conjugation reaction. To address this, we assessed the 3D tertiary structure of the capsid to identify sites where neighboring monomers were close enough to be linked by disulfide bonds. If we could introduce disulfide bridges to cross-link the 5-fold and 6-fold units, the VLP could be stabilized.

To form stable VLPs, possible disulfide (S—S) bond positions at both 5-fold unit and 6-fold unit were sought. We devised two strategies. The first is looking for two amino acids with the shortest distances between the side chains of dimers, as shown in FIG. 2(c). In the second, we examined possible disulfide bonds between the C-terminal regions of monomers, as shown in FIG. 2(c). The distances suggested by the icosahedral capsid structure are shown in parentheses. Because one original disulfide bond already exists in the dimer, the introduction of new disulfide bonds can greatly stabilize the VLP. A total of 10 positions was selected, including SS1 (D29-R127), SS2 (T109-V120), SS3 (Y132-N136), SS4 (Y132-A137), SS5 (R133-N136), SS6 (R133-A137), SS7 (P134-P135), SS8 (P134-N136), SS9 (P134-A137), and SS10 (P135-N136). The codons for these amino acids were then changed to codons for cysteine.

To form correct S—S bonds, the HBc proteins were firstly synthesized in the CFPS system in a reducing environment. The HBc protein can self-assemble into VLPs in the CFPS system. After dialysis, the assembled VLPs were then purified using size-exclusion chromatography (SEC) in a reducing environment. The maintenance of the reducing environment is to prevent the formation of incorrect S—S bonds before assembly of the VLPs. The purified VLPs were then oxidized to form S—S bonds by adding oxidants (hydrogen peroxide or diamide). The particle sizes were finally assessed using sucrose gradient centrifugation. The whole procedure is shown in FIG. 2(c).

The CFPS results showed that the mutants all have similar total yields as the original HBc protein (FIG. 5(a)). All 10 candidates expressed with good soluble yields ≥300 µg/ml). The non-reducing SDS-PAGE autoradiograph (FIG. 3(c)) showed that only a small amount of dimers formed in the CFPS system for the mutants. After dialysis, the CFPS products were then purified using SEC (FIG. 2d). The mutants SS3, SS4, SS5 and SS6 did not assemble into VLPs. The SEC fractions 9-11 for the other mutants were pooled and oxidized by the addition of 10 mM $H_2O_2$ or 10 mM diamide. After the oxidization treatment, the fully cross-linked VLPs could not be disassembled with SDS and failed to enter the SDS-PAGE gel (FIG. 3e). We could see some monomers and dimers for mutants SS2, SS7, and SS9, which demonstrated that some S—S bonds were not formed. Only SS1 particles all stayed in the well of SDS-PAGE gel after oxidation with diamide, which demonstrated that all S—S bonds were formed in SS1 VLPs. Based on these results, mutant SS1 appeared to be the best although mutants SS8 and SS10 were also highly cross-linked The oxidized particles were then assessed using sucrose gradient centrifugation to indicate proper assembly (FIG. 3f). The results showed that the sizes of SS1, SS7, SS8, SS9 and SS10 VLPs were all correct.

To further verify the functions of the oxidized VLPs, the click chemistry reactions were then tested. Flagellin protein and GM-CSF protein were used as example adducts. CFPS provides a facile means for introducing nnAAs with an alkyne moiety into flagellins and GM-CSFs, and nnAAs with an azide moiety into VLPs (Bundy et al. 2008; Goerke and Swartz 2008; Patel and Swartz 2011). This would allow the direct coupling of flagellin or GM-CSF to VLPs using Cu(I)-catalyzed [3+2] cycloaddition click chemistry reaction. The reaction results (FIG. 3h) showed that flagellin and GM-CSF could be successfully conjugated to SS1, SS7, SS8, SS9 and SS10 VLPs.

Based on the results above, mutant SS1 VLP was the most effectively stabilized VLP, and SS8 and SS10 were nearly as good.

Example 2

At physiological pH, the surface of the HBc VLP is negatively charged. The surface of the HBc VLP is dominated by 120 dimer spikes that stick out from the surface. These spikes are obvious attachment sites with high steric availability, but they are terminated with four negatively charged amino acids (E77×2, D78×2). The negative charges on the VLP surface are from these four negatively charged amino acids on the spike tip. Because like charges repel, molecules with negative charges cannot get close to HBc VLP, and therefore the click chemistry conjugation cannot proceed effectively. The removal of the surface negative charges greatly decreased the protein's solubility, and HBc proteins could not self-assemble into VLPs very well. The following example addresses this problem.

Transplant of new spike. Removal of HBc VLP surface negative charges decreased its solubility and self-assembly ability. This led us to seek alternative methods for remodeling the HBc dimer spike in naturally occurring viral mutants. A few natural mutants with only one negatively charged amino acid on the protein monomer tip were found. One natural mutant (UniProt accession number: Q8B6N7) was selected and compared with the native HBc protein (UniProt accession number: P03147). In genotype Q8B6N7, one net negative charge is still at the 78 site, but another one transfers to the 70 site from the original 77 site in genotype P03147.

To determine the effects of these sequence changes in Q8B6N7 on the characteristics of the VLP, the spike (the spike tip (ST) or the whole hydrophobic pocket (HP)) in Q8B6N7 was transplanted into native HBc proteins (FIG. 4*b*). Two new mutants HBc(ST) and HBc(HP) were created and compared with mutant HBc(D78M). HBc(D78M) is the native HBc protein with the removal of one negative charge (D78) on the tip. HBc(D78M), HBc(ST), and HBc(HP) were stabilized by introducing new disulfide bridges (D29C-R127C). After one negative charge on the tip of the native protein was removed, the solubility of the mutant HBc (D78M) was only around 50% (FIG. 5). These two new mutants HBc(ST) and HBc(HP) improved solubility greatly (FIG. 5). HBc(HP) was more soluble than HBc(ST). Native HBc proteins can self-assemble into VLPs in buffer with 0.5 M NaCl, but HBc(ST) and HBc(HP) could not self-assemble into VLPs after dialysis against a buffer with 0.5 M NaCl (FIG. 4*d*), which further suggested that the negative charges on the virus capsid surface are important for the particle assembly. After dialysis against buffer with a higher concentration of NaCl (1.5 M), the modified HBc proteins could assemble into VLPs as indicated by SEC analysis. Because HBc(HP) (SEQ ID NO:35) had better solubility than HBc (ST), HBc(HP) was chosen in the subsequent development.

Selection of non-natural amino acid (nnAA) sites on the spike tip. The surface of the HBc VLP is dominated by 120 dimer spikes that stick out from the surface. The tip of these spikes are obvious attachment sites with high steric availability. To identify the best conjugation site, six different nnAA sites (N75AHA, L76AHA, Q77AHA, D78AHA, Q79AHA, and A80AHA) on the spike tip were tried, as shown in FIG. 4*e*. These mutants were all stabilized by introducing new disulfide bridges (D29C-R127C). AHA signifies the nnAA, azidohomoalanine, with an azide moiety. Incorporating the nnAA site at D78 removes the negative charges at the spike tip.

CFPS results showed that all these mutants were very soluble except mutant D78AHA (FIG. 4*f*). However, after dialysis against buffer with 1.5 M NaCl, the soluble yield of mutant D78AHA could reach 70%. SEC results showed that all these mutants could self-assemble into VLPs (FIG. 6*d*).

The ability to conjugate ligands onto these mutated VLPs were then tested with click chemistry reactions. We used four molecules with the alkyne functional group, including flagellin protein, GMCSF protein, IM9-ScFv protein, and CpG DNA. IM9-scFv and CpG DNA are characterized by negative charge density near the alkyne functional group. As previously mentioned, the surface of native HBc VLPs is negatively charged, so molecules with negative charges cannot get close to native HBc VLP surface, and therefore the click chemistry conjugation cannot proceed effectively. The mutant HBc(HP) D78AHA had no negative charge on the spike tip. The conjugation reaction results (FIG. 7*e/f*) showed that the removal of surface negative charges on the HBc VLP did greatly improve the conjugation efficiency of IM9-scFv and CpG DNA, especially for CpG DNA. Based on the results above, mutant HBc(HP) D78AHA was the best VLP in terms of conjugation efficiency.

Stabilization by the introduction of disulfide bridges. HBc protein truncated at amino acid 149 has been shown to form predominantly (>95%) the T=4 VLP. Two monomers (16.7 kDa) associate to give a compact dimer (33.5 kDa). At the dimer interface, there is a disulfide bridge between the Cys-61 residues of the two monomers further stabilizing the dimer. Dimers (120 copies) then self-assemble into the T=4 VLP by electrostatic interactions, hydrogen bonds and weak hydrophobic interactions (FIG. 1a). The T=4 icosahedral capsid has 12 regular pentagonal faces and 30 regular hexagonal faces (FIG. 1b). Each pentamer is surrounded by 5 hexamers. The five-fold unit of HBc dimer and the six-fold unit of HBc dimer comprise of one pentamer and one hexamer, respectively. The 5-fold unit and the 6-fold unit share one dimer, and are cross-linked to form the VLP. At the interface of the 5-fold unit and the 6-fold unit, there is an intradimer disulfide bond.

In order to strengthen the HBc(HP) VLP scaffold after conjugation with proteins and other molecules, covalent disulfide bridges that would stabilize both the 5-fold and 6-fold units were introduced (FIG. 2b).

To form stable VLPs, consistent possible disulfide (S—S) bond positions in both 5-fold unit and 6-fold unit were searched. In total, 10 positions were selected, including SS1 (D29C-R127C), SS2 (T109C-V120C), SS3 (Y132C-N136C), SS4 (Y132C-A137C), SS5 (R133C-N136C), SS6 (R133C-A137C), SS7 (P134C-P135C), SS8 (P134C-N136C), SS9 (P134C-A137C), SS10 (P135C-N136C). The codons for chosen amino acids were changed to codons for cysteine. After CFPS and dialysis, the VLPs were purified by SEC, as shown in FIG. 6f. HBc(HP) mutants SS3, SS4, SS5, and SS6 did not assemble effectively. The VLP fractions for the other mutants were pooled and oxidized by the addition of 20 mM diamide. After the oxidization treatment, the fully cross-linked VLPs could not be disassembled with SDS and failed to enter the SDS-PAGE gel (FIG. 6g). Only SS1 particles stayed completely in the sample addition well of the SDS-PAGE gel, which demonstrated that all S—S bonds were formed in SS1 VLPs. However, SS8 and SS10 were nearly as stable. To make the disulfide network in the VLP stronger, SS1 and SS8 were introduced in the VLP at the same time. SEC analysis showed that mutation SS1+SS8 did not hinder the VLP assembly. SDS-PAGE analysis also indicated that all S—S bonds were formed in the SS1+SS8 VLPs.

Based on the results above, mutant HBc(HP) D78AHA SS1+SS8 (SEQ ID NO:52) was the most stabilized VLP and also provides high conjugation efficiency.

Materials and Methods

Plasmid construction. The sequence encoding the human Hepatitis B core (HBc) capsid monomer of subtype adyw (Pasek et al., 1979) with the C-terminus truncated at amino acid 149 was optimized for *E. coli* tRNA concentrations and was synthesized from oligonucleotides designed with DNAworks v3.0. The vector pET24a-HBc149 was generated by ligation (T4 DNA ligase, New England Biolabs, Ipswich, Mass.) of the optimized HBc protein gene into the pET-24a (+) vector (Novagen, San Diego, Calif.) at the Nde I and Xho I restriction sites. To incorporate methionine analogues, two mutations (M66S and L76M) were introduced. pET24a-HBc149-M66S-L76M was transformed into DH5a cells and the plasmid was purified with Qiagen Plasmid Maxi Kit (Qiagen, Valencia, Calif.) for use in cell-free protein synthesis (CFPS). All mutants were constructed using QuikChange PCR (Stratagene, La Jolla, Calif.).

Sequences of HBc protein variants. The sequences of wild-type, HBc(D78M), HBc(ST) and HBc(HP) were shown in the table below. HBc(D78M), HBc(ST), and HBc(HP) were stabilized by introducing new disulfide bridge SS1(D29C-R127C). All sequences include the SS1 mutations and the M66S mutation (underlined).

TABLE 3

| Variants | Protein sequence | DNA encoding sequence |
|---|---|---|
| Wild-type (UniProt accession number P03147, truncated at 149) | MDIDPYKEFGATVEL LSFLPSDFFPSVRDL LDTAAALYRDALESP EHCSPHHTALRQAIL CWGDLMTLATWVG TNLEDPASRDLVVS YVNTNVGLKFRQLL WFHISCLTFGRETVL EYLVSFGVWIRTPP AYRPPNAPILSTLPE TTVV (SEQ ID NO: 32) | ATGGATATCGACCCGTACAAAGAATTCGGCGCGACCGTTGAA CTGCTGTCTTTCCTGCCGTCTGATTTCTTCCCGTCTGTTCGTG ACCTGCTGGACACCGCGGCAGCACTGTACCGTGACGCGCTG GAATCTCCGGAACATTGTTCTCCGCATCACACTGCGCTGCGT CAGGCGATTCTGTGCTGGGGCGACCTGATGACCCTGGCGAC TTGGGTTGGCACCAACCTGGAAGATCCGGCGTCTCGTGATC TGGTTGTTTCTTACGTTAACACTAACGTTGGTCTGAAATTCCG TCAGCTGCTGTGGTTCCACATCTCTTGCCTGACCTTCGGTCG TGAAACCGTTCTGGAATACCTGGTTTCTTTTGGTGTTTGGATT CGTACTCCGCCGGCTTACCGTCCGCCGAACGCACCGATCCT GAGCACCCTGCCGGAAACCACTGTTGTGTAATAA |
| HBc(D78M) | MDIDPYKEFGATVEL LSFLPSDFFPSVRCL LDTAAALYRDALESP EHCSPHHTALRQAIL CWGDLSTLATWVG TNLEMPASRDLVVS YVNTNVGLKFRQLL WFHISCLTFGRETVL EYLVSFGVWICTPP AYRPPNAPILSTLPE TTVV (SEQ ID NO: 33) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGATTCTGTGCTGGGGCGACCTG*agc*ACCCTGGCGACT TGGGTTGGCACCAACCTGGAA*atg*CCGGCGTCTCGTGATCTG GTTGTTTCTTACGTTAACACTAACGTTGGTCTGAAATTCCGTC AGCTGCTGTGGTTCCACATCTCTTGCCTGACCTTCGGTCGTG AAACCGTTCTGGAATACCTGGTTTCTTTTGGTGTTTGGATTTGT ACTCCGCCGGCTTACCGTCCGCCGAACGCACCGATCCTGA GCACCCTGCCGGAAACCACTGTTGIGTAATAA |
| HBc(ST) | MDIDPYKEFGATVEL LSFLPSDFFPSVRCL LDTAAALYRDALESP EHCSPHHTALRQAIL CWGDLSTLATWVG NNMQDQAARDLVV SYVNTNVGLKFRQL LWFHISCLTFGRETV | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGATTCTGTGCTGGGGCGACCTG*agc*ACCCTGGCGACT TGGGTTGGC*AACAAC*at*g*CAGGATCAGGCGGCGCGTGATCTG GTTGTTTCTTACGTTAACACTAACGTTGGTCTGAAATTCCGTC AGCTGCTGTGGTTCCACATCTCTTGCCTGACCTTCGGTCGTG |

TABLE 3-continued

| Variants | Protein sequence | DNA encoding sequence |
|---|---|---|
| | LEYLVSFGVWICTPP AYRPPNAPILSTLPE TTVV (SEQ ID NO: 34) | AAACCGTTCTGGAATACCTGGTTTCTTTTGGTGTTTGGATTTGT ACTCCGCCGGCTTACCGTCCGCCGAACGCACCGATCCTGA GCACCCTGCCGGAAACCACTGTTGTGTAATAA |
| HBc(HP) | MDIDPYKEFGATVEL LSFLPSDFFPSVRCL LDTAAALYRDALESP EHCSPHHTALRQAV SCWREVTDFGDWV GNNMQDQAARDLV VNYVNANIGLKIRQL LWFHISCLTFGRETV LEYLVSFGVWICTPP AYRPPNAPILSTLPE TTVV (SEQ ID NO: 35) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAAC*atg*CAGGATCAGGCGGCGCGCGATCT GGTGGTGAACTATGTGAACGCGAACATTGGCCTGAAAATTCG TCAGCTGCTGTGGTTCCACATCTCTTGCCTGACCTTCGGTCG TGAAACCGTTCTGGAATACCTGGTTTCTTTTGGTGTTTGGATT TGTACTCCGCCGGCTTACCGTCCGCCGAACGCACCGATCCT GAGCACCCTGCCGGAAACCACTGTTGTGTAATAA |

The DNA encoding sequences for Wild-type (UniProt accession number P03147, truncated at 149), HBc(D78M), HBc(ST) and HBc(HP) have the following SEQ ID NOs: SEQ ID NO: 84, SEQ ID NO: 85, SEQ ID NO: 86 and SEQ ID NO: 87, respectively.

The sequences of HBc(HP) with different AHA sites are shown in the table below. They were all stabilized by introducing new disulfide bridges SS1(D29C-R127C). AHA signifies azidohomoalanine, the non-natural amino acid tested.

TABLE 4

| Variants | Protein sequence | DNA encoding sequence |
|---|---|---|
| HBc(HP), N75AHA | (AHA)DIDPYKEFGAT VELLSFLPSDFFPSV RCLLDTAAALYRDAL ESPEHCSPHHTALR QAVSCWREVTDFG DWVGN(AHA)LQDQ AARDLVVNYVNANI GLKIRQLLWFHISCL TFGRETVLEYLVSF GVWICTPPAYRPPN APILSTLPETTVV (SEQ ID NO: 36) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAAC*atg*CTGCAGGATCAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TTGTACTCCGCCGGCTTACCGTCCGCCGAACGCACCGATCC TGAGCACCCTGCCGGAAACCACTGTTGTGTAATAA |
| HBc(HP), L76AHA | (AHA)DIDPYKEFGAT VELLSFLPSDFFPSV RCLLDTAAALYRDAL ESPEHCSPHHTALR QAVSCWREVTDFG DWVGNN(AHA)QDQ AARDLVVNYVNANI GLKIRQLLWFHISCL TFGRETVLEYLVSF GVWICTPPAYRPPN APILSTLPETTVV (SEQ ID NO: 37) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAAC*atg*CAGGATCAGGCGGCGCGCGATCT GGTGGTGAACTATGTGAACGCGAACATTGGCCTGAAAATTCG TCAGCTGCTGTGGTTCCACATCTCTTGCCTGACCTTCGGTCG TGAAACCGTTCTGGAATACCTGGTTTCTTTTGGTGTTTGGATT TGTACTCCGCCGGCTTACCGTCCGCCGAACGCACCGATCCT GAGCACCCTGCCGGAAACCACTGTTGTGTAATAA |
| HBc(HP), Q77AHA | (AHA)DIDPYKEFGAT VELLSFLPSDFFPSV RCLLDTAAALYRDAL ESPEHCSPHHTALR QAVSCWREVTDFG DWVGNNL(AHA)DQ AARDLVVNYVNANI GLKIRQLLWFHISCL TFGRETVLEYLVSF GVWICTPPAYRPPN APILSTLPETTVV (SEQ ID NO: 38) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTG*atg*ATCAGGCGGCGCGCGATCT GGTGGTGAACTATGTGAACGCGAACATTGGCCTGAAAATTCG TCAGCTGCTGTGGTTCCACATCTCTTGCCTGACCTTCGGTCG TGAAACCGTTCTGGAATACCTGGTTTCTTTTGGTGTTTGGATT TGTACTCCGCCGGCTTACCGTCCGCCGAACGCACCGATCCT GAGCACCCTGCCGGAAACCACTGTTGTGTAATAA |
| HBc(HP), D78AHA | (AHA)DIDPYKEFGAT VELLSFLPSDFFPSV RCLLDTAAALYRDAL ESPEHCSPHHTALR QAVSCWREVTDFG DWVGNNLQ(AHA)Q AARDLVVNYVNANI | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC |

TABLE 4-continued

| Variants | Protein sequence | DNA encoding sequence |
|---|---|---|
| | GLKIRQLLWFHISCL TFGRETVLEYLVSF GVWICTPPAYRPPN APILSTLPETTVV (SEQ ID NO: 39) | GTCAGCTGCTGTGGTTCCACATCTCTTGCCTGACCTTCGGTC GTGAAACCGTTCTGGAATACCTGGTTTCTTTTGGTGTTTGGAT TTGTACTCCGCCGGCTTACCGTCCGCCAACGCACCGATCC TGAGCACCCTGCCGGAAACCACTGTTGTGTAATAA |
| HBc(HP), Q79AHA | (AHA)DIDPYKEFGAT VELLSFLPSDFFPSV RCLLDTAAALYRDAL ESPEHCSPHHTALR QAVSCWREVTDFG DWVGNNLQD**(AHA)** AARDLVVNYVNANI GLKIRQLLWFHISCL TFGRETVLEYLVSF GVWICTPPAYRPPN APILSTLPETTVV (SEQ ID NO: 40) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAGGA*tatg*GCGGCGCGCGATCT GGTGGTGAACTATGTGAACGCGAACATTGGCCTGAAAATTCG TCAGCTGCTGTGGTTCCACATCTCTTGCCTGACCTTCGGTCG TGAAACCGTTCTGGAATACCTGGTTTCTTTTGGTGTTTGGATT TGTACTCCGCCGGCTTACCGTCCGCCAACGCACCGATCCT GAGCACCCTGCCGGAAACCACTGTTGTGTAATAA |
| HBc(HP), A80AHA | (AHA)DIDPYKEFGAT VELLSFLPSDFFPSV RCLLDTAAALYRDAL ESPEHCSPHHTALR QAVSCWREVTDFG DWVGNNLQDQ**(AHA)** ARDLVVNYVNANIG LKIRQLLWFHISCLT FGRETVLEYLVSFG VWICIPPAYRPPNA PILSTLPETTVV (SEQ ID NO: 41) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAGGATCAG*atg*GCGCGCGATCT GGTGGTGAACTATGTGAACGCGAACATTGGCCTGAAAATTCG TCAGCTGCTGTGGTTCCACATCTCTTGCCTGACCTTCGGTCG TGAAACCGTTCTGGAATACCTGGTTTCTTTTGGTGTTTGGATT TGTACTCCGCCGGCTTACCGTCCGCCAACGCACCGATCCT GAGCACCCTGCCGGAAACCACTGTTGTGTAATAA |

The HBc(HP) DNA encoding sequences for N75AHA, L76AHA, Q77AHA, D78AHA, Q79AHA and A80AHA have the following SEQ ID NOs: SEQ ID NO: 88, SEQ ID NO: 89, SEQ ID NO: 90, SEQ ID NO: 91, SEQ ID NO: 92 and SEQ ID NO: 93, respectively.

The sequences of HBc(HP) D78AHA with different disulfide bond sites are shown in the table below. AHA signifies azidohomoalanine, the non-natural amino acid tested.

The sequences of HBc(HP) D78AHA with different disulfide bond sites are shown in the table below. AHA signifies azidohomoalanine, the non-natural amino acid tested.

TABLE 5

| Variants | Protein sequence | DNA encoding sequence |
|---|---|---|
| HBc(HP) D78AHA, SS1: D29C- R127C | (AHA)DIDPYKEFGAT VELLSFLPSDFFPSV RCLLDTAAALYRDAL ESPEHCSPHHTALR QAVSCWREVTDFG DWVGNNLQ**(AHA)**Q AARDLVVNYVNANI GLKIRQLLWFHISCL TFGRETVLEYLVSF GVWICTPPAYRPPN APILSTLPETTVV (SEQ ID NO: 42) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TTGTACTCCGCCGGCTTACCGTCCGCCAACGCACCGATCC TGAGCACCCTGCCGGAAACCACTGTTGTGTAATAA |
| HBc(HP) D78AHA, SS2: T109C- V120C | (AHA)DIDPYKEFGAT VELLSFLPSDFFPSV RDLLDTAAALYRDAL ESPEHCSPHHTALR QAVSCWREVTDFG DWVGNNLQ**(AHA)**Q AARDLVVNYVNANI GLKIRQLLWFHISCL CFGRETVLEYCSF GVWIRTPPAYRPPN APILSTLPETTVV (SEQ ID NO: 43) | ATGGATATCGACCCGTACAAAGAATTCGGCGCGACCGTTGAA CTGCTGTCTTTCCTGCCGTCTGATTTCTTCCCGTCTGTTCGTG ACCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGIGGTTCCACATCTCTTGCCTGTGCTTCGGTC GTGAAACCGTTCTGGAATACCTGTGTTCTTTTGGTGTTTGGAT TCGTACTCCGCCGGCTTACCGTCCGCCAACGCACCGATCCT GAGCACCCTGCCGGAAACCACTGTTGTGTAATAA |
| HBc(HP) D78AHA, SS3: Y132C- | (AHA)DIDPYKEFGAT VELLSFLPSDFFPSV RDLLDTAAALYRDAL | ATGGATATCGACCCGTACAAAGAATTCGGCGCGACCGTTGAA CTGCTGTCTTTCCTGCCGTCTGATTTCTTCCCGTCTGTTCGTG ACCTGCTGGACACCGCGGCAGCACTGTACCGTGACGCGCTG |

TABLE 5-continued

| Variants | Protein sequence | DNA encoding sequence |
|---|---|---|
| N136C | ESPEHCSPHHTALR QAVSCWREVTDFG DWVGNNLQ(AHA)Q AARDLVVNYVNANI GLKIRQLLWFHISCL TFGRETVLEYLVSF GVWIRTPPACRPPC APILSTLPETTVV (SEQ ID NO: 44) | GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTGCCGTCCGCCGTGCGCACCGATCC TGAGCACCCTGCCGGAAACCACTGTTGTGTAATAA |
| HBc(HP) D78AHA, SS4: Y132C- A137C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAC**RPPN CPILSTLPETTVV (SEQ ID NO: 45) | ATGGATATCGACCCGTACAAAGAATTCGGCGCGACCGTTGAA CTGCTGTCTTTCCTGCCGTCTGATTTCTTCCCGTCTGTTCGTG ACCGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTGCCGTCCGCCGAACTGCCCGATCC TGAGCACCCTGCCGGAAACCACTGTTGTGTAATAA |
| HBc(HP) D78AHA, SS5: R133C- N136C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYCPPC** APILSTLPETTVV (SEQ ID NO: 46) | ATGGATATCGACCCGTACAAAGAATTCGGCGCGACCGTTGAA CTGCTGTCTTTCCTGCCGTCTGATTTCTTCCCGTCTGTTCGTG ACCGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACTGCCCGCCGTGCGCACCGATCC TGAGCACCCTGCCGGAAACCACTGTTGTGTAATAA |
| HBc(HP) D78AHA, SS6: R133C- A137C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYC**PPN CPILSTLPETTVV (SEQ ID NO: 47) | ATGGATATCGACCCGTACAAAGAATTCGGCGCGACCGTTGAA CTGCTGTCTTTCCTGCCGTCTGATTTCTTCCCGTCTGTTCGTG ACCGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACTGCCCGCCGAACTGCCCGATCC TGAGCACCCTGCCGGAAACCACTGTTGTGTAATAA |
| HBc(HP) D78AHA, SS7: P134C- P135C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYRCC**N APILSTLPETTVV (SEQ ID NO: 48) | ATGGATATCGACCCGTACAAAGAATTCGGCGCGACCGTTGAA CTGCTGTCTTTCCTGCCGTCTGATTTCTTCCCGTCTGTTCGTG ACCGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACCTGCTGCAACGCACCGATCCT GAGCACCCTGCCGGAAACCACTGTTGTGTAATAA |
| HBc(HP) D78AHA, SS8: P134C- N136C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYRCPC** APILSTLPETTVV (SEQ ID NO: 49) | ATGGATATCGACCCGTACAAAGAATTCGGCGCGACCGTTGAA CTGCTGTCTTTCCTGCCGTCTGATTTCTTCCCGTCTGTTCGTG ACCGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAG*atg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACCTGCCCGTGCGCACCGATCCT GAGCACCCTGCCGGAAACCACTGTTGTGTAATAA |
| HBc(HP) D78AHA, | (AHA)DIDPYKEFGAT VELLSFLPSDFFPSV | ATGGATATCGACCCGTACAAAGAATTCGGCGCGACCGTTGAA CTGCTGTCTTTCCTGCCGTCTGATTTCTTCCCGTCTGTTCGTG |

TABLE 5-continued

| Variants | Protein sequence | DNA encoding sequence |
|---|---|---|
| SS9: P134C-A137C | RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYRC**PN CPILSTLPETTV (SEQ ID NO: 50) | ACCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAGa*tg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACCGTTGCCCGAACTGCCCGATCC TGAGCACCCTGCCGGAAACCACTGTTGTGTAATAA |
| HBc(HP) D78AHA, SS10: P135C-N136C | (AHA)DIDPYKEFGAT VELLSFLPSDFFPSV RDLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWIRTPPAYRPCC** APILSTLPETTVV (SEQ ID NO: 51) | ATGGATATCGACCCGTACAAAGAATTCGGCGCGACCGTTGAA CTGCTGTCTTTCCTGCCGTCTGATTTCTTCCCGTCTGTTCGTG ACCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGIGGGCAACAACCTGCAGa*tg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TCGTACTCCGCCGGCTTACCGTCCGTGCTGCGCACCGATCC TGAGCACCCTGCCGGAAACCACTGTTGTGTAATAA |
| HBc(HP) D78AHA, SS1 + SS8: (D29C-R127C) + (P134C-N136C) | (AHA)DIDPYKEFGAT VELLSFLPSDFFPSV RCLLDTAAALYRDAL ESPEHCSPHHTALR QAVSCWREVTDFG DWVGNNLQ**(AHA)Q AARDLVVNYVNANI GLKIRQLLWFHISCL TFGRETVLEYLVSF GVWICIPPAYRCPC** APILSTLPETTVV (SEQ ID NO: 52) | ATGGATATCGACCCGTACAAAGAATTCGGCGCGACCGTTGAA CTGCTGTCTTTCCTGCCGTCTGATTTCTTCCCGTCTGTTCGTT GCCTGCTGGACACCGCGGCAGCACTGTACCGTGACGCGCTG GAATCTCCGGAACATTGTTCTCCGCATCACACTGCGCTGCGT CAGGCGGTGAGCTGCTGGCGCGAAGTGACCGATTTTGGCGA TTGGGTGGGCAACAACCTGCAGa*tg*CAGGCGGCGCGCGATC TGGTGGTGAACTATGTGAACGCGAACATTGGCCTGAAAATTC GTCAGCTGCTGTGGTTCCACATCTCTTGCCTGACCTTCGGTC GTGAAACCGTTCTGGAATACCTGGTTTCTTTTGGTGTTTGGAT TTGTACTCCGCCGGCTTACCGTTGCCCGTGCGCACCGATCC TGAGCACCCTGCCGGAAACCACTGTTGTGTAATAA |

The HBc(HP) D78AHA DNA encoding sequences for SS1:D29C-R127C, SS2:T109C-V120C, SS3:Y132C-N136C, SS4:Y132C-A137C, SS5:R133C-N136C, SS6: R133C-A137C, SS7:P134C-P135C, SS8:P134C-N136C, SS9:P134C-A137C, SS10:P135C-N136C and SS1+SS8: (D29C-R127C) +(P134C-N136C) have the following SEQ ID NOs: SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103 and SEQ ID NO: 104.

Cell-free protein synthesis (CFPS). CFPS was conducted using the PANOx-SP (PEP, amino acids, nicotinamide adenine dinucleotide (NAD), oxalic acid, spermidine, and putrescine) cell-free system as described previously (Jewett and Swartz 2004) with several modifications. The standard PANOx-SP CFPS reaction mixture includes: 1.2 mM ATP, 0.85 mM each of GTP, UTP, and CTP, 33 mM phosphoenol pyruvate (Roche Molecular Biochemicals, Indianapolis, Ind.), 170 mM potassium glutamate, 10 mM ammonium glutamate, 16 mM magnesium glutamate, 1.5 mM spermidine, 1.0 mM putrescine, 0.17 mg/mL folinic acid, 45 μg/mL plasmid, approximately 100-300 μg/mL T7 RNA polymerase, 2 mM of each of the 20 unlabeled amino acids, 0.33 mM NAD, 0.26 mM Coenzyme A (CoA), 2.7 mM potassium oxalate, and 0.28 volumes of E. coli KC6 S30 extract (Goerke and Swartz 2008). For global replacement of methionines in HBc proteins, methionine was left out of cell-free reaction mixtures, and substituted by 1 mM azido-homoalanine (AHA) (Medchem Source LLP, Federal Way, Wash.), a non-natural amino acid that displays an azide moiety. All reagents were obtained from Sigma-Aldrich (St. Louis, Mo.) unless otherwise noted.

CFPS reactions to produce the HBc protein were conducted at 30° C. for 6 h. Small-scale CFPS reactions were carried out in 20 μL volumes in 1.5 mL microcentrifuge tubes. Preparative-scale reactions used 6 mL volumes with 1 mL per well in 6-well tissue culture plates (BD Falcon #3046, BD, Franklin Lakes, N.J.). 8.4 μM L-[U-$^{14}$C]-Leucine (PerkinElmer, Waltham, Mass.) was added to small-scale reactions and to 20 μL aliquots of preparative-scale reactions for measuring protein yields using a previously described trichloroacetic acid protein precipitation protocol (Calhoun and Swartz 2005) and a Beckman LS3801 liquid scintillation counter (Beckman Coulter, Fullerton, Calif.).

The production of GM-CSF, IM9-ScFv and CpG DNA with an alkyne moiety were described by Patel et al. The production of flagellin with an alkyne moiety was described by Lu et al.

Size-exclusion chromatography (SEC). To remove unincorporated L-[U-14C] leucine, the cell-free product was immediately dialyzed in 6-8000 MWCO Specra/Pro Molecularporous Membrane Tubing (Spectrum Labs, Rancho Dominguez, Calif.) against Dialysis Buffer (10 mM Tris-HCl, pH 7.4, 1.5 M NaCl) with 1 mM DTT with 2 buffer exchanges. The dialyzed cell-free reaction product was loaded on an SEC (size-exclusion chromatography) column packed with Sepharose 6 FastFlow resin (GE Healthcare). The running buffer is as the dialysis buffer with 5 mM DTT. The protein concentrations of eluate fractions were determined based on radioactivity.

Sucrose gradient sedimentation. The isolated VLPs from SEC were firstly dialyzed against the Dialysis Buffer to remove DTT, and were then oxidized to form disulfide bonds by adding 10 mM H₂O₂ or 10 mM diamide and incubating at room temperature for 1 h. The oxidants were removed by dialysis against the Dialysis Buffer with 2 buffer exchanges. The oxidized VLPs were assessed by velocity sedimentation. Ten to forty percentage weight per volume continuous sucrose density gradients were prepared in Dialysis Buffer in Polyallose 16×102 mm Centrifuge Tubes (Beckman) with the Gradient Master Ver3.05L Gradient Maker (Biocomp Instruments, Inc., Fredericton, Canada). The VLP product (200 µL) was layered on top of the sucrose and centrifuged at 31,000 rpm in a Beckman Coulter SW-32.1 swinging bucket rotor (Fullerton, Calif.) in a Beckman L8-M ultracentrifuge at 4° C. for 7 h with profile 7 slow acceleration and deceleration. One-half milliliter fractions were collected and the concentration in each fraction was determined by radioactivity measurement.

SDS-PAGE and autoradiogram. Protein size was analyzed by SDS-PAGE and autoradiography. NuPAGE Novex precast gels and reagents were purchased from Invitrogen (Carlsbad, Calif.). For reducing SDS-PAGE, samples were denatured for 10 min at 95° C. in loading buffer (1× LDS running buffer and 50 mM dithiothreitol). For non-reducing SDS-PAGE, samples were only mixed with LDS running buffer, without addition of dithiothreitol and heat treatment. The samples were loaded onto a 10% (w/v) Bis-Tris precast gel with SeeBlue Plus2 molecular weight protein standard, and electrophoresed in MES/SDS running buffer. SimplyBlue SafeStain was used to stain and fix the gels according to the manufacturer's recommendations. The gels were dried using a gel dryer model 583 (Bio-Rad, Richmond, Calif.), before exposure to a storage phosphor screen (Molecular Dynamics), which was subsequently scanned using a Typhoon Scanner (GE Healthcare).

Azide-Alkyne conjugation and purification. The [3+2] cycloaddition click reactions were conducted in an anaerobic glovebox (Coy Laboratories, Grass Lake, Mich.) to preserve the reduced state of the tetrakis(acetonitrile)copper (I)hexafluorophosphate catalyst ([(CH3CN)4Cu]PF6 or simply Cu (I) catalyst) (Sigma Aldrich, St. Louis, Miss.). Cu (I) catalyst was added to reactions at 1 mM in addition to 0.5 mM of the enhancer ligand, tris(triazolylmethyl) amine (TTMA), to improve the rate of the click reactions. HBc VLPs and functional molecules (flagellin, GM-CSF, IM9-ScFv or CpG DNA) were mixed with the Cu (I) catalyst and TTMA enhancer with 0.01% Tween 20. Before addition of the Cu (I) catalyst, click reaction components were deoxygenated in 1.5 mL microcentrifuge tubes for 1 h in the anaerobic glovebox. The click reactions for attaching functional molecules to HBc VLPs were conducted overnight.

Example 3

This example describes methods for improving VLP production and surface conjugation, and evaluating HBc VLP antigenicity and immunogenicity.

Materials and Methods

Plasmid construction was performed as discussed in Example 1.

The sequences of 10 different variants with different cysteine mutations and 17 different variants with different AHA sites or different negative charge mutations are shown in Table 1 of Example 1 and Tables 6-7.

TABLE S1

The sequences of 15 different HBc variants with different AHA sites or different negative charge mutations.

| Variants | DNA encoding sequence |
|---|---|
| A: L76AHA | ATGGATATCGACCCGTACAAAGAATTCGGCGCGACCGTTGAACTGCTGTCTTTCCTGCCGTCTGATTTCTTCCCGTC<br>TGTTCGTTGCCTGCTGGACACCGCGGCAGCACTGTACCGTGACGCGCTGGAATCTCCGGAACATTGTTCTCCGCAT<br>CACACTGCGCTGCGTCAGGCGATTCTGTGCTGGGGCGACCTGa*gc*ACCCTGGCGACTTGGGTTGGCACCAACAt*g*GA<br>AGATCCGGCGTCTCGTGATCTGGTTGTTTCTTACGTTAACACTAACGTTGGTCTGAAATTCCGTCAGCTGCTGTGGT<br>TCCACATCTCTTGCCTGACCTTCGGTCGTGAAACCGTTCTGGAATACCTGGTTTCTTTTGGTGTTTGGATTTGTACT<br>CCGCCGGCTTACCGTCCGCCGAACGCACCGATCCTGAGCACCCTGCCGGAAACCACTGTTGTGTAATAA |
| B1: D78AHA | ATGGATATCGACCCGTACAAAGAATTCGGCGCGACCGTTGAACTGCTGTCTTTCCTGCCGTCTGATTTCTTCCCGTC<br>TGTTCGTTGCCTGCTGGACACCGCGGCAGCACTGTACCGTGACGCGCTGGAATCTCCGGAACATTGTTCTCCGCAT<br>CACACTGCGCTGCGTCAGGCGATTCTGTGCTGGGGCGACCTGa*aa*ACCCTGGCGACTTGGGTTGGCACCAACCTGG<br>AAat*g*CCGGCGTCTCGTGATCTGGTTGTTTCTTACGTTAACACTAACGTTGGTCTGAAATTCCGTCAGCTGCTGTGGT<br>TCCACATCTCTTGCCTGACCTTCGGTCGTGAAACCGTTCTGGAATACCTGGTTTCTTTTGGTGTTTGGATTTGTACT<br>CCGCCGGCTTACCGTCCGCCGAACGCACCGATCCTGAGCACCCTGCCGGAAACCACTGTTGTGTAATAA |
| B2:<br>D78AHA + E77S | ATGGATATCGACCCGTACAAAGAATTCGGCGCGACCGTTGAACTGCTGTCTTTCCTGCCGTCTGATTTCTTCCCGTC<br>TGTTCGTTGCCTGCTGGACACCGCGGCAGCACTGTACCGTGACGCGCTGGAATCTCCGGAACATTGTTCTCCGCAT<br>CACACTGCGCGCTGCGTCAGGCGATTCTGTGCTGGGGCGACCTGa*gc*ACCCTGGCGACTTGGGTTGGCACCAACCTa*g*<br>*catg*CCGGCGTCTCGTGATCTGGTTGTTTCTTACGTTAACACTAACGTTGGTCTGAAATTCCGTCAGCTGCTGTGGTT<br>CCACATCTCTTGCCTGACCTTCGGTCGTGAAACCGTTCTGGAATACCTGGTTTCTTTTGGTGTTTGGATTTGTACTC<br>CGCCGGCTTACCGTCCGCCGAACGCACCGATCCTGAGCACCCTGCCGGAAACCACTGTTGTGTAATAA |
| C1: P79AHA | ATGGATATCGACCCGTACAAAGAATTCGGCGCGACCGTTGAACTGCTGTCTTTCCTGCCGTCTGATTTCTTCCCGTC<br>TGTTCGTTGCCTGCTGGACACCGCGGCAGCACTGTACCGTGACGCGCTGGAATCTCCGGAACATTGTTCTCCGCAT<br>CACACTGCGCTGCGTCAGGCGATTCTGTGCTGGGGCGACCTGG*atc*ACCCTGGCGACTTGGGTTGGCACCAACCTGG<br>AAGAT*atg*GCGTCTCGTGATCTGGTTGTTTCTTACGTTAACACTAACGTTGGTCTGAAATTCCGTCAGCTGCTGTGGT<br>TCCACATCTCTTGCCTGACCTTCGGTCGTGAAACCGTTCTGGAATACCTGGTTTCTTTTGGTGTTTGGATTTGTACT<br>CCGCCGGCTTACCGTCCGCCGAACGCACCGATCCTGAGCACCCTGCCGGAAACCACTGTTGTGTAATAA |
| C2:<br>P79AHA + E77K | ATGGATATCGACCCGTACAAAGAATTCGGCGCGACCGTTGAACTGCTGTCTTTCCTGCCGTCTGATTTCTTCCCGTC<br>TGTTCGTTGCCTGCTGGACACCGCGGCAGCACTGTACCGTGACGCGCTGGAATCTCCGGAACATTGTTCTCCGCAT<br>CACACTGCGCTGCGTCAGGCGATTCTGTGCTGGGGCGACCTG*agc*ACCCTGGCGACTTGGGTTGGCACCAACCTGa*g*<br>*a*GAT*atg*GCGTCTCGTGATCTGGTTGTTTCTTACGTTAACACTAACGTTGGTCTGAAATTCCGTCAGCTGCTGTGGT<br>TCCACATCTCTTGCCTGACCTTCGGTCGTGAAACCGTTCTGGAATACCTGGTTTCTTTTGGTGTTTGGATTTGTACTC<br>CGCCGGCTTACCGTCCGCCGAACGCACCGATCCTGAGCACCCTGCCGGAAACCACTGTTGTGTAATAA |

TABLE S1-continued

The sequences of 15 different HBc variants with different AHA sites or different negative charge mutations.

| Variants | DNA encoding sequence |
|---|---|
| C3: P79AHA + D78K | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGG AAagcataGCGTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| C4: P79AHA + E77S | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGag gGATatgGCGTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| C5: P79AHA + D78S | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCTGCGTCAGGCGATTCTGTGCTGGGGCGACCTGagcACCCTGGCGACTTGGGTTGGCACCAACCTGG AAagcatgGCGTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| C6: P79AHA + E77S + D78S | ATGGATATCGACCCGTACAAAGAATTCGGCGCGACCGTTGAACTGCTGTCTTTCCTGCCGTCTGATTTCTTCCCGTC +TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGag agcataGCGTCTCGTGATCTGGTTGTTTCTTACGTTAACACTAACGTTGGTCTGAAATTCCGTCAGCTGCTGTGGTT CACATCTCTTGCCTGACCTTCGGTCGTGAAACCGTTCTGGAATACCTGGTTTCTTTTGGTGTTTGGATTTGTACTCC GCCGGCTTACCGTCCGCCGAACGCACCGATCCTGAGCACCCTGCCGGAAACCACTGTTGTGTAATAA |
| D1: A80AHA | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTTGCCTGCGTCAGGCGATTCTGTGCTGGGGCGACCTGagcACCCTGGCGACTTGGGTTGGCACCAACCTGG AAGATCCGatgTCTCGTGATCTGGTTGTTTCTTACGTTAACACTAACGTTGGTCTGAAATTCCGTCAGCTGCTGTGGT TCCACATCTCTTGCCTGACCTTCGGTCGTGAAACCGTTCTGGAATACCTGGTTTCTTTTGGTGTTTGGATTTGTACT CCGCCGGCTTACCGTCCGCCGAACGCACCGATCCTGAGCACCCTGCCGGAAACCACTGTTGTGTAATAA |
| D2: A80AHA + E77K | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTag cGATCCCatgTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| D3: A80AHA + D78K | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGG AAaaaCCatgTCTCGTGATCTGGTTGTTTCTTACGTTAACACTAAGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| D4: A80AHA + E77S | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGaGCGTCTCAGGCGATTCTGTGCTGGGGCGACCTGagcACCCTGGCGACTTGGGTTGGCACCAACCTGag cGATCCGatgTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| D5: A80AHA + D78S | ATGGATATCGACCCGTACAAAGAATTCGGCGCGACCGTTGAACTGCTGTCTTTCCTGCCGTCTGATTTCTTCCCGTC TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGG AAatcCCatgTCTCGTGATCTGGTTGTTTCTTACGTTAACACTAACGTTGGTCTGAAATTCCGTCAGCTGCTGTGGTT CCACATCTCTTGCCTGACCTTCGGTCGTGAAACCGTTCTGGAATACCTGGTTTCTTTTGGTGTTTGGATTTGTACTC CGCCGGCTTACCGTCCGCCGAACGCACCGATCCTGAGCACCCTGCCGGAAACCACTGTTGTGTAATAA |
| D6: A80AHA + E77S + D78S | ATGGATATCGACCCGTACAAAGAATTCGGCGCGACCGTTGAACTGCTGTCTTTCCTGCCGTCTGATTTCTTCCCGTC +TGTTCGTTGCCTGCTGGACACCGCGGCAGCACTGTACCGTGACGCGCTGGAATCTCCGGAACATTGTTCTCCGCAT CACACTGCGCTGCGTCAGGCGATTCTGTGCTGGGGCGACCTGagcACCCTGGCGACTTGGGTTGGCACCAACCTGag cataCCatgCTCGTGATCTGGTTGTTTCTTACGTTAACACTAAGTTGGTCTGAAATTCCGTCAGCTGCTGTGGTTC CACATCTCTTGCCTGACCTTCGGTCGTGAAACCGTTCTGGAATACCTGGTTTCTTTTGGTGTTTGGATTTGTACTCC GCCGGCTTACCGTCCGCCGAACGCACCGATCCTGAGCACCCTGCCGGAAACCACTGTTGTGTAATAA |

A: L76AHA is shown in SEQ ID NO: 55 or 66, B1: D78AHA is shown in SEQ ID NO: 68 or 85, B2: D78AHA +E77S is shown in SEQ ID NO: 69, C1: P79AHA is shown in SEQ ID NO: 72, C2: P79AHA +E77K is shown in SEQ ID NO: 73, C3: P79AHA +D78K is shown in SEQ ID NO: 74, C4: P79AHA+E77S is shown in SEQ ID NO: 75, C5: P79AHA +D78S is shown in SEQ ID NO: 76, C6: P79AHA+E77S +D78S is shown in SEQ ID NO: 77, D1: A80AHA is shown in SEQ ID NO: 78, D2: A80AHA +E77K is shown in SEQ ID NO: 79, D3: A80AHA+D78K is shown in SEQ ID NO: 80, D4: A80AHA+E77S is shown in SEQ ID NO: 81, D5: A80AHA+D78S is shown in SEQ ID NO: 82 and D6: A80AHA+E77S+D78S is shown in SEQ ID NO: 83.

uranyl acetate, pH 4. Photographs were taken with a Gatan Orius CCD camera in a JEOL JEM1400 electron microscope at 120 kV acceleration voltage.

Immunization of mice. Six- to eight-week-old BALB/c mice were obtained and housed at the Laboratory Animal Facility at Stanford University Medical Center (Stanford, Calif.). All animal experiments were conducted following the Laboratory Animal Facility and National Institute of Health guidelines. The study protocol was approved by the Stanford University Institutional Animal Care and Use Committee. Ten mice per group were vaccinated intradermally with 3 μg KLH or HBc VLP formulated in PBS buffer. The endotoxin levels in the injected solutions are <0.04 EU/dose. Mice were vaccinated on days 0, 10 and 20, and retro-orbital

TABLE S2

The sequences of SS1(b1), SS1(ST), and SS1(HP).

| Protein sequence Variants (with nnAA AHA) | DNA encoding sequence |
|---|---|
| SS1(B1) (AHA)DIDPYKEPGATVELLSFLPS DFFPSVRCLLDTAAALYRDALESPE HCSPHHTALRQAILCWGDLSLATW VGTNLE**(AHA)PASRDLVVSYVNTN VGLKFRQLLWFHISCLTPGRETVLE YLVSFGVWIC**TPPAYRPPNAPILST LPETTVV | ATGGATATCGACCCGTACAAAGAATTCGGCGCGACCGTTGAACTGCTGTCTTTCC TGCCGTCTGTCTTCCCGTCTGTTCGTTGCCTGCTGGACACCGCGGCAGCACTG TACCGTGACGCGCTGGAATCTCCGGAACATTGTTCTCCGCATCACACTGCGCTGC GTCAGGCGATTCTGTGCTGGGGCGACCTGagcACCCTGGCGACTTGGGTTGGCACC AACCTGGAAatgCCGGCGTCTCGTGATCTGGTTGTTTCTTACGTTAACACTAACGTT GGTCTGAAATTCCGTCAGCTGCTGTGGTTCCACATCTCTTGCCTGACCTTCGGTCG TGAAACCGTTCTGGAATACCTGGTTTCTTTTGGTGTTTGGATTTGTACTCCGCCGG CTTACCGTCCGCCGAACGCACCGATCCTGAGCACCCTGCCGGAAACCACTGTTGT GTAATAA |
| SS1(ST) (AHA)DIDPYKEFGATVELLSFLPS DFFPSVRCLLDTAAALYRDALESPE HCSPHHTALRQAILCWGDLSTLATW VGNN(AHA)QDQAARDLVVSYVNTN VGLKFRQLLWFHISCLTPGRETVLE YLVSFGVWICTPPAYRPPNAPILST LPETTVV | ATGGATATCGACCCGTACAAAGAATTCGGCGCGACCGTTGAACTGCTGTCTTTCC TGCCGTCTGATTTCTTCCCGTCTGTTCGTTGTCTGCTGGACACCGCGGCAGCACTG TACCGTGACGCGCTGGAATCTCCGGAACATTGTTCTCCGCATCACACTGCGCTGC GTCAGGCGATTCTGTGCTGGGGCGACCTGagcACCCTGGCGACTTGGGTTGGC<u>AAC AAC</u>atgCAGGATCAGGCGGCGCGTGATCTGGTTGTTTCTTACGTTAACACTAACGT TGGTCTGAAATTCCGTCAGCTGCTGTGGTTCCACATCTCTTGCCTGACCTTCGGTC GTGAAACCGTTCTGGAATACCTGGTTTCTTTTGGTGTTTGGATTTGTACTCCGCCG GCTTACCGTCCGCCGAACGCACCGATCCTGAGCACCCTGCCGGAAACCACTGTTG TGTAATAA |
| SS1(HP) (AHA)DIDPYKEFGATVELLSFLPS DFFPSVRCLLDTAAALYRDALESPE HCSPHHTALRQAVSCWREVTDFGDW VGNN(AHA)QDQAARDLVVNYVNAN IGLKIRQLLWFHISCLTFGRETVLE YLVSFGVWICTPPAYRPPNAPILST LPETTVV | ATGGATATCGACCCGTACAAAGAATTCGGCGCGACCGTTGAACTGCTGTCTTTCC TGCCGTCTGATTTCTTCCCGTCTGTTCGTTGCCTGCTGGACACCGCGGCAGCACTG TACCGTGACGCGCTGGAATCTCCGGAACATTGTTCTCCGCATCACACTGCGCTGC GTCAGGCGGTGAGCTGCTGGCGCGAAGTGACCGATTTTGGCGATTGGGTGGGCA ACAACatgCAGGATCAGGCGGCGCGCGATCTGGTGGTGAACTATGTGAACGCGAA CATTGGCCTGAAAATTCGTCAGCTGCTGTGGTTCCACATCTCTTGCCTGACCTTCG GTCGTGAAACCGTTCTGGAATACCTGGTTTCTTTTGGTGTTTGGATTTGTACTCCG CCGGCTTACCGTCCGCCGAACGCACCGATCCTGAGCACCCTGCCGGAAACCACTG TTGTGTAATAA |

The Protein sequences (with nnAA AHA) for SS1(B1), SS1(ST) and SS1(HP) are SEQ ID NO: 108, SEQ ID NO: 109 and SEQ ID NO: 110, respectively. The DNA encoding sequences for SS1(B1), SS1(ST) and SS1(HP) are SEQ ID NO: 68 or 85, SEQ ID NO: 86 and SEQ ID NO: 87 or 89, respectively.

Cell-Free Protein Synthesis (CFPS) was conducted as described in Example 1.

Size-exclusion chromatography (SEC) was performed as described in Example 1.

Sucrose gradient sedimentation was performed as described in Example 1.

SDS-PAGE and autoradiography were performed as described in Example 1.

Purification of HBc VLPs was performed as described in Example 1.

Azide-Alkyne conjugation and purification was performed as described in Example 1.

Transmission electron microscopy. A 5 μL sample of a purified 5 nM VLP solution was applied to a carbon coated copper/Formvar grid and negatively stained with 1% w/v bled on days 9, 19 and 29 to assess immune responses. On day 36, the spleens were removed from three mice per group for T-cell proliferation assay.

ELISA assay. In an enzyme-linked immunosorbent assay (ELISA), 50 μL of antigen proteins at 1 μg/mL concentrations were coated on 96-well ELISA plates (NUNC MaxiSorp) and allowed to bind overnight at 4° C. Plates were then washed four times with PBS buffer and blocked with Blocking Buffer (PBS buffer with 1% (w/v) BSA) at room temperature for 1 h. After washing four times with Washing Buffer (PBS buffer with 0.05% (w/v) Tween 20), 50 μL of dilutions of mouse sera in Blocking Buffer were then added to the plates and incubated at room temperature for 1 h. Antibody 13A9 (IgG2b) binding to the region AA 135-140 of HBc antigen protein was used as the standard for quantitating the antibody levels. Plates were washed four times again with Washing Buffer before adding 0.1 μg/mL of peroxidase-conjugated monoclonal anti-mouse IgG(H+L) antibody (KPL) in Blocking Buffer and incubating at room temperature for 1 h. Plates were washed six times again with Washing Buffer before developing with 50 μL of Ultra-TMB substrate (Pierce) for 10 min and quenching with 30 μL of 2 M $H_2SO_4$. Each well was measured at $OD_{450}$ using a VersaMax microplate reader. Each data point indicates the mean of triplicate assay results and error bars represent standard deviation.

T-cell proliferation assay. Spleen cells were collected by squeezing the spleen through a 70 pm cell strainer, erythrocytes were removed by ACK lysis buffer (0.15 M $NH_4Cl$, 10 mM $NaHCO_3$, 0.1 mM EDTA, pH 7.3). Splenocytes were cultured at $2 \times 10^5$ cells/well in round-bottom 96-well plates in RPMI 1640 (10% heat-inactivated FBS, 2 mM L-glutamine, 50 pM 2-ME, 100 U/ml penicillin, 100 μg/ml streptomycin sulfate) in the presence of antigens for 4 days. Each well was pulsed with 0.5 μCi [$^3$H]-Thymidine (Amersham, Buckinghamshire, UK) 16 hours before harvesting. All proliferation assays were performed in triplicate. Results are expressed as the stimulation index (SI), which represents the ratio between the mean c.p.m. obtained in the presence and absence of antigen (Aguilar et al., 2004; Kruisbeek et al., 2004).

Results and Discussions

Stabilizing the VLPs. The HBc polypeptide truncated at amino acid 149 has been shown to predominantly form (>95%) T=4 VLPs (Wynne et al., 1999). Two HBc monomers (16.7 kDa) associate into a compact dimer (33.5 kDa) with a potential intermolecular disulfide bond between the Cys-61 residues of the two monomers. Dimers (120 copies) self-assemble into the T=4 VLP by weak interactions (Ceres and Zlotnick, 2002; Kegel and Schoot, 2004) (FIG. 1A). After assembly, the surface of the HBc VLP displays an ordered array of 120 spikes (projecting alpha helices) which can be exploited for the display of foreign molecules (Pumpens and Grens, 2001). The T=4 icosahedral capsid has 12 regular five-fold faces and 30 regular six-fold faces (FIG. 1B). Each pentamer is surrounded by 5 hexamers (FIG. 1C).

In total, 10 pairs of mutations were evaluated, including SS1 (D29C-R127C) and SS2 (T109C-V120C) at the assembly interfaces and SS3 (Y132C-N136C), SS4 (Y132C-A137C), SS5 (R133C-N136C), SS6 (R133C-A137C), SS7 (P134C-P135C), SS8 (P134C-N136C), SS9 (P134C-A137C), and SS10 (P135C-N136C) to connect the C-termini.

To further evaluate the HBc SS1 VLP, its stability was compared to that of the original HBc VLP. Transmission electron microscope (TEM) images (FIG. 2F) demonstrated that the original HBc VLP either did not fully assemble or disassembled during sample preparation, while HBc SS1 VLPs appeared as uniform, fully assembled capsids. We also evaluated stability during incubation under physiological condition. Approximately 50% of the original HBc VLPs disassembled when incubated in physiological PBS buffer overnight, and almost all disassembled when incubated in a low ionic strength buffer (FIG. 2G). However, the HBc SS1 VLP was stable in all of the conditions tested. The HBc SS1 VLP also showed much better stability after a freeze-thaw cycle than the original HBc VLP, as shown in FIG. 2H. Overall, the artificial S—S network in the HBc SS1 VLP confers excellent assembly stability.

Click chemistry conjugation reactions were then tested to further verify the functionality of the oxidized VLPs. Flagellin and GMCSF were used as example proteins for conjugation. CFPS provides a facile means for site-specific introduction of nnAAs with an alkyne moiety into flagellin (HPG, homopropargylglycine) (Lu et al., 2013) and GMCSF (PPF, p-propargyloxy-phenylalanine) (Patel and Swartz, 2011), as well as a nnAA with an azide moiety (AHA, azidohomoalanine) into the L76 site near the tip of the spike region on the VLP surface. This enabled the direct coupling of flagellin and GMCSF to the VLPs using Cu(I)-catalyzed [3+2] cycloaddition click chemistry (FIG. 3G-H) (Deiters and Schultz, 2005; Bundy and Swartz, 2010; Rostovtsev et al., 2002; Strable et al., 2008). The reaction results (FIG. 2I) showed that flagellin and GMCSF were readily conjugated to the HBc SS1 VLP.

Engineering the VLP Surface. At physiological pH, the surface of the HBc VLP is negatively charged as shown in FIG. 7A. The HBc VLP surface is dominated by 120 protruding dimer spikes that serve as obvious attachment sites with high steric availability. However, they are terminated with four negatively charged amino acids (E77×2, D78×2). Initial conjugation tests showed good attachment of GMCSF and flagellin to the stabilized VLPs but poor attachment of 1M9-scFv (a lymphoma vaccine antigen) (Kanter et al., 2007) and CpG DNA (an innate immunity stimulator) (Ohto et al., 2015). The latter two molecules are characterized by negative charge density near the alkyne. We hypothesized that charge repulsion inhibited IM9-scFv and CpG attachment as illustrated in FIG. 7B.

We hypothesized that decreasing the number of negative charges on the HBc VLP surface would allow good conjugations for most attachment molecules. There are 3 negatively charged amino acids (E77, D78 and D83) and 1 positively charged amino acid (R82) on the surface of the monomer spike. We assumed that D83 and R82 could, at least partially, neutralize each other so we targeted the negative charges at the tip of the dimer spike, E77 and D78. To reduce or remove net negative charge, we tested three strategies: reduce negative charge in half (E77S, D78S, or D78AHA), use positive charges to neutralize negative charges (E77K or D78K), or remove all negative charges (E77S+D78AHA or E77S+D78S). At the same time, different AHA sites on the dimer spike were tested. In total 15 mutated forms of the HBc SS1 VLP were evaluated, as summarized in FIG. 7A.

Initial CFPS results showed that changing the AHA sites without decreasing the surface charge did not affect the HBc protein solubility. However, soluble yields decreased greatly for the mutants in which negative surface charge was removed (FIG. 8A). After dialysis against 0.5 M NaCl, the soluble yields of some mutants increased. SEC analyses showed that changing the AHA sites did not affect VLP assembly, but the charge change mutations reduced VLP assembly yields dramatically (FIG. 7C). As the virus capsid assembly is driven by hydrophobic interactions (Kegel and Schoot, 2004), we hypothesized that higher ionic strength would enhance assembly. We saw that dialysis against 1.5 M NaCl greatly improved VLP assembly yields for 10 of the 14 mutants (FIG. 7D). The exceptions are B2, C3, C6, and D6. Three of the four had both negative charges removed at the spike tip of each monomer. In an attempt to improve the soluble yield and VLP assembly of B2, C3, C6, and D6, several approaches were examined (FIGS. 8-13) including: modifying CFPS conditions (salts, metal ions, temperature, detergents, etc.); changing dialysis conditions (pH, temperature, detergents, salts in the Hofmeister series, amino acid additions, etc.); additional mutations (different disulfide bond network, F97L mutation); and the use of various protein refolding additives and conditions (denaturants, pH, redox environment, arginine, detergents, etc.). Notably, all attempts failed to improve VLP assembly. These results suggest that negative charge at the spike tip of the dimer is very important for VLP assembly. Although, we could reduce surface negative charge in half (mutants B1, C4 and D4), and use positive charge to neutralize negative charge (mutants C2, D2 and D3), we could not remove all the negative charge (mutation B2, C6 and D6).

Surface conjugation to these mutated VLPs was then tested. In addition to GMCSF and flagellin, we tested two molecules, IM9-scFv and CpG DNA, which display negative charge density near the alkyne functional group (FIG. 7E). The conjugation reaction results (FIG. 7F) showed that decreasing surface negative charge greatly improved the conjugation efficiency for IM9-scFv and CpG DNA without reducing conjugation of GMCSF and flagellin. The mutant B1 provides the best overall conjugation efficiency and was preferred because it required only a single amino acid mutation. Mutant D2 may also be attractive as it provides good conjugation with better soluble production yields.

Transplanting a rare HBc spike. Reducing the HBc VLP surface charges improved the conjugation of displayed molecules, but production yields were relatively low for these mutated VLPs (FIG. 8A). The best mutant for conjugation, B1, had less than a 50% soluble yield. While optimization of CFPS and dialysis conditions improved product solubility, those changes decreased VLP assembly (FIGS. 8-11). This led us to seek an alternative approach for modifying the HBc dimer spike. Rational design and directed evolution are two general strategies for protein engineering. However, exploring all possible combinations of mutating only three amino acids would require testing of nearly 7000 candidates, which was outside the scope of the current methods. Alternatively, we looked to find clues in naturally occurring viral mutants. In addition to improving VLP production and surface conjugation, we also sought to reduce concerns about the HBc VLP antigenicity and immunogenicity.

Figure 14B:
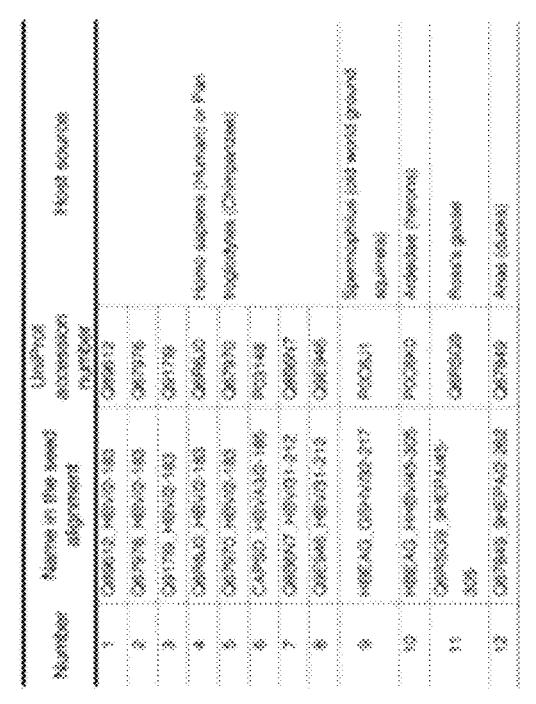
Figure 14C:
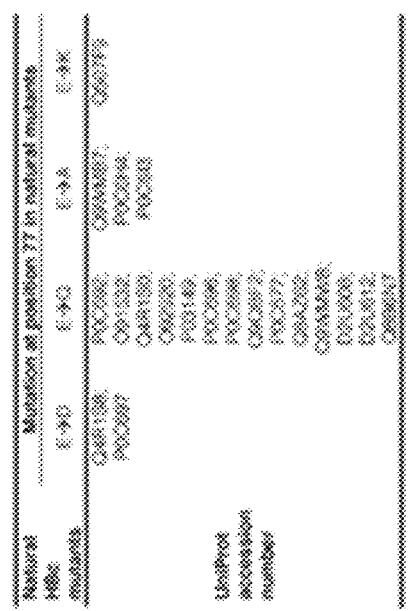

By examining HBc protein sequences from the UniProt database (The UniProt C, 2014) and the Hepatitis core family PF00906 sequences from the Pfam database (Punta et al., 2012), we found a few natural mutants with only one negatively charged amino acid (D78) on the monomer spike tip, but none had both negative charges (E77, D78) removed; consistent with our mutational results (FIG. 14). One natural mutant (UniProt accession number: Q8B6N7) was quite novel; Q8B6N7 has a natural mutation of E77Q leaving one net negative charge at the 78 site. Comparing it to the rest of around 7000 members of the Hepatitis core family PF00906, Q8B6N7 was the only mutant heavily mutated throughout the spike domain. FIG. 4A compares the amino acid sequence of Q8B6N7 to that of a more conserved HBc protein (UniProt accession number: P03147).

FIG. 4 shows new mutants produced by transplanting the spike region of the natural mutant, Q8B6N7, into HBc SS1. FIG. 4A displays the difference between the HBc protein used in this study (UniProt accession number: P03147) and a natural mutant (UniProt accession number: Q8B6N7). The residue differences are shown in the protein structures and amino acid sequences. Both protein sequences are truncated at 149. The differences are underlined and marked in yellow. FIG. 4B is an illustration for the creation of two new mutants (SS1(ST) and SS1(HP)). FIG. 4C provides the CFPS yields and soluble yields after dialysis against buffer with 0.5 M NaCl or 1.5 M NaCl. FIG. 4D is SEC analysis after dialysis against buffer with 0.5 M NaCl or 1.5 M NaCl. FIG. 4E shows the different conjugation sites tested on the SS1(HP) protein spike tip at six different nnAA sites (N75AHA, L76AHA, Q77AHA, D78AHA, Q79AHA, and A80AHA). FIG. 4F provides the soluble CFPS yields and soluble yields after 1.5M NaCl dialysis. FIG. 4G shows the TEM image of HBc SS1(HP) 78AHA VLP. Lastly, FIG. 4H is the reducing SDS-PAGE autoradiogram analysis of click-reaction products of HBc SS1(HP) VLP with flagellin, GMCSF, IM9-ScFv and CpG DNA in which Cu(I) was not added to the control reaction.

To estimate the effects of the naturally selected mutations in Q8B6N7 on the functional characteristics of the VLP, the spike (either the spike tip (ST) or the whole hydrophobic pocket (HP)) from Q8B6N7 was transplanted into the SS1 mutant of P03147 to create two new mutants: SS1(ST) and SS1(HP) (FIG. 4B).

The spike sequence of the HBc polypeptide is a sequence forming alpha helix 3 ($\alpha$3) to end of alpha helix 4b ($\alpha$4b), which forms a hairpin structure and participates in a 4-helix bundle in an HBc capsid dimer (Wynne et al., 1999; Conway et al., 1997; Bottcher et al., 1997). Its sequence starts with amino acid residue at position 50 and ends with amino acid residue at position 110 of SEQ ID NO: 1 or UniProt accession number P03147, starts with amino acid residue at position 79 and ends with amino acid residue at position 139 of UniProt accession number Q8B6N7, or alternatively, is a sequence with amino acid residues equivalent to position 50 to 110 of SEQ ID NO: 1 or UniProt accession number P03147 or equivalent to position 79 to 139 of UniProt accession number Q8B6N7 in aligned HBV sequences.

As for the whole hydrophobic pocket, the sequence starts with amino acid residue at position 59 and ends with amino acid sequence at position 97 of SEQ ID NO: 1 or UniProt accession number P03147, starts with amino acid residue at position 88 and ends with amino acid residue at position 126 of UniProt accession number Q8B6N7, or alternatively, is a sequence with amino acid residues equivalent to position 59 to 97 of SEQ ID NO: 1 or UniProt accession number P03147 or equivalent to position 88 to 126 of UniProt accession number Q8B6N7 in aligned HBV sequences.

For the spike tip, the sequence used starts with amino acid residue at position 74 and ends with amino acid sequence at position 81 of SEQ ID NO: 1 or UniProt accession number P03147, starts with amino acid residue at position 103 and ends with amino acid residue at position 110 of UniProt accession number Q8B6N7, or alternatively, is a sequence with amino acid residues equivalent to position 74 to 81 of SEQ ID NO: 1 or UniProt accession number P03147 or equivalent to position 103 to 110 of UniProt accession number Q8B6N7 in aligned HBV sequences.

The HP transplants allowed us to evaluate the effect of changing only the spike region while keeping the VLP shell the same. These two new mutants showed improved production solubility over mutant SS1(B1) (FIG. 4C). However, SS1(ST) and SS1(HP) still did not self-assemble into VLPs after 0.5M dialysis (FIG. 4D), supporting our initial observations of the importance of negative tip spike charges. However, as before, dialysis against buffer with a higher ionic strength (1.5 M NaCl) stimulated assembly of the mutated subunits into VLPs. These new VLPs were then separated by SEC and oxidized by diamide to form the disulfide-bond network. Proper assembly of the SS1(ST) and SS1(HP) VLPs was verified by non-reducing SDS-PAGE and sucrose gradient centrifugation (FIG. 6). Because SS1(HP) had better solubility than SS1(ST) (FIG. 4C), SS1(HP) was chosen for subsequent studies. We also reasoned that, with 18 mutations in the spike region, SS1(HP) would cause fewer antigenicity and immunogenicity concerns.

To identify the best conjugation site for SS1(HP), AHA was introduced individually at amino acid positions 75 to 80 (N75AHA, L76AHA, Q77AHA, D78AHA, Q79AHA, and A80AHA; FIG. 4E). These mutants were all stabilized by the new SS1 disulfide bridge (D29C-R127C). Introducing the nnAA at D78 is particularly attractive as it totally removes the negative charges at the tip. CFPS results indicated that all these mutants accumulated as mostly soluble product except mutant D78AHA (FIG. 4F). However, after dialysis against 1.5 M NaCl, the soluble yield of mutant D78AHA reached about 70%. SEC results showed that all these mutants self-assembled into VLPs (FIG. 6). The VLPs were then separated by SEC and oxidized by diamide. TEM analysis showed that the size of the mutant SS1(HP) 78AHA VLP was correct (FIG. 4G). Importantly, the heavily mutated HP spike allowed assembly after removal of all the spike tip charges in contrast to results with the more conserved spike.

Conjugation to these mutated VLPs was then tested with the four molecules previously evaluated: flagellin, GMCSF, IM9-ScFv, and CpG DNA; each with exposed alkynes. The conjugation reaction results (FIG. 4H) showed that the removal of surface negative charges on the HBc VLP greatly improved the conjugation efficiency of IM9-scFv and CpG DNA without reducing conjugation of GMCSF or flagellin. HBc SS1(HP) D78AHA was therefore chosen for further development. To address the possibility that the change to the hydrophobic pocket (HP) spike from Q8B6N7 might cause a different assembly stabilization disulfide bond to be superior in the shell, the different positions (SS1-SS10) were again tested. SS1 was still the best (FIG. 6F-G) suggesting that the spike transplant did not significantly distort the shell structure.

Hydrophobic interaction and electrostatic repulsion during HBc VLP assembly. Attractive hydrophobic interactions have been thought to provide the main driving force for the assembly of viral capsids (Alexander et al., 2013). However, in this study, the surface-exposed negative charges on the spike tip greatly influenced the assembly efficiency of the HBc subunits (FIG. 15A). Reducing the negative charges on the spike tip caused the formation of insoluble aggregates. The electrostatic repulsion between the HBc spike tips may provide a beneficial opposition to capsid assembly. Our observations (summarized in FIG. 15) suggest a critical dynamic balance between hydrophobic attractions and electrostatic repulsions for correct HBc VLP assembly (at least in vitro). For simplicity, we do not consider the cases with nnAA introduction here. Reducing the negative charges on the spike tip may have allowed nonproductive hydrophobic interactions to cause aberrant aggregation. Increasing the ionic strength strengthens hydrophobic attractions, apparently allowing productive assembly interactions to dominate.

FIG. 15B compares the hydrophobic pocket of HBc WT protein with that of the HBc HP variant. Helices α1 and α2 (FIG. 15B) pack together to form a stable dimer by hydrophobic interactions (Alexander et al., 2013). Although HBc WT and HBc HP have different hydrophobic residues in the dimeric hydrophobic pocket, the number of these attractive residues is similar, 20 for WT and 18 for the HP spike. We suggest that future work can use these data and considerations to establish a well-defined simulation of in vitro HBc VLP assembly.

Figure 16A:
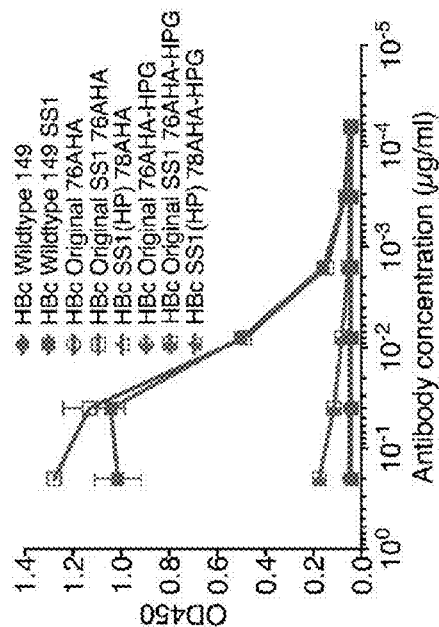
FIG. 16A-16D. Antigenicity and immunogenicity of HBc VLPs.

Antigenicity and Immunogenicity Evaluation of HBc VLPs in Mice. Because of the potential to use HBc VLPs as vaccine and drug delivery scaffolds, we next evaluated both the antigenicity and immunogenicity of HBc VLP variants. The HBc protein has been reported to be an important target for antiviral immunity (Chen et al., 2004). The major antigenic epitopes lie on the outside of the capsid structure, particularly at the tip of spikes. The major immunodominant epitope is the polypeptide T74 to L84 (TNLEDPASRDL, FIG. 16A) (Homs et al., 2011).

Figure 16B:
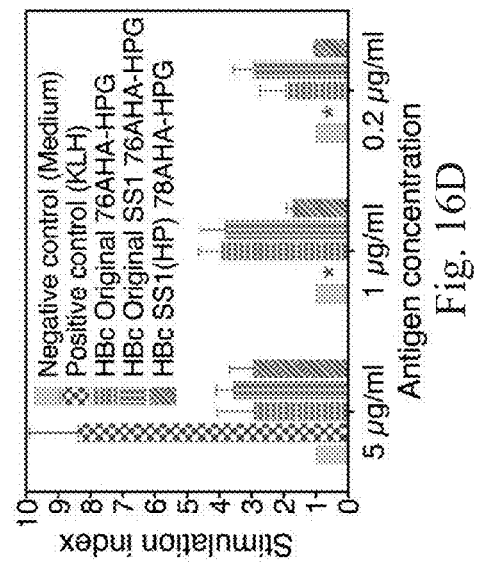

The antigenicity of HBc VLPs was examined by enzyme linked immunosorbent assay (ELISA). Monoclonal antibody C1-5 was used in this assay as it recognizes the T74 to A80 spike epitope. ELISA results (FIG. 16B) showed that antibody C1-5 could bind to S—S stabilized HBc VLPs (HBc Wild-type SS1 and HBc Original SS1 76AHA) but not the Wild-type VLP or the HBc Original 76AHA VLP ("Original" refers to the wild type P03147 version with nnAA incorporation). This result suggests that introducing the SS1 disulfide bridge either changes the surface conformation of the HBc subunit in the VLP or allows the stabilized VLP to produce much larger signals in a sandwich type assay. In contrast, due to the transplant of a new spike into the HBc SS1(HP) 78AHA VLP, it could not be recognized by antibody C1-5. Notably, pre-existing HBc-specific antibodies in HBV-infected patients should not interfere with HBc(HP) VLP based vaccines and delivery vehicles. Additionally, VLPs with the nnAA, HPG (homopropargylglycine), conjugated to the surface nnAA AHA sites were evaluated to see if smaller surface modifications would also block C1-5 antibody recognition. The conjugation of HPG abrogated the recognition of HBc antigen protein by antibody C1-5, as shown in FIG. 16B.

Figure 16C:
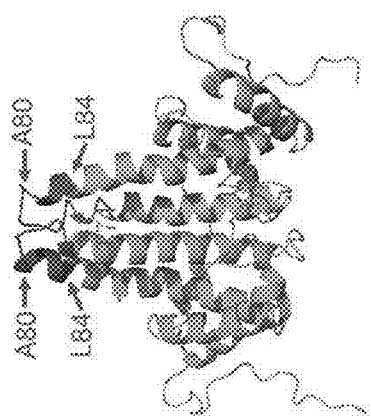
Figure 16D:
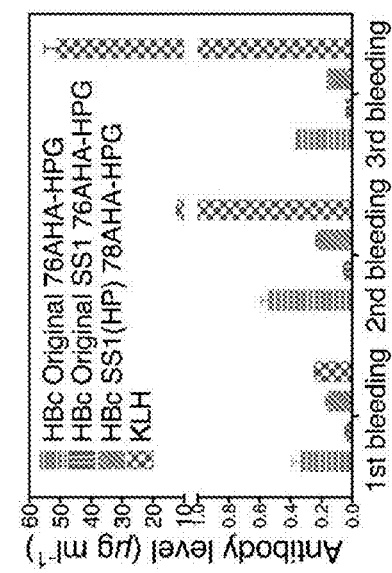
Figures 17A, 17B:
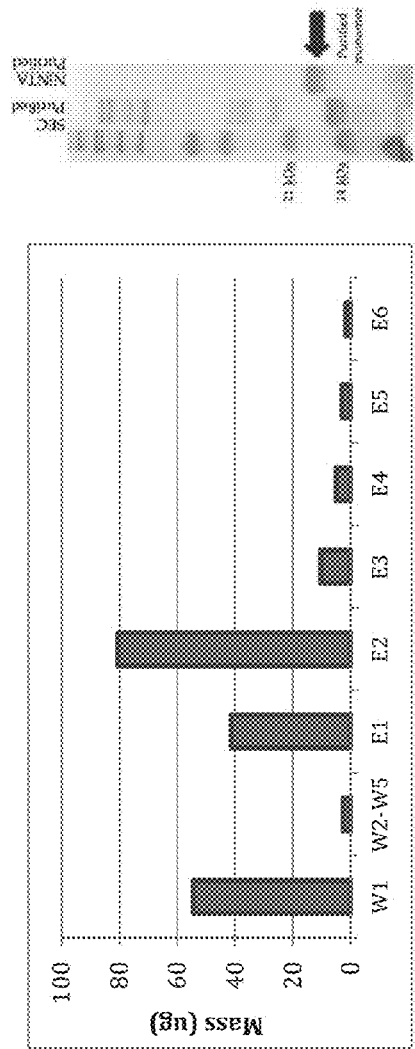
FIG. 17A-17B shows (FIG. 17A) a representative Ni-NTA column purification profile from one of the triplicate runs. 269.8 μg of protein was loaded on this column.
Figure 19:
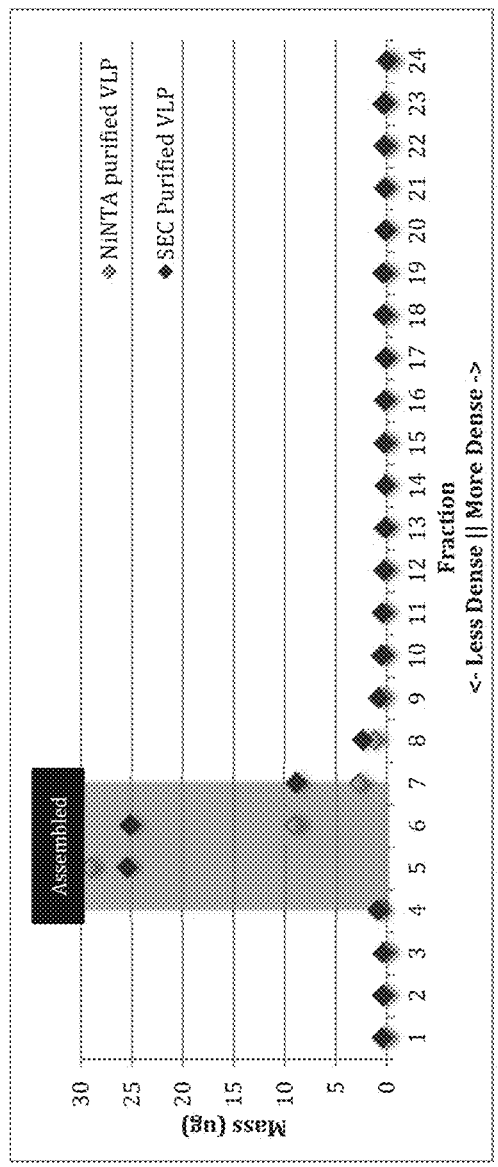
FIG. 19 Shows representative Sucrose Gradient Sedimentation profiles.

Ideally the VLP as a carrier vehicle would induce only a weak or no immune response to avoid suppressing the immunogenicity of conjugated molecules. The immunogenicity of three HPG surface modified VLPs (HBc Original 76AHA-HPG, HBc Original SS1 76AHA-HPG, and HBc SS1(HP) 78AHA-HPG) were evaluated in mice. (After VLP surface conjugation to assemble vaccines and delivery agents, HPG is typically reacted with the assembled agent to cover any unreacted azide surface residues that may have been blocked by steric hindrance.) Keyhole limpet hemocyanin (KLH) was used as the positive control as it is the most widely used carrier protein for immunogen preparation (Harris and Markl, 1999). All agents were administered with 3 μg doses intradermally. Compared with KLH, the mice injected with VLPs produced very low levels of anti-VLP antibodies (<0.6 μg/ml), as shown in FIG. 16C. Most notably, the detected anti-VLP antibody levels did not rise even after repeated inoculations suggesting very low humoral immunogenicity. Antigen-specific T-cell responses were evaluated using a lymphocyte proliferation assay (Kruisbeek et al., 2004). All three HBc VLPs had a significantly lower stimulation index than KLH (FIG. 16D), indicating that the T cell responses to HBc VLPs were also low. HBc SS1(HP) 78AHA-HPG VLP had a lower stimulation index than the other two VLPs. Therefore, the stabilized and modified HBc SS1(HP) 78AHA VLP appears to be an excellent vehicle for medical applications.

The HBc VLP was extensively modified to improve its functional properties for important medical applications. Using an E. coli-based CFPS system, ten positions were evaluated for the introduction of artificial disulfide bridges. Introducing cysteines cross-linked both the 5-fold and 6-fold assembly junctions to augment the intra-dimer disulfides already present and provided stability even against SDS-mediated disassembly. The new interdimer disulfide bonds will stabilize the VLP during modification, formulation, storage, and administration of vaccines and targeted therapeutics. Moreover, such bonds confer only conditional stability such that the VLPs would be expected to open in the relatively reduced cytoplasmic environment for drug release.

To present molecules on the VLP surface with consistent orientation (much like natural viruses), we introduced non-natural amino acids and used click chemistry. To improve the conjugation efficiencies, we reduced the intense electronegativity on the tip of the protruding surface spikes. However, surprisingly, these mutants assembled very poorly. Encouraged that partial charge reduction improved conjugation, we next explored a more radical change: the replacement of the entire surface spike with an extensively modified version from the natural mutant Q8B6N7. This enabled the assembly of a VLP with essentially no surface charge and with a spike expected to exhibit low antigenicity and immunogenicity. The stabilized and modified new HBc SS1(HP) 78AHA VLP did indeed exhibit low immunogenicity in mice and was not recognized by a common anti-HBc antibody. It also enable efficient surface attachment of agents with both positive and negative charge density. This highly engineered VLP demonstrates great promise for medical agents such as vaccines, delivery vehicles, imaging agents, etc.

Example 4

HBc SS1(HP) 76M 6H—New Purification and Assembly Method

To provide VLP with greater purity and to facilitate the loading of the VLPs with cargo for targeted delivery applications, a new purification and assembly protocol was developed. The is procedure uses a C-terminal affinity tag to purify unassembled HepBc subunits before stimulating VLP assembly.

The gene sequence encoding the human Hepatitis B core protein (HBc), truncated at the C-terminus at amino acid 149 was codon optimized for *E. Coli* and synthesized into a pET24a(+) vector (Novagen, San Diego, Calif.) previously by the Swartz lab. To incorporate methionine analogues, two mutations (M66S and L76M) were also previously introduced. DNA encoding a linker (GSAAP) followed by a 6-Hisdidine purification tag was added to the 3' end of the gene using QuikChange PCR (Stratagene, La Jolla, Calif.). pET24a-HBc149-M66S-L76M-6H was transformed into DH5α cells and the plasmid was purified with Qiagen Plasmid Maxi Kit (Qiagen, Valencia, Calif.) for use in cell-free protein synthesis (CFPS).

Cell Free Protein Synthesis (CFPS) was conducted using the PANOx-SP cell-free system. The 1 mL reactions were conducted at 30° C. for 6 h in 6-well tissue culture plates (BD Falcon #3046, BD, Franklin Lakes, N.J.). 5 μM L-[U-14C]-Leucine (PerkinElmer, Waltham, Mass.) was added to the reactions for measuring protein yields and to measure protein concentration across each step of the purification and assembly process.

To remove unincorporated L-[U-14C] leucine, the cell-free product was immediately dialyzed in 6-8000 MWCO Spectra/Por molecular-porous Membrane Tubing (Spectrum Labs, Rancho Dominguez, Calif.) against the Loading Buffer (LB) (50 mM Tris-HCl, 10 mM magnesium diglutamate ($Mg(Glu)_2$), 10 mM monoammonium glutamate ($NH_4$(Glu)), 175 mM monopotassium glutamate (K(Glu)), 1mM Putrescine, 1.5 mM Spermidine, 5 mM DTT, 0.01% Tween20, 25 mM lmidzole, pH 7.4) with two buffer exchanges in series (2 hours and overnight).

The dialyzed cell-free reaction product was loaded on a 1 mL Ni-NTA column equilibrated with 5 column volumes of the LB. The column was washed with 5 column volume (CV) of the LB and eluted with 6 CV of 500 mM imidazole in the LB collecting 1 ml fractions (FIG. 17A). FIG. 17B indicates that the new producer provides the HBc subunits with much higher purity than the previous method in which the VLPs were assembled and then purified with size exclusion chromatography.

PD-10 desalting columns (GE Healthcare) were used to exchange buffers to remove imidazole. Since the loading volume for these columns was 2.5 mL, the first two elution fractions and half the volume of the third were collected and loaded on the column. The protein was eluted from the PD-10 column into an imidazole free buffer: 50 mM Tris-HCl, 10 mM $Mg(Glu)_2$, 10 mM $NH_4$(Glu), 175 mM K(Glu), 1 mM Putrescine, 1.5 mM Spermidine, 1 mM DTT, pH 7.4. The 3.5 mL elution was concentrated down to 0.5 mL using centrifugal filter units (EMD Millipore, Amicon Ultra-4).

Assembly of VLP was carried out under high salt condition following addition of a single bolus salt spike to attain a final concentration of 1.5 M NaCl. The solution was then incubated overnight at 4° C.

The assembled VLP was analyzed using 2 orthogonal methods to confirm assembly: Size Exclusion Column (SEC) and Sucrose Gradient ultracentrifugation.

The small-scale SEC columns were packed with Sepharose 6 FastFlow resin (GE Healthcare). 2.2 mL of the resin was packed in a gravity-flow polystyrene column and equilibrated with 5 CV of the assembly buffer: 50 mM Tris-HCl, 1.5 M NaCl, 10 mM $Mg(Glu)_2$, 10 mM $NH_4$(Glu), 175 mM K(Glu), 1mM Putrescine, 1.5 mM Spermidine, 1 mM DTT, pH 7.4. After loading the sample, the column was washed with the assembly buffer and 150 μL fractions were collected for protein concentration measurement. FIG. 18 shows that nearly all of the HBc subunits assembled into VLPs.

The assembled VLP samples were also subjected to velocity sedimentation. Ten to forty percent w/v continuous sucrose gradients were prepared in the assembly buffer in Polyallomer 16×102 mm centrifuge tubes (Beckman Coulter) with the Gradient Master Ver 3.05L Gradient Maker (Biocomp Instruments, Inc., Fredericton, Canada). A 200 uL VLP sample was loaded on top of the gradient and centrifuged at 31,000 rpm for 7 hours, at 4° C., in a Beckman Coulter SW-32.1 swinging bucket rotor (Fullerton, Calif.). A Beckman L8-M ultracentrifuge was used with a profile 7 slow acceleration and deceleration setting. 750 μL fractions were collected for protein concentration measurement. FIG. 19 confirms that VLPs prepared by the new procedure are correctly assembled.

The VLP purification and assembly experiment was done in triplicate.

The mass balances over the Ni-NTA columns were 72.3±1.4% (FIG. 17A-B). Of the loaded samples, 51.8±2.1% of the VLP protein was recovered in the elution fractions.

Over the size exclusion column, an expected peak was seen in the VLP fractions (5-10) (FIG. 18). The mass balance across the column was 95.8±19.4%, with 81.9±3.0% of the loaded sample being assembled VLP.

Fractions collected from the sucrose gradient sedimentation run revealed the expected VLP peak in fractions 5 and 6 (FIG. 19). The mass balance over all fractions was 120±35.15%, with 92.8±0.04% of the sample in the assembled VLP fractions.

References

Aguilar J C, et al. (2004) Development of a nasal vaccine for chronic hepatitis B infection that uses the ability of hepatitis B core antigen to stimulate a strong Th1 response against hepatitis B surface antigen. *Immunology and cell biology* 82(5):539-546.

Aida Y & Pabst M J (1990) Removal of endotoxin from protein solutions by phase separation using Triton X-114. *Journal of immunological methods* 132(2):191-195.

Alexander C G, et al. (2013) Thermodynamic origins of protein folding, allostery, and capsid formation in the human hepatitis B virus core protein. *Proceedings of the National Academy of Sciences of the United States of America* 110 (30):E2782-2791.

Bottcher B, Wynne S A & Crowther R A (1997) Determination of the fold of the core protein of hepatitis B virus by electron cryomicroscopy. *Nature* 386(6620):88-91.

Bundy B C & Swartz J R (2010) Site-Specific Incorporation of p-propargyloxyphenylalanine in a cell-free environment for direct protein-protein Click conjugation. *Bioconjugate Chem* 21(2):255-263.

Calhoun K A & Swartz J R (2005) Energizing cell-free protein synthesis with glucose metabolism. *Biotechnol Bioeng* 90(5):606-613.

Calhoun K A & Swartz J R (2006) Total amino acid stabilization during cell-free protein synthesis reactions. *J Biotechnol* 123(2):193-203.

Ceres P & Zlotnick A (2002) Weak protein-protein interactions are sufficient to drive assembly of hepatitis B virus capsids. Biochemistry 41(39):11525-11531.

Chen M T, et al. (2004) A function of the hepatitis B virus precore protein is to regulate the immune response to the core antigen. *Proceedings of the National Academy of Sciences of the United States of America* 101(41):14913-14918.

Clarke B E, et al. (1987) Improved immunogenicity of a peptide epitope after fusion to hepatitis B core protein. *Nature* 330(6146):381-384.

Conway J, et al. (1997) Visualization of a 4-helix bundle in the hepatitis B virus capsid by cryo-electron microscopy. *Nature* 386(6620):91-94.

Cubas R, et al. (2009) Virus-like particle (VLP) lymphatic trafficking and immune response generation after immunization by different routes. *J Immunother* 32(2):118-128.

Deiters A & Schultz P G (2005) In vivo incorporation of an alkyne into proteins in *Escherichia coli*. *Bioorg Med Chem Lett* 15(5):1521-1524.

Ganem D & Prince A M (2004) Hepatitis B virus infection--natural history and clinical consequences. *The New England Journal of Medicine* 350(11):1118-1129.

Harris J R & Markl J (1999) Keyhole limpet hemocyanin (KLH): a biomedical review. *Micron* 30(6):597-623.

Hernandez-Garcia A, et al. (2014) Design and self-assembly of simple coat proteins for artificial viruses. *Nat Nanotechnol* 9(9):698-702.

Homs M, et al. (2011) HBV core region variability: effect of antiviral treatments on main epitopic regions. *Antiviral therapy* 16(1):37-49.

Jewett M C & Swartz J R (2004) Mimicking the *Escherichia coli* cytoplasmic environment activates long-lived and efficient cell-free protein synthesis. *Biotechnol Bioeng* 86(1):19-26.

Kanter G, et al. (2007) Cell-free production of scFv fusion proteins: an efficient approach for personalized lymphoma vaccines. *Blood* 109(8):3393-3399.

Kegel W K & Schoot Pv P (2004) Competing hydrophobic and screened-coulomb interactions in hepatitis B virus capsid assembly. *Biophysical Journal* 86(6):3905-3913.

Kourtis I C, et al. (2013) Peripherally administered nanoparticles target monocytic myeloid cells, secondary lymphoid organs and tumors in mice. *Plos One* 8(4):e61646.

Kruisbeek A M, Shevach E, & Thornton A M (2004) Proliferative assays for T cell function. *Current Protocols In Immunology/* edited by John E. Coligan . . . [et al.] Chapter 3:Unit 3 12.

Lu Y, Welsh J P, Chan W, & Swartz J R (2013) *Escherichia coli*-based cell free production of flagellin and ordered flagellin display on virus-like particles. *Biotechnol Bioeng* 110(8):2073-2085.

Lu Y, Welsh J P, & Swartz J R (2014) Production and stabilization of the trimeric influenza hemagglutinin stem domain for potentially broadly protective influenza vaccines. *Proceedings of the National Academy of Sciences of the United States of America* 111(1):125-130.

Ohto U, et al. (2015) Structural basis of CpG and inhibitory DNA recognition by Toll-like receptor 9. Nature 520 (7549):702-705.

Pasek M, et al. (1979) Hepatitis-B virus genes and their expression in *Escherichia-coli*. *Nature* 282(5739):575-579.

Patel K G & Swartz J R (2011) Surface functionalization of virus-like particles by direct conjugation using azide-alkyne Click chemistry. *Bioconjugate Chem* 22(3):376-387.

Petry H, Goldmann C, Ast O, & Luke W (2003) The use of virus-like particles for gene transfer. *Curr Opin Mol Ther* 5(5):524-528.

Petsch D & Anspach F B (2000) Endotoxin removal from protein solutions. *J Biotechnol* 76(2-3):97-119.

Plotkin S (2014) History of vaccination. Proceedings of the National Academy of Sciences of the United States of America 111(34):12283-12287.

Pumpens P & Grens E (2001) HBV core particles as a carrier for B cell/T cell epitopes. *Intervirology* 44(2-3):98-114.

Punta M, et al. (2012) The Pfam protein families database. *Nucleic Acids Research* 40 (Database issue):D290-301.

Rostovtsev V V, Green L G, Fokin V V, & Sharpless K B (2002) A stepwise huisgen cycloaddition process: copper(I)-catalyzed regioselective "ligation" of azides and terminal alkynes. *Angew Chem Int Ed Engl* 41(14):2596-2599.

Roy P & Noad R (2008) Virus-like particles as a vaccine delivery system—Myths and facts. *Hum Vaccines* 4(1):5-12.

Schur F K M, et al. (2015) Structure of the immature HIV-1 capsid in intact virus particles at 8.8 angstrom resolution. *Nature* 517(7535):505-508.

Strable E, et al. (2008) Unnatural amino acid incorporation into virus-like particles. *Bioconjugate Chem* 19(4):866-875.

Swartz J R (2009) Universal cell-free protein synthesis. *Nature Biotechnology* 27(8):731-732.

Tissot A C, et al. (2010) Versatile virus-like particle carrier for epitope based vaccines. *Plos One* 5(3):e9809.

The UniProt C (2014) Activities at the Universal Protein Resource (UniProt). *Nucleic Acids Research* 42(D1):D191-D198.

Wynne S A, Crowther R A, & Leslie A G W (1999) The crystal structure of the human hepatitis B virus capsid. *Mol Cell* 3(6):771-780.

Zawada J F, et al. (2011) Microscale to manufacturing scale-up of cell-free cytokine production—a new approach for shortening protein production development timelines. *Biotechnol Bioeng* 108(7):1570-1578.

Zeltins A (2013) Construction and characterization of virus-like particles: a review. *Mol Biotechnol* 53(1):92-107.

Zlotnick A, et al. (2007) In vitro screening for molecules that affect virus capsid assembly (and other protein association reactions). *Nat Protoc* 2(3):490-498.

What is claimed is:

1. A stabilized, chimeric virus like particle (VLP) having an artificial disulfide bond network comprising multiple HBc polypeptides:
   a. wherein at least two amino acids of each of the HBc polypeptides are substituted with cysteine residues that can form interdimer disulfide bonds after the HBc is assembled into the VLP thereby forming the artificial disulfide bond network that stabilizes the VLP;
   b. wherein each of the HBc polypeptides comprises a spike sequence—which has been modified to have a lower negative charge or neutral charge compared to the spike sequence of the wild-type HBc polypeptide at neutral pH; and
   c. wherein two HBc polypeptides of (b) are dimerized to form a spike, and wherein the at least two amino acids are selected from the group consisting of P134-P135, P134-N136, P134-A137, and P135-N136 as provided in SEQ ID NO:1 or SEQ ID NO:2 or amino acid pairs at corresponding positions in aligned sequences of HBC polypeptides.

2. The stabilized VLP of claim 1, wherein the spike sequence of the HBc polypeptide is a sequence from amino-to-carboxyl end of (a) twenty four amino acids that form a long alpha helix 3 (α3) with 6.4 alpha helical turns followed by (b) five amino acids that loop back joined to (c) thirty-two amino acids that form alpha helix 4 (α4) with a kink that breaks the alpha helix 4 at the thirteenth amino acid separating α4 into (i) twelve amino acids that form three alpha helical turns of alpha helix4a (α4a) and (ii) nineteen amino acids that form five alpha helical turns of alpha helix 4b (α4b), which forms a hairpin structure and (b) participates in a 4-helix bundle in the HBc dimer of claim 1 (c), or portion thereof.

3. The stabilized VLP of claim 2, wherein the sequence forming alpha helix 3 (α3) to the end of alpha helix 4b (α4b) is a sequence starting with amino acid residue, proline, at position 50 and ending with amino acid residue, phenylalanine, at position 110 of SEQ ID NO: 1 or SEQ ID NO: 32 or corresponding residues thereto.

4. The stabilized VLP of claim 3, wherein the amino acid residues corresponding to position 50 to 110 of SEQ ID NO: 1 or SEQ ID NO: 32 are in any of: SEQ ID NOS: 111-116 beginning with amino acid residue, alanine or proline, at position 50 and ending with amino acid residue, phenylalanine, at position 110.

5. The stabilized VLP of claim 1, wherein the spike of (c) has a hydrophobic pocket or portion thereof and a spike tip.

6. The stabilized VLP of claim 5, wherein the sequence of the hydrophobic pocket is a sequence selected from the group consisting of:
   i. amino acid residue, isoleucine, at position 59 and ends with amino acid residue, phenylalanine, at position 97 of SEQ ID NO: 1 or SEQ ID NO: 32 or corresponding residues thereto, or
   ii. amino acid residue, valine, at position 88 and ending with amino acid residue, isoleucine, at position 126 of SEQ ID NO: 117 or corresponding residues thereto, and
   iii. an 39-amino acid sequence of SS1(HP) as shown in 2 SEQ ID NO: 110 beginning with valine (V) at position 59 and ending with isoleucine (I) at position 97.

7. The stabilized VLP of claim 6, wherein the amino acid residues corresponding to positions 59 to 97 of SEQ ID NO: 1 or SEQ ID NO: 32 begin with isoleucine or valine at amino acid 59 and end with leucine, phenylalanine or isoleucine at amino acid 97 ; or aligned HBV sequences or portions thereof corresponding to position 59 to 97 of SEQ ID NO: 1 or SEQ ID NO: 32.

8. The stabilized VLP of claim 6, wherein the spike tip comprises an 8-amino acid sequence of SS1(ST) having:
   i. a sequence starting with amino acid residue, threonine, at position 74 and ending with amino acid residue, serine, at position 81 of SEQ ID NO: 1 or SEQ ID NO: 32 or corresponding residues thereto; or
   ii. a sequence starting with amino acid residue, asparagine, at position 103 and ending with amino acid residue, alanine, at position 110 of SEQ ID NO: 117 or corresponding residues thereto.

9. A stabilized, chimeric virus like particle (VLP) having an artificial disulfide bond network comprising multiple HBc polypeptides wherein:
   a. wherein at least two amino acids of each of the HBc polypeptides are substituted with cysteine residues that can form interdimer disulfide bonds after the HBc is assembled into the VLP thereby forming the artificial disulfide bond network that stabilizes the VLP;
   b. wherein each of the HBc polypeptides comprises a spike sequence of an HBc polypeptide which has been modified to have a lower negative charge or neutral charge compared to the spike sequence of the wild-type HBc polypeptide at neutral pH; and
   c. wherein two HBc polypeptides of (b) are dimerized to form a spike and wherein the at least two amino acids of the HBC polypeptide so substituted are any of P134-P135, P134-N136, P134-A137, or P135-N136 as shown in SEQ ID NO:1 or SEQ ID NO:2.

10. The polypeptide of claim 1, additionally comprising substituting a cysteine at amino acid position 61 of SEQ ID NO: 1 or SEQ ID NO: 2 with a non-cysteine amino acid so as to further stabilize a VLP or reduce the possibility of self-assembly to a VLP with T=3 icosahedral symmetry.

* * * * *